(12) United States Patent
Albed Alhnan et al.

(10) Patent No.: US 12,714,675 B2
(45) Date of Patent: Aug. 25, 2026

(54) SOLID DOSAGE FORM PRODUCTION

(71) Applicant: UNIVERSITY OF LANCASHIRE, Lancashire (GB)

(72) Inventors: Mohamed Albed Alhnan, Lancashire (GB); Tochukwu Chijioke Okwuosa, Lancashire (GB)

(73) Assignee: University of Lancashire, Lancashire (GB)

(*) Notice: Subject to any disclaimer, the term of this patent is extended or adjusted under 35 U.S.C. 154(b) by 279 days.

(21) Appl. No.: 18/336,458

(22) Filed: Jun. 16, 2023

(65) Prior Publication Data

US 2024/0165040 A1 May 23, 2024

Related U.S. Application Data

(63) Continuation of application No. 17/338,840, filed on Jun. 4, 2021, now Pat. No. 11,717,485, which is a continuation of application No. 16/320,384, filed as application No. PCT/GB2017/052173 on Jul. 25, 2017, now Pat. No. 11,045,426.

(30) Foreign Application Priority Data

Jul. 25, 2016 (GB) ..................................... 1612853

(51) Int. Cl.
*A61K 9/48* (2006.01)
*A61K 31/519* (2006.01)

(52) U.S. Cl.
CPC .......... *A61K 9/4833* (2013.01); *A61K 9/4816* (2013.01); *A61K 9/4866* (2013.01); *A61K 31/519* (2013.01)

(58) Field of Classification Search
None
See application file for complete search history.

(56) References Cited

U.S. PATENT DOCUMENTS 11,045,426 B2 6/2021 Albed Alhnan et al.
11,717,485 B2 8/2023 Albed Alhnan et al.
2002/0015728 A1 2/2002 Payumo et al.
2014/0099351 A1 4/2014 Adams et al.
2016/0088870 A1 3/2016 Langeland
2016/0120808 A1* 5/2016 Hoover .................. B33Y 50/00 427/2.14

(Continued)

FOREIGN PATENT DOCUMENTS

CN 206934352 U * 1/2018
WO 1995/011007 A1 4/1995
WO 2001/087272 A2 11/2001

(Continued)

OTHER PUBLICATIONS

CN-206934352-U English Trans (Year: 2018).*

(Continued)

*Primary Examiner* — Jeffrey D Washville
(74) *Attorney, Agent, or Firm* — Barnes & Thornburg LLP

(57) ABSTRACT

The present disclosure utilises 3D printing technology, particularly fused filament fabrication, FFF, 3D printing, in conjunction with solid and/or liquid dispensers to produce solid dosage forms, such as pharmaceutical capsules. Such solid dosage forms have a shell, which is 3D printed, and a core, which is dispensed.

27 Claims, 13 Drawing Sheets

(56) References Cited

U.S. PATENT DOCUMENTS

2019/0125681 A1* 5/2019 Albed Alhnan ....... B33Y 50/02

FOREIGN PATENT DOCUMENTS

WO 2003/092633 A2 11/2003
WO 2014/143935 A1 9/2014
WO 2016/038356 A1 3/2016
WO 2018/137686 A1 8/2018

OTHER PUBLICATIONS

Search Report for Great Britain Patent Application No. GB1612853.0, mailed on Jan. 26, 2017, 4 pages.
International Search and Written Opinion for PCT International Application No. PCT/GB2017/052173, mailed on Sep. 11, 2017, 16 pages.
Masood, S., "Application of fused deposition modeling in controlled drug delivery devices," Assembly Automation, 2007, 27, 215-21.
Khaled, S. et al., "Desktop 3D printing of controlled release pharmaceutical bilayer tablets," International Journal of Pharmaceutics, 2014, 461, 105-11.

* cited by examiner

SOLID DOSAGE FORM PRODUCTION

CROSS-REFERENCE TO RELATED APPLICATIONS

This application is a continuation of U.S. application Ser. No. 17/338,840, filed Jun. 4, 2021, now U.S. Pat. No. 11,717,485, which is a continuation of U.S. Application Ser. No. 16/320,384, filed Jan. 24, 2019, now U.S. Pat. No. 11,045,426, which is a national stage entry under 35 U.S.C. § 371 of PCT International Application No. PCT/GB2017/052173, filed Jul. 25, 2017, which claims the benefit of Great Britain Patent Application No. 1612853.0, filed Jul. 25, 2016, the disclosures of each of which are incorporated herein by reference in their entirety.

INTRODUCTION

The present invention relates to a solid dosage form printing apparatus (and method for its use) in the production of solid dosage forms, such as capsules. The invention also relates to solid dosage forms obtainable by such printing methods and apparatus, a solid dosage form package, relevant materials and printing elements (and processes for their manufacture), a kit of parts, a computer for controlling the relevant printing process (and software and computer-implemented methods connected therewith), a system for collecting data relating to the solid dosage form production process (and databases associated therewith), and relevant blueprints for use in the printing of solid dosage forms.

BACKGROUND

The production and consumption of medicines, nutraceuticals, and food supplements (collectively referred to herein as "healthcare dosage forms"), in solid dosage form (e.g. tablets, implants, etc.) is ever increasing, not least due to an increased reliance on such products by national health services and the like in an increasingly health-conscious society. Where possible, solid dosage forms tend to be most preferred, relative to other formulations (e.g. injectable liquid formulations), due to their ease of administration (i.e. usually orally) which gives rise to better patient compliance, storability and transportability (low space requirements and ease of packaging), high stability (longer lifetimes—less degradation). However, despite the significant advantages of solid dosage forms over other dosage forms, they are often more onerous to manufacture (in terms of the number of both ingredients and processing steps) and are generally only cost effective to produce on large scale, meaning large manufacturing facilities with sophisticated equipment is usually required. These manufacturing limitations have a detrimental impact on consumer choice and/or the customisability of healthcare dosage forms since, for example, it is impractical and non-cost effective to mass produce a wide variety of different dosages for a given medicament via conventional manufacturing techniques. Consumers (e.g. patients) and healthcare professionals (e.g. doctors, pharmacists) must therefore make the best of the limited variety of dosages available, as dictated by the suppliers rather than a consumer's need.

Since the advent of 3-dimensional (3D) printing in the early 1980s, a number of researchers have attempted to make viable use of 3D printing technology to fabricate healthcare solid dosage forms. For instance, for well over a decade, MIT and Therics, Inc. have collaborated in the development of viable pill printing machines which utilise 3D printers to print solid pharmaceutical dosage forms in situ. The technology forms pills via a multi-layered 3D printing process involving precise printing of doses of a liquid drug solution onto thin layers of fine powder before further layers are then applied (e.g. further powder, binder, etc.). Examples of such processes are disclosed in earlier publications, such as WO95/11007 (MASSACHUSETTS INSTITUTE OF TECHNOLOGY) and WO03/092633 (THERICS, INC.), which describe inter alia the production of solid dosage forms having various structures and drug release profiles. However, regulatory approval (e.g. by the FDA or MHRA) for such 3D drug printing systems still remains elusive, and for the time being they are suitable only for low dose drug products, partly owing to the limited solubility of many drugs within the relevant ink solutions. As such, patient choice would still be very limited, as would the options of a doctor or pharmacist in providing specially-tailored treatments. Furthermore, resolution and shape of the solid dosage form still remains an issue. However, a particular issue with prior art 3D printing systems such as these is that the large number of different ingredients (and thus different printing cartridges etc.) needed to produce viable dosage forms imparts a high degree of complexity, user-unfriendliness, which in turn increases the likelihood of manufacturing errors, machine breakdown and malfunction, quality control variation, and regulatory viability (i.e. the FDA is less likely to approve drug printing systems which are prone to too many variables that may impact on the quality of the drug product). A further issue is the poor stability of some drug substances, especially in liquid ink formulations. This can severely limit the shelf-life of the drug source, thus posing large regulatory and cost issues.

Efforts have also been made to develop powder-based 3D printing in order to produce solid dosage forms with different drug release profiles. However, such techniques suffer from various shortcomings, including: the need to dry the powders, prolonged processing times, weak tablets which readily disintegrate, poor resolution and poor shape control, and limited control of drug release profiles.

The Applicants previous work outlined in WO2016/038356 (University of Central Lancashire), which primarily focussed on the use in 3D printing of drug-containing FDM filaments, aims to solve one or more of the aforesaid problems. However, there remains a need for alternative solutions. Though WO2016/038356 provides various innovative options for reducing the melting/softening temperatures of the drug-containing filaments, for some drugs (especially those with low decomposition temperatures) the filament printing temperatures can still be too high, and decomposition can occur during printing. Furthermore, the technology described in WO2016/038356 deploys significant proportions of thermoplastics in the formation of dosage forms, which can be undesirable and limit maximum drug-loadings. It is desirable to extend the scope of applicability of the 3D-printing technology described in WO2016/038356, for instance by allowing for a broader range of input materials. For example, the 3D printing of solid dosage forms containing polypeptides, proteins and other biopharmaceuticals is seen as desirable, notwithstanding the stability challenges these inherit. It is furthermore desirable to be able to provide such solid dosage forms with immediate, enteric, and/or extended release properties.

It is therefore an object of the invention to provide improved and/or alternative methods of producing solid dosage forms, and to suitable solve at least one problem inherent in the prior art.

SUMMARY OF THE INVENTION

According to a first aspect of the present invention there is provided an apparatus for preparing (or printing) a solid dosage form, the apparatus comprising:

- a 3D printer; and
- a build platform upon which the solid dosage form is printable (i.e. upon which the solid dosage form may be built); and
- a computer for controlling the 3D printer and optionally also the build platform;
- wherein the apparatus (or 3D printer) comprises or is otherwise associated with:
  - a structural printing nozzle for printing a pre-defined three-dimensional shell, comprising a shell composition, onto the build platform; and
  - a non-structural dispenser for unstructured dispensing of a core composition (which is suitably a liquid and/or a particulate solid) into the shell.

(wherein the FFF 3D printer is suitably operable via the computer, suitably a computer running pursuant to specialist solid dosage form printing software, and optionally also to one or more databases, to print the solid dosage form upon the build platform. Any one or more of the build platform, core composition, shell composition, and/or computer, and/or any part thereof, may suitably be integrated within or form a part of the FFF 3D printer).

According to a further aspect of the present invention there is provided a method of preparing (or printing) a solid dosage form, the method comprising:

- printing a pre-defined three-dimensional open shell, comprising a shell composition (or precursor thereof), onto a build platform;
- dispensing a core composition (or precursor thereof) into the open shell to produce an open core-containing shell;
- closing the open core-containing shell by printing a closure, optionally comprising the shell composition (or precursor thereof), thereupon.

According to a further aspect of the present invention, there is provided a computer for operating an apparatus for preparing (or printing) a solid dosage form as defined herein, wherein the computer comprises:

- an interface connecting or enabling connection of (whether wirelessly or wired) the computer to or within a solid dosage form printing apparatus (suitably to allow the computer to control and/or operate the aforesaid);

wherein the computer runs pursuant to solid dosage form printing software (and optionally also to one or more databases), which configures the computer to carry out the steps of:

- i) obtaining information (e.g. through manual user input or via one or more databases, optionally in response to a user-inputted reference, such as a patient's name) regarding one or more parameters pertaining to the solid dosage form to be printed (e.g. the active ingredient, active loading/dose, shape, release profile, etc.);
- ii) calculating the mass and/or volume of the solid dosage form to be printed based on the information obtained in step (i);
- iii) controlling printing of and relative proportions of ingredients within (i.e. make up of the solid dosage form) the solid dosage form by, on the basis of the information obtained in step (i) and calculations performed in step (ii):
  - a. controlling printing, deposition, and/or extrusion, of a shell composition (or precursor thereof wherever chemical transformations thereof occur after printing, deposition, and/or extrusion) and a core composition (or precursor thereof wherever chemical transformations thereof occur after printing, deposition, and/or extrusion);
  - b. optionally controlling printing, deposition, and/or extrusion, of one or more further printing compositions;
  - c. optionally controlling performance of one or more further processing steps.

According to a further aspect of the present invention, there is provided a computer-implemented method of operating an apparatus for preparing (or printing) a solid dosage form, or a computer-implemented method of preparing (or printing) a solid dosage form, the method comprising:

- operating a computer (with suitable data connections to the relevant printing apparatus, be them wired or wireless) running pursuant to solid dosage form printing software (and optionally also to one or more databases) to:
- i) obtain information (e.g. through manual user input or via one or more databases, optionally in response to a user-inputted reference, such as a patient's name) regarding one or more parameters pertaining to the solid dosage form to be printed (e.g. the active ingredient, active loading/dose, shape, release profile, shape, colour, etc.);
- ii) calculate the mass and/or volume of the solid dosage form to be printed based on the information obtained in step (i);
- iii) control printing of and relative proportions of ingredients within (i.e. make up of the solid dosage form) the solid dosage form by, on the basis of the information obtained in step (i) and calculations performed in step (ii):
  - a. controlling printing, deposition, and/or extrusion, of a shell composition (or precursor thereof wherever chemical transformations thereof occur after printing, deposition, and/or extrusion) and a core composition (or precursor thereof wherever chemical transformations thereof occur after printing, deposition, and/or extrusion);
  - b. optionally controlling printing, deposition, and/or extrusion, of one or more further printing compositions;
  - c. optionally controlling performance of one or more further processing steps.

According to a further aspect of the present invention, there is provided a computer program, comprising solid dosage form printing software code for performing the computer-implemented method defined herein when the computer program is run on a computer.

According to a further aspect of the present invention, there is provided a blueprint (or computer-readable code) for preparing (or printing) a solid dosage form as defined herein, the blueprint comprising information regarding one or more parameters pertaining to the solid dosage form to be printed (e.g. the active ingredient, active loading/dose, shape, release profile, shape, colour, etc).

According to a further aspect of the present invention, there is provided a computer-readable medium comprising solid dosage form printing software code executable to cause a computer to perform the computer-implemented method defined herein when the software code is executed on a computer.

According to a further aspect of the present invention, there is provided a computer-readable medium comprising a blueprint for preparing (or printing) a solid dosage form as defined herein.

According to a further aspect of the present invention there is provided a solid dosage form obtainable by, obtained by, or directly obtained by the method of preparing (or printing) a solid dosage form as defined herein.

According to a further aspect of the present invention there is provided a solid dosage form comprising a core and a three-dimensional shell surrounding the core;

wherein:

- the shell comprises a shell composition, the shell composition suitably comprising (or formed from) a 3D printing composition (e.g. a fused filament fabrication composition), wherein the shell composition is suitably (structurally) solid; and
- the core comprises a core composition, the core composition comprising an active ingredient, suitably a pharmaceutically, nutraceutically, or food-supplement active ingredient, wherein the core composition (suitably a solid, liquid, or gel) is suitably contained by the shell.

According to a further aspect of the invention, there is provided a method of producing a solid dosage form package, the method comprising packaging one or more solid dosage forms as defined herein, wherein the one or more solid dosage forms are optionally the same or different.

According to a further aspect of the invention, there is provided a solid dosage form package, obtainable by, obtained by, or directly obtained by the method of producing a solid dosage form package as defined herein.

According to a further aspect of the invention, there is provided a solid dosage form package, comprising one or more solid dosage forms, as defined herein, within a packaging.

According to a further aspect of the invention, there is provided a kit of parts comprising a shell composition (suitably as defined herein) and a core composition (suitably as defined herein).

Methods, and judicious variations thereof, of using an apparatus may be applied (as appropriate) to any of the apparatuses defined herein.

Any features, including optional, suitable, and preferred features, described in relation to any particular aspect of the invention may also be features, including optional, suitable and preferred features, of any other aspect of the present invention.

BRIEF DESCRIPTION OF THE DRAWINGS

For a better understanding of the invention, and to show how embodiments of the same are put into effect, reference is now made, by way of example, to the following diagrammatic drawings, in which.

DETAILED DESCRIPTION OF THE INVENTION

Definitions

Figure 1:
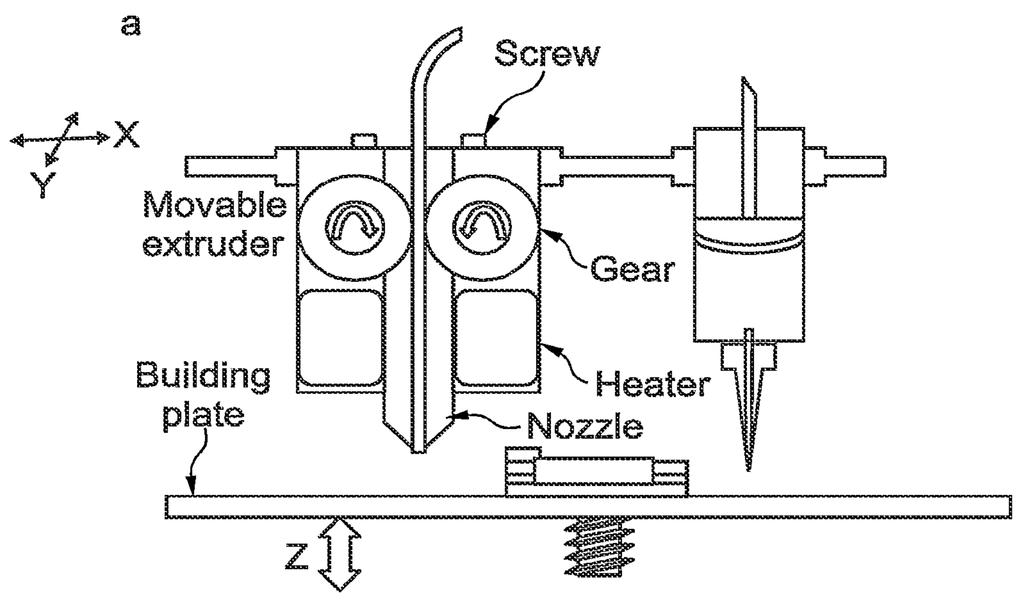
FIG. 1 is a schematic diagram of a dual FDM 3D printer adapted to accommodate a) a liquid dispenser or b) a powder/granule/pellets dispenser in combination with FDM 3D printer head.
Figure 1:
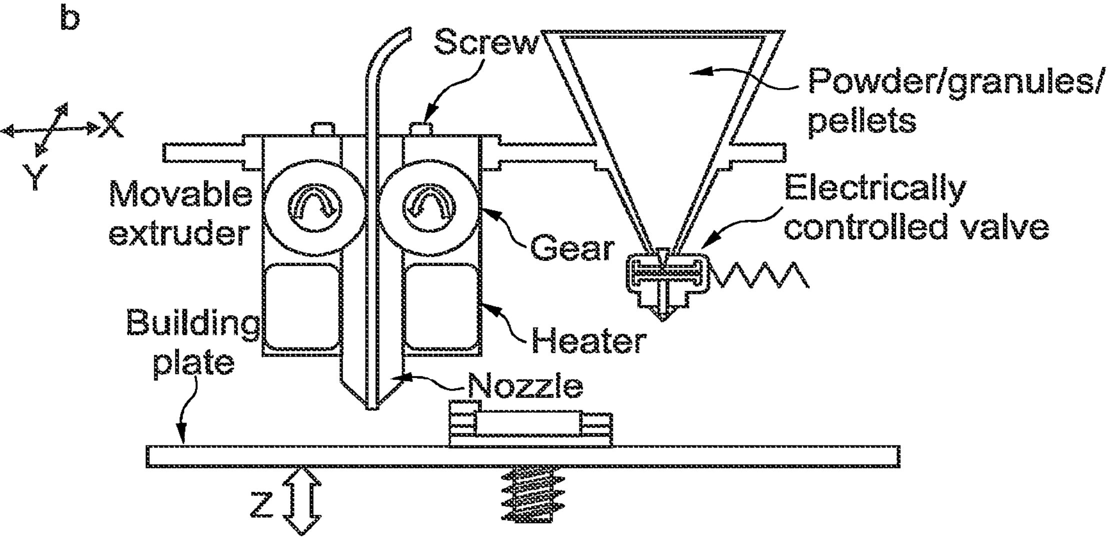

Unless otherwise stated, the following terms used in the specification and claims have the following meanings set out below.

Throughout the description and claims of this specification, the words “comprise” and “contain” and variations of them mean “including but not limited to”, and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

For the avoidance of doubt, it is hereby stated that the information disclosed earlier in this specification under the heading "Background" is relevant to the invention and is to be read as part of the disclosure of the invention.

Unless stated otherwise, any reference herein to the term "melt" (or its derivatives), especially in the context of melting filaments, suitably includes a glass transition or softening of a given material, suitably to allow extrusions thereof (e.g. through a nozzle). However, the term "melt" in the context of a defined "melting point" of a substance is as defined as per the art—a phase transition from solid to liquid.

Herein, references to "glass transition temperature" or "$T_g$" suitably refers to the temperature at which a material softens (e.g. to allow extrusion thereof). Suitably, glass transition temperatures (Tg) of materials described herein may be determined by a standard test method, suitably using dynamic mechanical analysis—a suitable test includes the testing protocol defined by ASTM E1640. Differential Scanning calorimetry (DSC) may also be utilised. For instance, glass transition temperatures may be discerned using the protocols set forth in ASTM E1356 and ASTM D7426. It will be understood by those skilled in the art that references herein to a particular material's glass transition temperature falling within a certain temperature range is intended to mean that at least one glass transition temperature of said material (which may or may not have multiple glass transition temperatures) falls within said temperature range. Suitably unqualified references to a "glass transition temperature" means at least one, suitably means the lowest glass transition temperature, and may suitably mean the glass transition temperature which absorbs the most thermal energy (or is most endothermic). The key, which is self-evident to those skilled in the art, is that sufficient softening of said material occurs under a particular set of circumstances (e.g. at the printing nozzle, where a filament needs to be softened in order to be extruded during the printing process, after which resolidification or rehardening may take place).

Unless stated otherwise, the term "viscosity" as used herein refers to a viscosity determined by means of a Brookfield viscometer (UL adapter/30 rpm/20° C.) in accordance with testing protocols defined by Ph. Eur. 2.2.10 or USP <912> method II.

Unless stated otherwise, any reference herein to an "average" value is intended to relate to the mean value.

Where a composition is said to comprise a plurality of stipulated ingredients (optionally in stipulated amounts of concentrations), said composition may optionally include additional ingredients other than those stipulated. However, in certain embodiments, a composition said to comprise a plurality of stipulated ingredients may in fact consist essentially of or consist of all the stipulated ingredients.

Herein, where a composition is said to "consists essentially of" a particular component, said composition suitably comprises at least 70 wt % of said component, suitably at least 90 wt % thereof, suitably at least 95 wt % thereof, most suitably at least 99 wt % thereof. Suitably, a composition said to "consist essentially of" a particular component consists of said component save for one or more trace impurities.

Where the quantity or concentration of a particular component of a given composition is specified as a weight percentage (wt % or % w/w), said weight percentage refers to the percentage of said component by weight relative to the total weight of the composition as a whole. It will be understood by those skilled in the art that the sum of weight percentages of all components of a composition will total 100 wt %. However, where not all components are listed (e.g. where compositions are said to "comprise" one or more particular components), the weight percentage balance may optionally be made up to 100 wt % by unspecified ingredients (e.g. a diluent, such as water, or other non-essentially but suitable additives).

Herein, unless stated otherwise, the term "parts" (e.g. parts by weight, pbw) when used in relation to multiple ingredients/components, refers to relative ratios between said multiple ingredients/components. Expressing molar or weight ratios of two, three or more components gives rise to the same effect (e.g. a molar ratio of x, y, and z is $x_1:y_1:z_1$ respectively, or a range $x_1$-$x_2$:$y_1$-$y_2$:$z_1$-$z_2$). Though in many embodiments the amounts of individual components within a composition may be given as a "wt %" value, in alternative embodiments any or all such wt % values may be converted to parts by weight (or relative ratios) to define a multi-component composition. This is so because the relative ratios between components is often more important than the absolute concentrations thereof in the liquid pharmaceutical compositions of the invention. Where a composition comprising multiple ingredients is described in terms of parts by weight alone (i.e. to indicate only relative ratios of ingredients), it is not necessary to stipulate the absolute amounts or concentrations of said ingredients (whether in toto or individually) because the advantages of the invention can stem from the relative ratios of the respective ingredients rather than their absolute quantities or concentrations. However, in certain embodiments, such compositions consists essentially of or consist of the stipulated ingredients and a diluents (e.g. water).

The term "mole percent" (i.e. mol %) is well understood by those skilled in the art, and the mol % of a particular constituent means the amount of the particular constituent (expressed in moles) divided by the total amount of all constituents (including the particular constituent) converted into a percentage (i.e. by multiplying by 100). The concept of mol % is directly related to mole fraction.

The term "substantially free", when used in relation to a given component of a composition (e.g. "a liquid pharmaceutical composition substantially free of compound X"), refers to a composition to which essentially none of said component has been added. When a composition is "substantially free" of a given component, said composition suitably comprises no more than 0.001 wt % of said component, suitably no more than 0.0001 wt % of said component, suitably no more than 0.00001 wt %, suitably no more than 0.000001 wt %, suitably no more than 0.0000001 wt % thereof, most suitably no more than 0.0001 parts per billion (by weight).

The term "entirely free", when used in relation to a given component of a composition (e.g. "a liquid pharmaceutical composition entirely free of compound X"), refers to a composition containing none of said component.

Suitably, unless stated otherwise, where reference is made to a parameter (e.g. pH, pKa, etc.) or state of a material (e.g. liquid, gas, etc.) which may depend on pressure and/or temperature, suitably in the absence of further clarification such a reference refers to said parameter at standard ambient temperature and pressure (SATP). SATP is a temperature of 298.15 K (25° C., 77° F.) and an absolute pressure of 100 kPa (14.504 psi, 0.987 atm).

Herein, the term "particle size" or "pore size" refers respectively to the length of the longest dimension of a given particle or pore. Particle and pore sizes may be measured using methods well known in the art, including a laser particle size analyser and/or electron microscopes (e.g. transmission electron microscope, TEM, or scanning electron microscope, SEM).

General Points and Advantages Relating to the Invention

The present invention deploys 3D printing technology to produce solid dosage forms, particularly pharmaceutical dosage forms, though the skilled person will readily appreciate that the principles of the invention are readily applicable to nutraceuticals and food supplements. The 3D printing apparatuses of the invention uniquely juxtapose standard 3D printing components with one or more non-printing dispensers so that together they are operable to print a solid 3D shell that encapsulates a core composition that has been dispensed into the shell in a non-printed manner. Standard 3D printing components may include printing nozzles, preferably comprising at least one non-powder-based printing nozzle such as those used in fused filament fabrication (FFF) printing, along with any relevant conveying and/or heating means that allows the printing compositions to be printed onto a surface, typically in a sequential-layered fashion. Non-printing dispensers may include any dispensing means that allows liquids and/or solids to be dispensed therefrom (suitably in bulk as opposed to a sequential-layered fashion) into a solid dosage form-sized containment vessel. This may, for example, include syringes (which may dispense liquids, emulsions, dispersions, suspensions, nanosuspensions, or even powdered solids), valve-operated and optionally pressurized hoppers (which may dispense solids or liquids), and the like. Importantly, the 3D shell is printed (generally discernible by a printed layered structure) whilst the inner core is not (and is instead a bulk mass of dispensed material with no discernible layered structure).

Suitably, concentric filling may be used to form the shell.

In general, printing of solid dosage forms of the invention may be achieved by initially printing a partial shell before dispensing thereinto a core composition (generally a free flowing liquid, solid, or suspension), before eventually closing the partial shell by printing a closure thereupon to fully encapsulate the core composition within. In this manner, the partial shell can serve as a transient yet structurally stable open container for the core composition before it is finally closed to allow the solid dosage forms to be further manipulated and packaged without the core composition leaking. The encapsulating shell suitably also serves to preserve the chemical integrity of the core composition within.

The methods of the invention, especially where the standard 3D components comprise at least one non-powder-based printing nozzle, overcome many of the shortcomings of the powder-based 3D printing techniques of the prior art. For instance, the invention allows for the formation of strong, well-defined, high-resolution shell structures which can provide secure solid containment for powders (or indeed liquids) within. Such an approach avoids the need for long drying times which characterise inefficient powder-printing-based processes.

It will be appreciated, by those skilled in the art, that various well known methods of 3D-printing may be deployed to form a solid shell, and that indeed a mixture of such methods may be used where appropriate or beneficial. Though the present disclosure focusses on FFF/FDM methods of 3D printing (i.e. with filaments), which are effective and low cost, the principles underlying the invention are more broadly applicable.

Furthermore, the methods of the invention overcome many of the shortcomings associated with FFF-based printing of solid dosage forms. For example, the invention allows the benefits of FFF-printing to be enjoyed in the printing of the 3D-shell structure, whilst mitigating against its disadvantages through dispensing potentially-thermosensitive core materials in a fashion that does not necessitate the application of heat or the dilution of actives (e.g. in FFF filaments). As such, high-loadings of thermosensitive active ingredients can be achieved in the solids dosage forms of the invention. This also unlocks the advantages of 3D printing technologies in the realm of biopharmaceuticals, such as those comprising antibodies, polypeptides, glycopeptides, and the like.

Solid dosage forms of the invention can thus be produced "on-demand", and in an individualised and customised manner to suit the needs of particular patients, thereby avoiding certain undesirable medical compromises (e.g. patients receiving imperfect dosages due to the limited range of sizes of mass-produced dosage forms on offer). Separating the active ingredients from the 3D-structure-forming materials allows dosage forms to be made in a range of shapes and sizes because fewer limitations (such as those otherwise imparted by the presence of thermosensitive active ingredients) are imposed during the 3D-structure forming events.

The invention broadens the applicability of 3D printing to a wider range of physical forms, allowing active ingredients to reside in solid and/or liquid compositions as appropriate for the active in question.

Though chemical and physical compatibilities between the core and the shell must be considered when developing durable solid dosage forms, the detachment of the processes forming each affords better opportunities to maximise such compatibility.

It is expected that the present invention will make a significant contribution to the art in terms of the production, dispensing, and consumption of pharmaceutical products, and this will have positive health impacts for all concerned.

Solid Dosage Form Printing Apparatus and Associate Equipment and Software

The present invention provides an apparatus for preparing (or printing) a solid dosage form, suitably as defined herein. The apparatus is suitably operable to form a solid dosage form (e.g. capsule) via a combination of 3D-printing (suitably layer-by-layer), in particular to produce a 3D shell, and non-printed dispensing of active-containing materials, in particular to produce a core within the 3D shell. As such, the apparatus suitably comprises one or more printing nozzles for printing the 3D shell and one or more dispensers for dispensing core ingredients. The, or at least some of, the 3D-printing performed by apparatuses of the invention suitably involves fused filament fabrication (FFF) printing using printing filaments comprising a particular filament composition, generally containing thermoplastics. FFF printing is particularly preferred for forming the shell. Therefore suitably the apparatus employs pre-fabricated filament(s) that are selectively extruded and deposited in a layer-by-layer printing process to produce a shell. The, or at least some, of the non-printed dispensing of active-containing materials (e.g. within a core composition) suitably involves bulk dispensing of a flowable (e.g. fluid) material, suitably in a metered (i.e. precisely dosed) manner. The apparatus may suitably comprise one or more conveyors to convey relevant materials to an appropriate nozzle or dispenser.

The apparatus suitably comprises a fused filament fabrication 3-dimensional printer (an FFF 3D printer). Such printers are often referred to as fabrication deposition modelling™ (FDM) 3D printers.

The apparatus suitably comprises a build platform (or built plate) upon which the solid dosage form is printable (i.e. upon which the solid dosage form may be built). The build platform suitably provides a (substantially flat) surface which supports the solid dosage form throughout the printing process. In a particular embodiment, the build platform comprises a surface, tape layer (i.e. a layer of tape at the surface) or surface coating which promotes adhesion of the solid dosage form to the build platform during the printing process (i.e. promoting adhesion of a first layer of the solid dosage form to be printed upon the build plate, suitably after the first layer hardens upon cooling), though suitably the solid dosage form is (readily) removable from the build platform following its production.

Suitably, the apparatus comprises a computer interface (whether for wired or wireless connection to a computer operable to control the FFF 3D printer or printing apparatus).

The apparatus suitably comprises a computer for controlling the FFF 3D printer. The computer may optionally control the build platform (e.g. its position, height, etc.).

Suitably, the apparatus comprises a structural printing nozzle for printing a pre-defined three-dimensional shell onto a build platform. Such a structural printing nozzle is suitably characterised by an extrusion nozzle through and from which a filament (or part thereof) can be extruded, suitably a filament comprising a shell composition (suitably as defined herein) or a precursor thereof. Such a structural printing nozzle is suitably a part of the 3D printer.

Suitably, the apparatus comprises a non-structural dispenser. The non-structural dispenser is suitably a vessel from which a core composition, or precursor thereof, may be dispensed. In contrast to the structural printing nozzle, the non-structural dispenser suitably dispenses a core composition (or precursor thereof) in an unstructured fashion. Suitably the non-structural dispenser is configured or otherwise operable to dispense core composition (or a precursor thereof) into the 3D shell printed via the structural printing nozzle. The non-structural dispenser may be a part of the 3D printer, or may be external thereto (e.g. at another station or module within the apparatus as a whole).

The apparatus of the invention may comprise one or more other components, optionally printing or dispensing components for printing or dispensing other materials intended to form a part of the solid dosage form. For example, the solid dosage form may comprise multiple shells. The solid dosage form may comprise multiple different core compositions. The shell of the solid dosage form may comprise on its internal surface a compatibility layer comprising a substance or composition that either increases compatibility between the core and shell or otherwise maintains a (substantial) separation between the core and shell.

Structural Printing Nozzle(s)

Suitably the apparatus or 3D printer of the invention comprises one or more extrusion nozzles through and from which a filament (or part thereof) can be extruded, at least one of which is a structural printing nozzle as defined herein. References herein to nozzles and/or characteristics thereof, including optional characteristics thereof, are suitably applicable to the structural printing nozzle(s).

Suitably the or each extrusion nozzle may be a heated extrusion nozzle, suitably a heated extrusion nozzle with a variable temperature control (e.g. to allow the extrusion nozzle to be selectively heated at a desired temperature). As such, the apparatus may comprise an extrusion nozzle heating element, suitably for heating the extrusion nozzle to melt (or otherwise liquidise) the or part of the relevant filament. Suitably, the apparatus may comprise a plurality of the aforementioned extrusion nozzles, each of which may be assigned to one or more filaments. The printing apparatus may comprise one or more extrusion nozzle heating elements associated with the or each extrusion nozzle, suitably for heating the extrusion nozzle to melt (or otherwise liquidise) the or part of the relevant filament. Suitably, the apparatus may comprise a plurality of the aforementioned extrusion nozzles, each of which may be assigned to one or more filaments.

The temperature of the nozzle(s) are suitably computer-controlled. Suitably, the nozzle(s) are configured to operate at temperatures between 60 and 350° C., suitably between 80 and 300° C., more suitably between 100 and 220° C., suitably between 120 and 190° C.

Suitably each extrusion nozzle comprises an input opening (into which a filament is fed) and an output opening (out of which molten filament is deposited). The output opening is suitably smaller than the input opening. The input opening is suitably dimensioned to receive a corresponding filament therethrough. Suitably the input opening has a diameter of 1.0 to 2.5 mm, more suitably 1.5 to 2.0 mm, most preferably about 1.75 mm. The output opening is suitably dimensioned for the properties of the corresponding filament to allow molten filament to be deposited therefrom (e.g. onto a build platform). Suitably the output opening has a diameter of 50 to 400 μm, more suitably 100 to 300 μm, more suitably 150 to 250 μm, most suitably about 200 μm. In an embodiment, the nozzle has an output opening with a diameter between 200 and 500 μm.

Suitably the or each nozzle may be movable (suitably in an automated fashion or in a manner controlled by a computer or by the printer under instruction from the computer)

to extrude filament at different locations upon the build platform (or upon the partially formed solid dosage form printed thereon). The nozzle may be moveable in any or all of the X, Y, and Z direction, though in some embodiments (e.g. where the build platform is movable in the Z direction, i.e. up and down relative to the nozzle) it is constrained to move in only X and Y directions.

Suitably the or each extrude nozzle is operable to move at a speed of between 50 and 150 mm/s whilst extruding (i.e. when the nozzle is "on"—this may be the nozzle extrusion speed), more suitably between 70 and 110 mm/s, more suitably between 80 and 100 mm/s. Suitably the or each extrude nozzle is operable to move at a speed of between 100 and 200 mm/s when not extruding (i.e. when the nozzle is "off"—this may be the nozzle travelling speed), more suitably between 120 and 180 mm/s, more suitably between 140 and 160 mm/s.

It will be understood by those skilled in the art that the, each, or any nozzle may be adapted to suit the properties a corresponding filament configured to print thereto. The nozzle properties/design and filament properties/composition suitably complement one another so as to facilitate controlled extrusion of said filament (be it continuous or intermittent, e.g. where more than one filament is used in the printing of a solid dosage form), suitably without any nozzle blockages or impedance, and suitably without any unacceptable degradation of ingredients within the filament during the printing process.

Suitably, the apparatus comprises a conveyor for conveying the printing filament and any optional one or more further printing filaments to and/or through the at least one extrusion nozzle. Suitably the conveyor grips the relevant filament and feeds it through itself towards and/or through the relevant extrusion nozzle. Suitably the conveyor is controlled to deliver the relevant filament at a rate and/or at intervals suitable to provide the desired solid dosage form. The conveyor, or a part thereof (e.g. "a feeder") (preferably a part en route to the extrusion nozzle) may be heated, suitably via a heating element associated therewith, optionally a separate and/or separately controllable heating element from any heating elements associated with the extrusion nozzle. Where the apparatus comprises more than one nozzle, suitably the apparatus comprises more than one feeder, one associated with each extrusion nozzle.

Non-Structural Dispenser(s)

The apparatuses of the present invention suitably comprise one or more non-structural dispensers, most suitably one for each core composition handled by the apparatus. Suitably the non-structural dispenser(s) are operable to dispense liquids (whether or not said liquids contain particulate matter) or particulate solids.

According to an aspect of the present invention there is provided a non-structural dispenser comprising mounting elements which allow the non-structural dispenser to be mounted within an apparatus, as defined herein, or more suitably a 3D printer as defined herein. In some embodiments, the non-structural dispenser may be or comprises a core-dispensing cartridge, which cartridge is suitably preloaded with a particular core composition (or precursor thereof) intended for dispensing. As such, the non-structural dispenser may suitably comprise a core composition or a precursor thereof.

The or each non-structural dispenser suitably comprises a container, suitably a sealed or sealable container, and an outlet through which a core composition (or precursor thereof) may be dispense. Suitably the outlet is characterised by a tubular structure (e.g. needle, tube, or pipe), suitably a substantially rigid tubular structure, suitably a tubular structure having a bore size less than the maximum dimension of the solid dosage form to be produced—this allows for increased precision when dispensing.

The non-structural dispenser may comprise or be otherwise connectable to a pressurizing element. Such a pressurize element (e.g. a syringe piston) may facilitate dispensing, especially in a metered fashion. Various pressurizing elements may be used, such a plungers/pistons, screws (e.g. Archimedes crews) and such like.

The non-structural dispenser, especially an outlet thereof, may comprise or be otherwise connectable to a valve, suitably a one-way valve, which is operable (suitably electronically, suitably under the control of a computer running pursuant to appropriate software) to open and close to allow a core composition within the dispenser to be selectively dispensed. In certain embodiments, such a valve may be deployed in combination with a pressurizing element. Suitably both the valve and pressurizing element may be computer-operated to dispense a metered dose of a core composition (or precursor thereof) residing within the dispenser.

Suitably the non-structural dispenser is operable to dispense individual or multiple doses of core composition (or precursor thereof) in a metered manner. Suitably the non-structural dispenser comprises or is otherwise associated with a quantifying component for measuring a quantity of core composition (or precursor) to be dispensed. Dispensing may, for instance, be gravimetric and/or volumetric. Suitably the apparatus of the invention is operable under computer control to co-ordinate metered dispensing of each dose of core composition (or precursor thereof) with the printing of the shell(s). As such, the structural printing nozzle(s) and non-structural dispenser(s) suitably function in a coordinated and complementary manner under the control of the same computer and/or computer program. However, in some embodiments, the apparatus of the invention may conceivably comprise multiple work stations, including for example: a partial shell printing station, a core dispensing station, and a shell closure station. In such embodiments, a plurality of partial shells may be printed before being conveyed to the core dispensing station, at which point the partial shells are "filled" with core composition (or precursor thereof). Thereafter, the multiplicity of "filled" partial shells may be conveyed to a closure station which completes the solid dosage form, or at least completes the core-shell arrangement which may then proceed to further processing.

Suitably the non-structural dispenser is either unheated or is otherwise associated with a temperature control element that maintains the non-structural dispenser (and suitably also its contents) at a temperature at or below 90° C., suitably at or below 60° C., suitably at or below 50° C., suitably at or below 40° C., more suitably at or below 30° C., suitably at or above 0° C., suitably at or above 10° C. Such a temperature control element may be a thermocouple.

The non-structural dispenser may comprise insulation, such as an external insulation layer, to defend the non-structural dispenser and/or its contents against over-heating caused by neighbouring components during operation of the apparatus of the invention.

Suitable internal coatings may be deployed at the outlet of the dispenser to mitigate blocking, whether the dispenser is designed to dispense solids, liquids, or liquid-suspensions.

The non-structural dispenser may be operable to dispense solids, particular particulate solids such as powders.

The non-structural dispenser may be operable to dispense liquids, particular solutions, but also dispersions (e.g. colloidal dispersion), emulsions, and even suspensions (e.g. nanosuspensions).

In some embodiments, the non-structural dispenser may dispense a liquid core composition precursor that ultimately forms a solid or gelled core composition within the solid dosage form. Likewise, the non-structural dispenser may dispense a solid core composition precursor that ultimately forms a liquid or gelled core composition within the solid dosage form. In such embodiments, the core composition precursor suitably undergoes a chemical and/or physical transformation after (or even during) dispensing. Such a transformation may be induced in a number of ways, discussed below in relation to methods of using the present apparatus.

In some embodiments, the non-structural dispenser comprises or is otherwise associated with one or more further dispenser(s) which are operable, suitably in conjunction with the aforementioned non-structural dispenser, to cause mixing of the core composition precursor with one or more core reactants or extra core composition precursors during or following dispensation thereof. For example, one or more core composition precursors and/or reactants may be caused to pre-mix in a mixing chamber during their dispensation, or one or more composition precursors and/or reactants may be dispensed sequentially into the same target (i.e. into the same partial shell).

Solid Non-Structural Dispensers

The non-structural dispenser may be or otherwise comprise any suitable solid dispensing apparatus. Various solid dispensing apparatuses are known in the art. The core composition (or precursor thereof) for dispensing by the apparatuses of the invention may be in the form of a powder, granules, or pellets.

Suitably, the solid non-structural dispenser is a particulate solid dispenser, for example, a powder dispenser, suitably an automated powder dispenser.

Suitably the solid non-structural dispenser is operable to dispense solid(s), suitably particulate solids such as powders and granules, in a metered (i.e. metered-dose) manner. Such dispensers may be integrated with the apparatus of the invention, and in some embodiments part or all of the non-structural dispenser may be incorporated within the 3D printer itself. Various existing technologies could be viably integrated in such a manner. For example, the DisPo™ powder dispensing technology of BioDot™ (www.biodot-.com) enable the metered dispensing of solids/powers at individual doses ranging from 100 μg to 20 mg. Such a dispenser comprises a sampling cavity, to sample a metered dose (e.g. of a core composition), and a sample ejection system to dispense the sampled solid.

The solid non-structural dispenser suitably comprises a primary storage container, such as a hopper. The primary storage container suitably comprises a solid (suitably particulate) core composition or precursor thereof. The primary storage container is suitably sealed. The primary storage container may be in the form of a cartridge specially adapted for compatibility with the apparatus of the invention. The primary storage container suitably has either an outlet (such as a valve-operated tap, optionally in conjunction with a positive dispensing means, such as a pressurizer or agitator) through and from which its contents may be dispensed, or a sampling port from which contents may be extracted by an external sampling element.

The solid non-structural dispenser suitably comprises one or more dispensing vessels. Suitably such dispensing vessels are configured to receive a quantity of core composition (or precursor thereof) from the primary storage container, suitably either directly or via a conveying means. Suitably the one or more dispensing vessels may receive a pre-determined dose of core composition (or precursor thereof).

The solid non-structural dispenser suitably comprises a quantifying component, for example, a gravimetric or volumetric component. Such a quantifying component suitably weighs or otherwise quantifies each dose of solid to be dispensed. Suitably the non-structural dispenser is operable to convey a quantity of a core composition (or precursor thereof) from the primary storage container to the quantifying component or to a dispensing vessel that interacts with the quantifying component. Suitably, one or more dispensing vessels are located so that quantifying component(s) can quantify the amount of core composition received by the dispensing vessel(s). Alternatively, the quantifying component may be associated with the primary storage container and thereby measure a mass reduction as solid is dispensed therefrom. Quantification may be performed by weight and/or by volume.

The solid non-structural dispenser suitably comprises a flow-control component, which suitably controls and meters the distribution of a core composition (or precursor thereof) from the primary storage container to the one or more dispensing vessels. A flow-control component may, for example, comprise a controlled feed mechanism, and may suitably comprise an Archimedes screw, a valve, an agitator (e.g. to vibrate, tap, or shake). Alternatively or additionally, the flow-control component may comprise a sampling probe operable to sample a (estimated) quantity of a solid from the primary storage container—the sampling probe may suitably dispense solid directly into a (part-formed) solid dosage form, though preferably the sampling probe will first dispense solid into a dispensing vessel in order to accurately verify the quantity thereof to be ultimately dispensed.

The solid non-structural dispenser suitably comprises an expelling mechanism for expelling quantified amounts of core composition (or precursor thereof) from either a sampling probe or dispensing vessel. Such an expelling mechanism may suitably comprise a release means (e.g. a tap, valve, vacuum release, or other such mechanism, for example, which may tip the contents out of a dispensing vessel towards a target dispensing point). Alternatively or additionally the expelling mechanism may comprise an expulsion means, for example, a pressurizer, agitator, screw, piston or plunger, which forces a core composition (or precursor thereof) from the dispensing vessel(s) to thereby dispense the solid.

In one embodiment, the solid non-structural dispenser comprises a hopper and a moveable metering element (e.g. a shuttle plate) which is movable relative to the hopper and comprises a metered cavity/container of a fixed or adjustable size. The size of the metered cavity determines the size of each dose. The moveable metering element may be operable to receive a quantity of solid from the hopper before encapsulating a metered quantity thereof within the cavity, moving to a dispensing point, and dispensing the solid from the metered cavity.

The skilled person will be aware of certain challenges faced in the metered dispensing of solids, especially particulate solids. Forces acting in favour of outflow (e.g. gravity, pressure, and/or screw forces such as those of an Archimedes screw) are often counterbalanced by forces acting against the flow—for example: interparticle adhesion, adhesion to parts of the dispenser (e.g. walls of dispenser and/or dispensing outlet), abrasion, friction, erratic flow (e.g. creating rathole or arch profiles during funnelling), compressibility (non-compressible solids flow better), outlet restriction (e.g. the bore of the outlet), angle of repose during funnelling (angles less than or equal to 35° are preferred), external pressure (an external vacuum can assist) etc. Outflow of particles is particularly influenced by the particles themselves, in terms of particle shape, particle size, particle density, chemical nature of particles, surface roughness, and moisture content. Particle flow can be improved through judicious particle engineering, including techniques such as particle enlargement (e.g. granulation), cohesion reduction, smoothing/rounding, optimisation of moisture content, co-milling (e.g. to form flow-enhancing nanocoatings), and such like. A compressibility index less than or equal to 25%, preferably less than or equal to 15%, preferably 10%, is reassuring for better particle flow. Moreover, particle sizes greater than or equal to 10 μm, suitably greater than or equal to 50 μm, suitably greater than or equal to 100 μm, are often preferable for optimal particle flow. As such, small particle sizes, including nanoparticles (e.g. less than or equal to 100 nm), may be better dispensed in the form of suspensions, such as nanosuspensions.

Suitably the components of the solid non-structural dispenser are computer-controlled, and suitably any valves or pressurizers are electronically controlled.

In some embodiments, the solid non-structural dispenser may simply comprises a hopper with an outlet valve which is operable (preferably under computer control) to dispense a metered quantity of particulate core composition (or precursor thereof) directly from the hopper into a partial shell of the solid dosage form. Dispensation of the particulate solid may be entirely gravitational, or may be facilitate through the application of additional pressure to the hopper or within the outlet.

Suitably, a clench valve may be incorporated within a solid non-structural dispenser to control dispensation flow of particulates, such as granules.

Liquid Non-Structural Dispensers

Liquid dispensers (which suitably includes suspension, dispersion, and emulsion dispensers) are generally more straightforward then solid dispensers because they face fewer challenges.

The non-structural dispenser may be or otherwise comprise any suitable liquid dispensing apparatus. Various liquid dispensing apparatuses are known in the art. The core composition (or precursor thereof) for dispensing by the apparatuses of the invention may be in the form of a liquid, for example, a solution, dispersion, emulsion, or suspension.

Suitably, the liquid non-structural dispenser is an automated liquid dispenser.

Suitably the liquid non-structural dispenser is operable to dispense liquid(s) in a metered (i.e. metered-dose) manner. Such dispensers may be integrated with the apparatus of the invention, and in some embodiments part or all of the non-structural dispenser may be incorporated within the 3D printer itself. Various existing technologies could be viably integrated in such a manner. For example, the dispenser may comprise a syringe driver (or syringe pump), suitably an automated syringe driver. Suitably the liquid non-structural dispenser is operable under computer control to dispense a metered dose of liquid into each solid dosage form (or each partially-formed dosage form). Suitably the apparatus of the invention is operable under computer control to co-ordinate metered dispensing of each dose of core composition (or precursor thereof) with the shell fabrication process.

Though, like solids, metered dispensing of liquids can be performed in various ways, including both gravimetrically and volumetrically, preferably liquids are volumetrically dispensed.

Like with solid non-structural dispensers, the dispenser may comprises a primary storage container. However, in the case of liquids the primary storage container may be fluidly-linked directly to the ultimate dispensing outlet, as per a syringe, since precise dispensing of liquids is viable through volumetric dispensing without requiring subsequent quantitative checks.

As with solid dispensing, the liquid non-structural dispenser may comprise an outlet and optionally a pressurizing means. As such, liquid may be dispensed under gravity, vacuum or such like, and/or may be dispensed under pressure, for instance, from a piston/plunger. Suitably the components of the liquid non-structural dispenser are computer-controlled, and suitably any valves or pressurizers are electronically controlled.

Build Platform

The printing apparatus or 3D printer suitably comprises a build platform. This provides a platform upon which the solid dosage form(s) (especially shells and partial shells) may be printed.

Suitably, during printing (e.g. at the relevant printing operating temperature), the surface of the build platform onto which the solid dosage form is to be printed adheres to the solid dosage form (or at least to the layer thereof in contact with the build platform) sufficiently to prevent movement of the developing solid dosage form during printing. Suitably, however, after printing (e.g. optionally at a different temperature to the printing operating temperature) the printed solid dosage form(s) may be removed from the build platform without being damaged (e.g. the build platform is non-adherant enough to allow the solid dosage forms to be removed or is selectively tunable, e.g. by changing the operating temperature, to allow the solid dosage forms to be removed therefrom). As such, the surface of the build platform may comprise a surface coating or surface tape which imparts the required surface properties (e.g. adhesive but not too adhesive that the solid dosage forms are permanently adhered).

The build platform is suitably configured or operable to maintain a surface temperature (i.e. for the surface in contact with the solid dosage form) during printing of less than or equal to 50° C., suitably less than or equal to 40° C., suitably less than or equal to 30° C., suitably greater than or equal to 5° C., suitably greater than or equal to 15° C. In other embodiments, the build platform is operable to maintain a surface temperature of less than or equal to 150° C., suitably less than or equal to 100° C., suitably greater than or equal to 15° C. This may be achieved through selective operation of heating and/or cooling elements associated with (e.g. lying beneath) the surface of the build platform. In a particular embodiment, the build platform is operable and preferably operated to maintain a surface temperature of between 20 and 90° C., suitably between 20 and 60° C., suitably between 30 and 50° C., most suitably about 40° C.

The build platform may be movable (suitably in an automated fashion or in a manner controlled by a computer or by the printer under instruction from the computer) to control the position or height of extrusion of a relevant filament upon the build platform. The build platform may be moveable in any or all of the X, Y, and Z direction, though in some embodiments the build platform is movable in the Z direction only, i.e. up and down. Movement in the Z direction allows the gap (or height) between the nozzle and the printing point to be kept substantially constant throughout the printing process to maintain layer-by-layer consistency.

3D Printer

The 3D printer is suitably an FFF 3D printer. Conventional FFF 3D printers are well known in the art, and are generally suitable for use with the present invention, though they may be judiciously modified based on the principles outlined herein to optimise printing of solid dosage forms. For the skilled persons reference, the following research articles describe a viable operation of FFF 3D printers—S. H. Masood, "Application of fused deposition modelling in controlled drug delivery devices", *Assembly Automation,* 27/3 (2007), p.215-221 and Khaled et al, "Desktop 3D printing of controlled release pharmaceutical bilayer tablets", *International Journal of Pharmaceutics,* 461 (2014), p. 105-111—describe printing with FFF 3D printers of filaments, albeit there are no active ingredients contained within the filaments being printed (drug compounds are infused at a later stage). Furthermore, PCT publication WO2016/038356 by the present application, which is hereby incorporated by reference, also describes suitable equipment for use with the present invention.

FFF 3D printers suitable for use with the invention generally comprise a heated/heatable extruder nozzle which melts and deposits (suitably onto a build platform) molten filament in a layer-by-layer fashion. The deposited molten filament suitably hardens rapidly following deposition. Maintaining a build platform with a relatively low surface temperature may facilitate such cooling/hardening to improve the final structure of the solid dosage form being printed. The FFF 3D printer also suitably includes one or more nozzle heaters (suitably one associated with each nozzle but optionally one serving multiple nozzles) and suitably one or more conveyors (suitably one associated with each filament and/or nozzle) as defined above. Suitably the FFF 3D printer comprises one or more filament spool zones (or filament spool attachment points) for holding the relevant filament spool(s).

The FFF 3D printers of the invention may be adapted to incorporate on or more non-structural dispersers as defined herein. In such a manner, structural printing and non-structural dispensing may occur at substantially the same time.

Computer

The apparatus, including the 3D printer (and optionally the build platform), is suitably operable via the computer, suitably a computer running pursuant to specialist solid dosage form printing software, and optionally also to one or more databases, to print the solid dosage form upon the build platform, suitably via a process involving the printing and/or extrusion of an shell-forming printing filament and optionally. The computer suitably also controls and co-ordinates the dispensing of core composition(s) (or precursor(s) thereof), optionally simultaneously or sequentially with the printing of shells.

It will be readily understood by those skilled in the art that any one or more of the build platform, printing filaments, and/or computer, and/or any part thereof, may suitably be integrated within or form a part of the 3D printer. In an embodiment, the printing apparatus is essentially a 3D printer or printing apparatus.

The printing apparatus suitably includes or is otherwise connected to a computer. The printing apparatus (or 3D printer) are suitably connected to the computer via an interface (suitably a digital interface), which may be wired (e.g. a port-to-port connection via an appropriate data lead, e.g. a USB lead) or wireless. The computer may be located at the site of the relevant printing apparatus or 3D printer (i.e. a local computer). However, the invention is equally applicable where the relevant computer (or computers) is located remote from the site of the relevant printing apparatus or 3D printer, but both the printing apparatus (or 3D printer) and remote computer comprise or are otherwise connected to respective communicators allowing the remote computer and printing apparatus (or 3D printer) to communicate with one another. In this manner, a remote computer may be caused to operate the printing apparatus. In a particular embodiment, the printing apparatus (or 3D printer) may be connected to a network so that multiple remote computers (and/or local computers) may communicate therewith to cause the operation of the printing apparatus (or 3D printer).

The computer associated or otherwise connected with the printing apparatus suitably controls printing of the relevant filament(s) in accordance with a solid dosage form design and/or solid dosage form parameters (e.g. relative amounts and juxtaposition of ingredients) set forth in a given solid dosage form data file (e.g. in a CAD or a .STL file), suitably as interpreted by relevant software pursuant to which the computer runs.

In a particular embodiment, the printing apparatus comprises or is connected to a local computer, and both printing apparatus and the local computer are located on site at a pharmacy, most suitably in a purpose-build printing area or room (which may be suitably have regulatory approval).

Suitably the method and/or apparatus involves a computer running pursuant to solid dosage form printing software (and optionally one or more internal and/or external databases). Suitably, a computer running pursuant to said to solid dosage form printing software is configured to obtain information regarding one or more parameters (optionally including physical design parameters, such as shape) pertaining to the solid dosage form to be printed (e.g. be it from information inputted manually by a user or information obtained automatically from another data source). Suitably the computer pursuant to said to solid dosage form printing software is configured to request manual user input via a user interface (e.g. keyboard/screen) regarding one or more parameters pertaining to the solid dosage form to be printed. For example, a user (which may be a pharmacist acting under instruction from a patient and/or doctor) may be requested to input information regarding patient name, patient reference number (e.g. healthcare number), and/or another reference name or number, following which the computer may communicate (via relevant communicators associated therewith) with one or more databases (be it local or remote, wired or wirelessly, e.g. via a network such as the internet) to automatically call further information and/or options corresponding with said name or reference (e.g. personal patient data, medication history, repeat prescriptions, data or partial data relating to solid dosage forms to be printed, including solid dosage form data files containing designs and/or other relevant parameters). Thereafter, the user may be requested to manually input or manually select further information (e.g. drug, drug dose, release profile, etc.) and/or options to allow the computer to obtain all relevant information pertaining to the printing of the desired solid dosage form. Alternatively or additionally, the user may be requested to manually input or call information relating to one or more specific parameters pertaining to the solid dosage form (e.g. drug name/reference, drug dose, drug release requirements, colour, size, shape, solubility, packaging labelling information, etc.). Suitably, any user input may be logged and/or stored for future reference or for repeat prescriptions, etc.

There are a variety of ways the computer may be configured to obtain the relevant information to allow a solid dosage form to be printed, but it is likely that a variety of pre-set information may be used (e.g. certain approved formulations/filament combinations for producing a give solid dosage form). As such, the computer may suitably be associated with or connected/connectable with a solid dosage form database (suitably a central database accessible via a network, such as the internet) which provides all necessary pre-set information (e.g. data files relating to the solid dosage form and details of variable parameters such as drug dose levels/limits).

Suitably, a solid dosage form design for printing (and optionally parameters connected therewith) may be recorded in a solid dosage form data file, which may be read by a computer running pursuant to the solid dosage form printing software.

Suitably, a computer running pursuant to said to solid dosage form printing software is configured to calculate the mass and/or volume of the solid dosage form to be printed based on the information obtained. Suitably once the computer has obtained all required information (be it information manually inputted by a user, information imported automatically, or a combination of both) it is configured to perform calculations to allow finalisation of printing instructions before the computer controls printing. At this stage, further input may be required or requested (e.g. via a user interface), for instance dimension(s) and/or shape modifications may be optionally selected. Calculations typically relate to the mass and/or volume of a given solid dosage form required to provide a given active dosage per dosage form. Though it may be possible to increase the concentration of a given active relative to other ingredients (e.g. excipients), typically formulations are optimised and relative proportions fixed/pre-set, whereas overall mass/volume may be varied whilst retaining the same relative proportions of ingredients.

Suitably, a computer running pursuant to said to solid dosage form printing software is configured to control printing of and relative proportions of ingredients within the solid dosage form, suitably based on the information obtained and suitably based on the calculations performed. Suitably "controlling printing" includes initiating printing a terminating printing and any or all printing operations therebetween.

Suitably during printing, operational data is collected (optionally by one or more local and/or remote computers and/or databases) and suitably stored (most suitably at a central computer which may analyse such data, e.g. for quality control monitoring, monitoring of malfunctions, monitoring of batches, monitoring of dosage forms dispensed to a given patient, etc.). Suitably the printing apparatus comprises or is otherwise associated with one or more operational sensors (e.g. nozzle temperature sensors, filament feed rate sensors or conveyor sensors, overall temperature sensors, build platform sensors which may, for example, monitor surface temperature and/or rate of post-print cooling, etc.) which feedback operational parameters/information to a computer, database, or data storage facility, relating to the the operation of the printing apparatus and elements associated therewith during the printing of each dosage form. Most preferably, such operational data is collected, stored, and/or otherwise transmitted to a central computer or database to enable independent auditing of any given printing apparatus. This may be important in order to maintain quality control, and maintain appropriate records in order to retain regulatory approval of any given 3D printing system.

Suitably, a computer running pursuant to said to solid dosage form printing software is configured to control performance of one or more further processing steps.

Software and Data Files

The computer operating the printing apparatus or 3D printer suitably runs pursuant to solid dosage form printing software (and optionally also to one or more databases). As explained herein, this software may configure the computer to obtain information and perform calculations before it then configures the computer to control printing via an interface with the printing apparatus or 3D printer.

Once the computer has obtained the relevant information and performed the relevant calculation, suitably the software configures the computer to control printing of a solid dosage form, suitably based on a design (shape and dimensions, texture, layer structure, internal structure, porosity, colour (s), etc.) and/or parameters (relative amounts of ingredients, such as drug dose) relating to said solid dosage form contained within one or more solid dosage form data files. The solid dosage form data files may include a design file (e.g. containing data and/or images relating to the physical design of the solid dosage form, including its dimensions, shape, layered structure, core-shell structure, etc.) and/or a parameter file (e.g. containing data relating to the chemical composition of the solid dosage form, including drug type, excipient type(s), drug dose level, excipients to control drug release, etc.). A single solid dosage form data file may contain all data pertaining to the physical design and chemical composition. However, the physical design and chemical composition may be modified pursuant to information obtained following user input.

In some embodiments, the design file may be a CAD file depicting a solid dosage form. However, such file formats are likely to require conversion to a file format compatible with the printing apparatus or 3D printer. Conventional 3D printers generally read design files in a .STL format. As such, the design file is suitably a .STL design file depicting the solid dosage form (or at least the physical design thereof).

The design file may include or be linked with a parameter file containing chemical composition details, or the two may be independent. Alternatively there may be no parameter file as such and instead the relevant parameter information may be called from a database, for instance, in response to user input (e.g. patient reference, or drug reference, etc.).

The software may additionally configure the computer to collect, store, and/or transmit (e.g. to a central database) operational data fed back to the computer from the printing apparatus or 3D printer during printing. The software may configure the computer to detect and/or respond to any (or a preset level of) deviation in expected operational data (e.g. if nozzle temperatures exceed a maximum preset temperature level), for instance alerting the user/operator or any other interested party that a malfunction has occurred and that the solid dosage forms produced during malfunctional printing should be disposed or otherwise tested.

Databases

The apparatus and/or computer(s) associated therewith may be configured (e.g. by the solid dosage form printing software) to communicate with (suitably via relevant communicator(s), and suitably via a network such as the internet) one or more solid dosage form databases and/or patient databases to obtain information regarding one or more parameters pertaining to the solid dosage form to be printed.

For example, such database(s) may be consulted in response to a user input (e.g. patient reference number) to furnish the computer with the relevant information (or relevant information to be supplemented by further user input) to enable calculations and printing to be performed.

By way of example, a patient database comprising patient records for multiple patients (which records may include, for example, patient name, patient reference number, medical data, medical history, etc.) suitably contains information (which may merely be a cross-reference or reference number relating to information residing in another database, such as a solid dosage form database) regarding the solid dosage forms to be printed for each patient. Where the "information" is a cross-reference to a solid dosage form database, this solid dosage form database may then be consulted for further information regarding the solid dosage form. This information may be any of the information defined herein, though optionally the printing apparatus or computer(s) associate therewith may be instructed (e.g. via a user interface) to modify the information (e.g. drug dose level) prior to calculations and/or printing. Any of these database may be accessible to interested parties, preferably securely accessible (to maintain confidentiality of certain data), to enable the relevant information (be it in a patient database, solid dosage form database, or both) to be retrieved and/or amended as required (e.g. if a patient needs an increased dose in the printed solid dosage forms or a different active release profile). Suitably such database(s) may be wirelessly accessible via a network, such as the internet. Such database architectures are well known in the art.

The or each printing apparatus and/or computer(s) associated therewith may be configured (e.g. by the solid dosage form printing software) to communicate with (suitably via relevant communicator(s), and suitably via a network such as the internet) one or more apparatus-monitoring databases configured to transmit to and store within said database (and optionally analyse and/or report upon) operational data collected (optionally by one or more local and/or remote computers and/or databases) during each printing operation (i.e. each time a printing apparatus prints). As described herein, such operational data is suitably obtained/delivered by sensors associated with each given printing apparatus, suitably sensors associated with key parts of the apparatus that could affect the quality of the ultimate solid dosage forms. The operational data may be transmitted to said database in real time, following printing, or at any suitable time (e.g. at night to avoid unnecessary overloading communication networks during work hours). Such apparatus-monitoring databases may be organised with a record for each printing apparatus, and may suitably maintain a log of operational data each time said printing apparatus is operated. Suitably each set of operational data is cross-reference to a given patient a solid dosage form, suitably so that if any operational data is deemed malfunctional, the relevant interested parties can be alerted. In this manner, each printing apparatus may be monitored (whether in real time or otherwise, whether automatically or otherwise) and data periodically submitted to satisfy regulatory requirements. Moreover, central apparatus-monitoring databases may trigger a response to any perceived malfunction of a given printing apparatus. Moreover, a response may be triggered which prevents the relevant malfunctional printing apparatus from being used until its performance can be revalidated.

Again, any of the one or more apparatus-monitoring databases may be accessible to interested parties, preferably securely accessible (to maintain confidentiality of certain data), to enable the relevant information to be retrieved and/or analysed as required (e.g. if regulatory bodies wish to check that a given printing apparatus has been in good order throughout a given period, or if machine maintenance professionals which to use the data to diagnose a problem in order to restore the performance of a given printing apparatus). Suitably such database(s) may be wirelessly accessible via a network, such as the internet. Such database architectures are well known in the art.

Method of Printing Solid Dosage Form and/or Using the Apparatus

The present invention also provides a method of preparing (or printing) a solid dosage form, suitably as defined herein. Suitably this method is a method of using the aforesaid apparatus. As such, the method may suitably comprise providing a solid dosage form printing apparatus as defined herein.

The method suitably comprises operating the apparatus to produce a core-shell-based solid dosage form, suitably upon the build platform, through the 3D printing of a shell and the dispensing of a core thereinto. Suitably, such production is performed via a computer-implemented process (i.e. where printing and dispensing are controlled and suitably initiated by a computer that is connected or connectable to or within the apparatus, be it in a wired or wireless fashion).

The method suitably involves printing a three-dimensional partial shell onto a build platform. partial shell is suitably an open shell. The open shell suitably comprises a shell composition, suitably formed by the printing of a shell composition (or precursor thereof). Such printing suitably involves 3D printing, preferably FFF 3D-printing. As such, the 3D-printing may comprise printing with one or more printing filaments, wherein at least one printing filament comprises or consists of the shell composition (or precursor thereof). The shell composition (or precursor thereof) is suitably printed via the structural printing nozzle of the apparatus of the invention.

The method suitably involves dispensing a core composition (or precursor thereof) into the partial or open shell. Such dispensing suitably results in an open core-containing shell. The core composition (or precursor thereof) is suitably dispensed via the non-structural dispenser of the apparatus of the invention.

The method suitably involves closing the shell, which suitably affords a complete shell around a core. Suitably the shell is closed after the core composition (or precursor thereof) is introduced into the (partial) shell. Suitably the method involves closing the open core-containing shell, suitably by printing a closure thereupon (i.e. to cover or otherwise seal the opening of the open core-containing shell). Suitably the closure comprises a shell composition, suitably the same shell composition as the partial shell. Suitably a shell composition (or precursor thereof) is printed to form the closure. Suitably the shell composition (or precursor thereof) is printed via a structural printing nozzle, which may be the same or different to the structural printing nozzle employed to print the partial shell.

The method may include one or more further steps before, during, and/or after any of the aforesaid steps. For example, for example, the shell formed from the shell composition of the invention may be an inner or an outer shell of a multi-shell solid dosage form. As such, second and subsequent shells may be formed simultaneously with the shell of the invention. Such additional shells may be useful for tailoring the release profile of the active within the core, or may serve another purpose, such as providing an inert barrier between the principle shell and the core to mitigate any reactions therebetween. Alternatively, the internal or external surface(s) of the principle shell may be pre- or post-treated, whether through the printing of an additional layer or partial layer, or through alternative coating techniques well known in the art.

In certain embodiments the method may involve the dispensing of one or more further core composition precursors or reactants into the open shell, either before or after the principle core composition (or precursor thereof) has been dispensed thereinto. The addition of further core precursors or reactants allows reactions and transformations to take place in situ within the core. For example, a pH adjust (e.g. acid or alkali/base) may be dispensed into the open shell before or after the principle core composition (or precursor) to induce a pH change that results in a chemical or physical transformation, such as in situ gelling.

In alternative embodiments, the dispensing of additional core precursor(s) and/or reactant(s) may take place simultaneously with the dispensation of the principle core composition (or precursor), for instance multiple precursors may become mixed during printing, potentially even before reaching the interior of the open shell.

A solid dosage form produced via methods of the invention may be subsequently treated in a variety of ways to afford a further-processed solid dosage form. For instance, a solid dosage form may be enterically coated by standard enteric coating treatments known in the art. Likewise, other release-controlling properties may be imparted to a solid dosage form by further processing which, for example, provides the solid dosage form with one or more shells.

Though multi-phase printing—involving production of a partial shell, partial shell filling with a core composition, and subsequent completion (or closure) of the shell—tends to result in fewer troubleshooting issues and a higher success rate, in alternative embodiments single-phase printing may be employed, which may suitably involve interchanging printing of the shell with dispensing of the core composition. Such single-phase printing may allow for greater volumes of core composition within the shell.

Most suitably, all steps (including any further processing steps) are performed by the printing apparatus, and are suitably controlled by the same computer.

Printing an Open Shell

The printing of a three-dimensional open shell onto a build platform is suitably performed via FFF 3D-printing, suitably with one or more filaments that collectively comprise a shell composition (or precursor(s) thereof). Most suitably, a single filament comprises or consists of the shell composition (or precursor thereof). Such filament(s) are suitably printed via a structural printing nozzle as herein described.

Initially, a printing filament comprising a shell composition (or precursor thereof) suitably resides within the apparatus (or printer) in a storage position, suitably on a filament spool, suitably within a cartridge. The printing filament is suitably conveyed via one or more conveyors (e.g. rollers) to the structural printing nozzle. Printing filament is then extruded through the structural printing nozzle (suitably whilst filament continues to be conveyed towards the nozzle from a storage position). Printing through the structural printing nozzle suitably involves melting and/or softening the filament to allow it to be deposited onto the build platform, suitably in a layer-by-layer fashion. Suitably the relevant printing filament composition solidifies after being deposited onto the build platform or onto a layer that has already been printed upon the build platform. Suitably a 3D shape (in this case an open shell) is constructed in a layer-by-layer fashion through judicious depositing according to a pre-defined blueprint.

The structural printing nozzle is suitably heated at an operating temperature as herein described to facilitate melting and/or softening of a printing filament. The nozzle suitably prints filaments at one or more of the operating speeds herein described.

The structural printing nozzle is suitably moved during the printing of multiple open shells, suitably in any or all of the X, Y, Z direction.

Once printed, the open shell suitably rests on the build platform, suitably resembling a small cup. Suitably the open shell comprises an opening, suitably an opening accessible to a dispenser of a core composition (or precursor thereof). Suitably, the build platform underlies the open shell and the shell opening is at the top of the shell. As such the open shell is suitably a container. The shell suitably comprises a concave interior which may be rounded. The shell may be considered to comprise wall(s), though in practice the shell may be a single rounded continuum.

Suitably, a plurality of open shells are printed upon the build platform before any core compositions are dispensed from a non-structural dispenser.

It will be understood by those skilled in the art that the, each, or any nozzle may be adapted to suit the properties a corresponding filament configured to print thereto. The nozzle properties/design and filament properties/composition suitably complement one another so as to facilitate controlled extrusion of said filament (be it continuous or intermittent, e.g. where more than one filament is used in the printing of a solid dosage form), suitably without any nozzle blockages or impedance, and suitably without any unacceptable degradation of ingredients within the filament during the printing process.

Dispensing the Core Into the Open Shell

Following the printing of one or more (open) shells onto the build platform (suitably after a plurality of open shells has been printed thereupon), a core is suitably dispensed into the one or more shells. Suitably the core is dispensed into the or each shell by dispensing a core composition (or a precursor thereof) into the open shell, which suitably results in a core-containing open shell. The core composition (or precursor thereof) is suitably dispensed from the non-structural dispenser of the apparatus of the invention.

Suitably, the method comprises dispensing a core composition (or precursor thereof), which is a fluid composition (i.e. is suitably capable of flowing under gravity) such as a particulate solid or a liquid (including solutions, suspensions, etc.), into the or each open shell, suitably a predetermined quantity thereof.

Suitably the core composition (or precursor) is at or below a temperature of 90° C., suitably at or below 75° C., suitably at or below 60° C., suitably at or below 50° C., suitably at or below 40° C., more suitably at or below 30° C., suitably at or above 0° C., suitably at or above 10° C., during its dispensation through the non-structural dispenser.

Where the ultimate core composition (formed within the solid dosage form) is different to a core composition precursor, the method may suitably involve the dispensing of one or more core composition precursor and/or reactants. For example, a first core composition precursor and/or reactant may be first dispensed into an open shell (wherein it is contained) before a second core composition precursor and/or reactant is dispensed thereinto. In such embodiments, a chemical reaction between the core composition precursor (s) and/or reactant(s) may change the overall composition.

Such a chemical reaction may even change the physical form of the composition—the resulting core composition may be a solid, liquid, or even a gel. In an embodiment, one of the core composition precursor(s) may be an active-containing core precursor, whilst another of the core composition precursor(s) may be a pH adjuster (e.g. comprising an acid, base, and/or buffer) which changes the pH of the active-containing core precursor to cause either or both a chemical and/or physical change. In a particular embodiment, the active-containing core precursor may be dispensed as a liquid but may be transformed to a solid or gelled core composition.

In some embodiments, the aforementioned mixing of core composition precursor(s) and/or reactant(s) may occur during dispensation (or even before if a chemical reaction is slow enough not to compromise dispensing) in a mixing chamber. For example, the dispensing of the core composition may involve dispensing two or more core composition precursor(s) and/or reactant(s) into a mixing chamber before being ultimately being dispensed into the open shell(s). In this manner, more homogeneity may be achieved in the overall core composition. The mixing chamber may need to be sufficiently small to avoid accumulation of blocking materials.

In preferred embodiments, the core composition in the final solid dosage form is the same as the core composition dispensed from the apparatus of the invention and no modifications of the composition ensue. As such, the core suitably comprises the core composition as per that dispensed from the non-structural dispenser.

The method suitably comprises dispensing individual doses of a core composition (within each open shell) which comprise between 0.1 μg and 1000 mg of active ingredient per individual dose, suitably between 1 μg and 500 mg, suitably between 10 μg 50 mg, suitably between 100 μg and 10 mg.

Where the core composition (or precursor thereof) to be dispensed is a particulate solid, dispensing thereof suitably comprises sampling of said solid from a primary storage container (which may be performed by extracting particulate solid from said storage container with a sampling probe or such like, or by receiving particulate solid expelled from said storage container into a vessel), suitably in a quantitative manner. Suitably the sampled particulate solid is quantified (suitably in addition to any preliminary quantification during sampling), suitably gravimetrically. Individual dose (s) of quantified particulate solid are then suitably dispensed into an open shell(s), suitably in a forced manner (e.g. using pressure to push the solid, or reduced pressure to pull the solid).

In contrast to the printing of the shell, which is characterised by a multiplicity of printed layers, the core is suitably dispensed en masse or as a bulk (i.e. as a single volume or mass directed to the same target location). Suitably upon printing the core composition (or precursor thereof) collapses and spreads to the dimensions of the open shell due to its relative fluidity. The open shell acts as a container to facilitate the methods of the invention.

Where the core composition (or precursor thereof) to be dispensed is a liquid, suitably said liquid is dispensed in a volumetric manner, suitably via a syringe or syringe driver.

Closing the Shell to Encapsulate the Core

Suitably a "filled" open shell (core-containing open shell) is closed by printing a printing composition (e.g. using a filament, where FFF 3D-printing is employed) through a structural printing nozzle as defined herein onto the "filled" open shell. The printing composition employed for closing the shell may be the same or different to the shell composition (or precursor) used for printing the open shell, though most preferably it is the same and is printed via the same printing nozzle (or similar or identical printing nozzle at another station within the overall apparatus). Most suitably, the open shell is closed using the same printing methods described above in relation to the printing of the open shell.

Computer-Implementation of Method

The method of preparing a solid dosage form is suitably a computer-implemented method, suitably as defined herein.

The method suitably involves providing a solid dosage form printing apparatus, suitably as defined herein, and operating said apparatus to print the solid dosage form. Suitably the apparatus includes or is otherwise connected to a computer. Operating the apparatus suitably involves operating a computer, which is suitably connected (be it in a wired or wireless fashion) with or within the relevant printing apparatus (so as to allow the computer to control and co-ordinate other parts of the apparatus, suitably including an FFF 3D printer), to cause printing of a solid dosage form.

A computer that is comprised of or otherwise associated with an apparatus of the invention may be suitably referred to as a printing control computer (or printing computer). The printing control computer may serve a different function (and may be a distinct entity) to other "computers" referred to herein, such as monitoring computers and analytical computers, though a single computer may perform the function(s) of one or more of any combination of these computers. A printing control computer suitably controls both the printing of a shell composition (or precursor) through a structural printing nozzle and the dispensing of a core composition (or precursor) through a non-structural dispenser. Wherever a different computer is used to implement each of these operations, said computers are suitably coordinated and may thus be considered to be a part of one overall computer.

Printing of solid dosage forms is suitably controlled by a computer, running pursuant to solid dosage form printing software, suitably based on information provided to the computer by user input(s) (drug type, drug dose level), databases (e.g. patient database and/or solid dosage form databases), and/or data files (e.g. design and/or parameter files), as described herein. Suitably an FFF 3D printer is configured to print pursuant to instructions provided by the computer by: feeding filament(s) to and through their respective nozzle(s) at the appropriate intervals and/or at the appropriate rates; heating the relevant nozzle(s) at the appropriate temperature(s) for the appropriate time; and by moving the nozzle(s) and/or build platform to enable systematic layer-by-layer printing in accordance with the relevant information obtained and calculations made by the computer. Such printing is suitably also coordinated with the dispensing of a core composition (or precursors), which is likewise controlled based on information provided to the computer by use input(s), databases, etc. This includes coordinating the quantities being dispensed, in line with the volume of the relevant printed shells, as well as timing of such dispensing—which can only occur after the structural foundations (e.g. open shells) have been printed.

The feeding of filament(s) to and through their respective nozzle(s) is suitably facilitated by a conveyor (or roller) as described elsewhere herein. Such a conveyor is suitably situated along a filament flow path of a given filament, suitably between a filament source (e.g. a filament spool or cartridge) and an extrusion nozzle to and through which the given filament is assigned to flow.

The extrusion nozzle(s) (including structural printing nozzle(s)) are suitably controlled by the computer according to the "obtained information" regarding the solid dosage form (e.g. design and/or other parameters). Nozzles are suitably controlled to extrude a given filament upon a build platform (or upon a partially build solid dosage form upon the build platform) to a pattern pre-defined by the "obtained information". As such, the or each nozzle may be controlled to switch "on" and "off" in accordance with a pre-defined schedule to deliver the required pattern in the construction of the solid dosage form. A nozzle may be switched "on" by causing an output opening to open, by adjusting the nozzle's operating temperature (e.g. increasing it so as to cause melting of the relevant filament), by operating the a conveyor to feed filament through the nozzle, or a combination of any or all of the aforementioned. Naturally, a nozzle may be switched off by causing an output opening to close, by adjusting the nozzle's operating temperature (e.g. decreasing it to a temperature which does not cause melting of the relevant filament), by operating the a conveyor to restrict or cease feeding of a filament through the nozzle, or a combination of any or all of the aforementioned. The temperature of the nozzle(s) are suitably set and controlled by the computer according to the properties of the filament in question, as described elsewhere herein. Suitably, the operating temperature of an extrusion nozzle through which a printing filament passes is between 90 and 220° C., more suitably between 120 and 190° C., suitably between 165 and 190° C., suitably between 140 and 170° C. Suitably, the operating temperature of an extrusion nozzle through which a printing filament is between 80 and 300° C., more suitably between 100 and 220° C., suitably between 120 and 190° C. However, the operating temperature of an extrusion nozzle may be as low as 65° C., especially in systems that employ low-melting polymers (e.g. PEG) or polymers with low glass transition temperatures. Most suitably, the extrusion nozzle temperature is set to at least 70° C. In a particular embodiment, the nozzle temperature is 110-160° C., suitably 110-130° C., suitably 130-150° C., suitably 135-145° C. Suitably the operating temperature of an extrusion nozzle assigned to a given filament is higher than any corresponding hotmelt extrusion temperatures used in the formation (i.e. via extrusion) of the given filament, suitably between 30 and 90° C. higher, more suitably between 50 and 70° C. higher.

The non-structural dispenser(s) are suitably controlled by the computer according to the "obtained information" regarding the solid dosage form (e.g. design and/or other parameters). As such, the or each non-structural dispenser may be controlled to switch "on" and "off" in accordance with a pre-defined schedule to deliver the required amounts to the relevant open shells of the solid dosage form during their construction. A non-structural dispenser may be switched "on" by activated dispensing mechanisms, which may suitably involve sampling and/or dispensing depending on whether solids or liquids are being dispensed. Naturally, a non-structural dispenser may be switched "off" by deactivated the aforesaid mechanism(s). The temperature of the core composition (or precursors) are suitably set and controlled by the computer according to the properties of the core composition (or precursor) in question, as described elsewhere herein. Suitably, the operating temperature of a non-structural dispenser is as hereinbefore described. Most suitably there is no significant heating of the non-structural dispenser or any of its components, since lower temperatures are preferable to discourage and degradation of active ingredient(s) residing within the core composition (or precursors thereof).

The build platform is suitably controlled by the computer according to the "obtained information" regarding the solid dosage form (e.g. design and/or other parameters), suitably as described elsewhere herein. This may include controlling the operating temperature of the build platform, in particular the operating temperature of the surface of the build platform. Suitably, during printing, the operating temperature of the build platform or surface thereof is maintained substantially constant, suitably at a constant temperature +/−5° C. Such temperature control may facilitate cooling and/or hardening of post-deposited molten filament(s) to thereby secure the structural integrity of the solid dosage form as it is being printed. Such temperature control may facilitate adhesion of the developing solid dosage form to the surface of the build platform during printing. Such temperature control may facilitate release (i.e. unsticking) of a solid dosage form after printing (e.g. the surface of the build platform may be heated or cooled, as appropriate, to reduce adhesion of the solid dosage form(s) thereto). During printing, the build platform is suitably configured or operable to maintain a surface temperature (i.e. for the surface in contact with the solid dosage form) of less than or equal to 50° C., suitably less than or equal to 40° C., suitably less than or equal to 30° C., suitably greater than or equal to 5° C., suitably greater than or equal to 15° C.

Solid Dosage Form

The present invention provides a solid dosage form. The solid dosage form may be a solid dosage form obtainable by, obtained by, or directly obtained by the method for preparing a solid dosage form as defined herein.

In a particular embodiment, the solid dosage form is a pharmaceutical dosage form.

The solid dosage form suitably comprises a core. The core suitably comprises a core composition. The core composition suitably comprises an active ingredient, suitably a pharmaceutically, nutraceutically, or food-supplement active ingredient. Most suitably the active ingredient is a pharmaceutically active ingredient. The core is suitably dispensed, preferably at relatively low temperatures (as described herein in relation to operating temperatures of non-structural dispensers), and is therefore suitably non-printed (e.g. not printed via a 3D-printing nozzle). The core composition (suitably a solid, liquid, or gel) is suitably contained within a shell.

The solid dosage form suitably comprises a shell, suitably a three-dimensional shell. The shell suitably surrounds the core. The shell suitably comprises a shell composition. The shell is suitably printed (e.g. printed via a 3D-printing nozzle), suitably at relatively high temperatures (as described herein in relation to operating temperatures of structural printing nozzles). The shell composition suitably comprises (or is formed from) a 3D printing composition (e.g. a fused filament fabrication composition), wherein the shell composition is suitably (structurally) solid.

In a particular embodiment, the solid dosage form is a capsule. Suitably the capsule's shape is defined by the shell. Suitably the capsule contains a core composition as defined herein.

Suitably the core and shell are mutually compatible, and are suitably physically and chemically inert to each other. For example, suitably a liquid (or indeed solid) core does not substantially dissolve or disintegrate the shell or any component(s) thereof (especially not within 14 days, suitably not within 30 days, suitably not within 12 months), and vice versa. Furthermore, suitably the core does not undergo a chemical reaction with the shell (especially not within 14 days, suitably not within 30 days, suitably not within 12 months). As such, suitably each of the core and shell are substantially stable in the solid dosage form. Suitably the solid dosage form remains pharmaceutically acceptable and/or viable for at least 14 days after its manufacture, suitably for at least 30 days, suitably for at least 12 months.

Suitably the core is physically detached from the shell. Suitably, the core (or part thereof) is physically movable relative to the shell, or at least would be moveable in the presence of free internal space. For instance, in the case of a liquid, the liquid is suitably free to move within the shell upon agitation of the solid dosage form; and in the case of a particulate solid, the particles are suitably free to move within the shell upon agitation of the solid dosage form. In some cases, audible sloshing (for liquid cores) or rattling (for solid cores) may be heard upon agitating the solid dosage form.

The core is suitably discernible from the shell (e.g. if a cross-section of the solid dosage form is taken) on the basis that the shell has a layered structure (by virtue of the 3D printing mechanism which prints layer-by-layer) and the core has a non-layered structure (by virtue of the core having been dispensed en masse into the shell).

The solid dosage form(s) of the invention are suitably for oral administration. Most suitably the solid dosage form is a capsule, most suitably a pharmaceutical capsule.

The solid dosage form(s) of the invention may be immediate release dosage forms, delayed release dosage forms (e.g. with enteric coatings or shells), or sustained release dosage forms. The release profile of the solid dosage form may depend on the shell, the core, or any additional shells (e.g. surrounding the primary shell characterised by the shell composition as defined herein). If the core comprises microcapsules or coated granules, such coatings may influence the release profiles. Most suitably, however, the shell is tailored to influence the active-release profile.

The longest dimension ($D_{max}$) of the solid dosage form (e.g. whether in the X, Y, or Z direction) is suitably greater than or equal to 3 mm, suitably greater than or equal to 5 mm, suitably greater than or equal to 8 mm, suitably greater than or equal to 10 mm, suitably greater than or equal to 12 mm. The longest dimension of the solid dosage form is suitably less than or equal to 30 mm, suitably less than or equal to 25 mm, suitably less than or equal to 20 mm, suitably less than or equal to 15 mm.

The shortest dimension ($D_{min}$) of the solid dosage form (i.e. not necessarily the thinnest part but the maximum length of the thinnest dimension, or the shortest of the X, Y, or Z) is suitably greater than or equal to 1 mm, suitably greater than or equal to 3 mm, suitably greater than or equal to 5 mm, suitably greater than or equal to 8 mm, suitably greater than or equal to 10 mm, suitably greater than or equal to 12 mm. The shortest dimension of the solid dosage form is suitably less than or equal to 30 mm, suitably less than or equal to 25 mm, suitably less than or equal to 20 mm, suitably less than or equal to 15 mm, suitably less than or equal to 10 mm, suitably less than or equal to 8 mm.

The volume of the solid dosage form ($V_{sdf}$, suitably in terms of space bounded by the shell, suitably up to and including the outer shell surface) is suitably greater than or equal to 3 $mm^3$, suitably greater than or equal to 5 $mm^3$, suitably greater than or equal to 10 $mm^3$, suitably greater than or equal to 50 $mm^3$, suitably greater than or equal to 100 $mm^3$, suitably greater than or equal to 200 $mm^3$. The volume of the solid dosage form is suitably less than or equal to 500 $mm^3$, suitably less than or equal to 300 $mm^3$, suitably less than or equal to 250 $mm^3$, suitably less than or equal to 150 $mm^3$, suitably less than or equal to 50 $mm^3$.

The solid dosage forms of the invention are advantageously customisable in terms of the type/nature of active ingredient dose, the dose of the active ingredient within the solid dosage form (be it an absolute dose per solid dosage form or the concentration of the active within the dosage form), the mass/volume of the solid dosage form (which is typically adaptable to vary the absolute dose of the active without changing the concentration of the active within the dosage form), the active release profile (which may be varied through judicious use and/or distribution of appropriate excipients, e.g. core-shell arrangements for delayed or sustained release), or shape and appearance (including novelty shapes, colours, and patterns, such as those that may help encourage medication compliance for particular patients).

Many of the features preferred of the solid dosage form are described elsewhere herein. For instance, features described in relation to the method of producing the solid dosage form may suitably reflect a feature of the solid dosage form itself (e.g. layer height). Suitably the solid dosage form comprises ingredients provided by the filament(s) used in its formation (e.g. in the shell), and may be considered to comprise relevant filament compositions.

The shell of the solid dosage form has an average thickness suitably greater than or equal to 1 μm, suitably greater than or equal to 10 μm, suitably greater than or equal to 100 μm, suitably greater than or equal to 500 μm, suitably greater than or equal to 1 mm. The shell of the solid dosage form has an average thickness suitably less than or equal to 5 mm, suitably less than or equal to 2 mm, suitably less than or equal to 1 mm, suitably less than or equal to 600 μm.

Suitably, solid dosage forms of the invention comprise greater than or equal to 0.5 wt % active ingredient, suitably greater than or equal to 1 wt % active ingredient, suitably greater than or equal to 5 wt % active ingredient, suitably greater than or equal to 9 wt % active ingredient, suitably greater than or equal to 19 wt %, suitably greater than or equal to 39 wt %. Suitably, solid dosage forms of the invention comprise less than or equal to 60 wt % active ingredient, suitably less than or equal to 50 wt % active ingredient, suitably less than or equal to 30 wt % active ingredient. Suitably, after the active ingredient, the weight balance of solid dosage form consists essentially of carrier(s), diluent(s), and/or excipient(s) (all of which may be deemed to constitute "excipients").

Suitably the core constitutes greater than or equal to 1 wt % of the solid dosage form as a whole, suitably greater than or equal to 3 wt %, suitably greater than or equal to 5 wt %, suitably greater than or equal to 10 wt %, suitably greater than or equal to 20 wt %, suitably greater than or equal to 50 wt %, suitably greater than or equal to 60 wt %. Suitably the core constitutes less than or equal to 70 wt % of the solid dosage form as a whole, suitably less than or equal to 55 wt %, suitably less than or equal to 25 wt %, suitably less than or equal to 15 wt %, suitably less than or equal to 5 wt %. The shell may suitably comprise less weight than the core within the solid dosage form.

Suitably the core of the or each solid dosage form has a weight of greater than or equal to 1 mg, suitably greater than or equal to 5 mg, suitably greater than or equal to 10 mg, suitably greater than or equal to 50 mg, suitably greater than or equal to 80 mg. Suitably the core of the or each solid dosage form has a weight of less than or equal to 1000 mg, suitably less than or equal to 500 mg, suitably less than or equal to 250 mg, suitably less than or equal to 100 mg.

Suitably the volume of the core ($V_{core}$) constitutes greater than or equal to 0.1% of the overall volume of the solid dosage form ($V_{sdf}$), suitably greater than or equal to 1%, suitably greater than or equal to 2%, suitably greater than or equal to 4%. Suitably the volume of the core ($V_{core}$) constitutes less than or equal to 50% of the overall volume of the solid dosage form ($V_{sdf}$), suitably less than or equal to 20%, suitably less than or equal to 10%, suitably less than or equal to 6%.

Suitably the volume of empty space ($V_{empty}$—i.e. excluding the shell and core) constitutes greater than or equal to 0.1% of the overall volume of the solid dosage form ($V_{sdf}$), suitably greater than or equal to 1%, suitably greater than or equal to 10%, suitably greater than or equal to 20%, suitably greater than or equal to 50%.

Shell, Shell Composition, Shell Filament and Shell Filament Composition

The shell suitably is or comprises a shell composition (i.e. shaped as a shell). The shell is suitably solid. The composition of the shell is suitably (substantially) the same as that of the material printed from the structural printing nozzle. The shell is suitably formed from a shell printing filament (e.g. an FDM or FFF filament), and thus the shell suitably is or comprises a shell filament composition, suitably an FFF filament composition. Suitably, the composition of the shell is (substantially) the same as the composition of the shell filament. As such, any definitions herein relating to the composition of the shell filament (e.g. shell filament composition) may be equally applicable to the composition of the shell per se (e.g. shell composition), even for embodiments where the shell is printed by a technique other than a filament printing technique. However, the shell composition may be considered a printed shell filament composition as defined herein, since in some cases (e.g. where a degree of chemical change occurs within the shell composition during printing) the process of printing can better describe the product.

Though a shell may be a continuous or shape, the shell may be considered to comprise a open shell and a closure (or a base shell and a lid). The overall dimensions of the solid dosage form are suitably defined entirely by the shell.

The shell composition suitably comprises one or more shell polymers, suitably pharmaceutical acceptable polymers (or GRAS approved polymers). The shell composition may comprise one or more thermoplastics. The shell composition may comprise one or more pharmaceutically acceptable polymers selected from the group consisting of: (alkyl-)polyacrylates, silicones, polyurethanes, polyolefins (e.g. polystyrene), polyalkylene glycols, polyvinyl alcohols, polyamides, acrylonitrile butadiene styrene (ABS), polylactic acid (PLA), polyglycolide, nylon, and/or co-polymers or mixtures thereof. The list is by no means exhaustive.

The shell filament (used in printing of shells) and shell filament composition may be exactly as described in paragraphs [00331] to [00340] of WO2016/038356 (by the present applicant), which is incorporated herein by reference. Such shell filament compositions may comprise one or more of: shell polymers identical to those set forth in paragraph [00289] to [00302], fillers as set forth in paragraph [00303] to [00304], plasticizers as set forth in paragraph [00305] to [00312], and other ingredients as explained in paragraph [00313] to [00317] WO2016/038356. Moreover, the shell filament and shell filament composition may be characterised as set forth in paragraph [00244] to [00270] to the extent that these paragraphs are applicable to the "further filament compositions" described in paragraph [00331] to [00340] WO2016/038356.

The shell filament, shell filament composition, and ultimate shell composition suitably comprise a meltable component. The shell composition may also comprise a non-meltable component to mitigate nozzle blockages. Suitably, the "meltable" component is a component that melts (or undergoes a glass transition to thereby soften) at the designated operating temperature of any corresponding 3D printer extrusion nozzle configured to process said filament, whereas the "non-meltable" component is suitably a component that does not melt (or undergo a glass transition) at the same temperature. Suitably, the "meltable" component may be a mixture of components, which collectively melt or undergo glass transitions together as a mixture—e.g. shell polymer and plasticizers. However, "non-meltable" components are more likely to be individual components with different melting points or glass transition temperatures. Suitably the meltable component has a melting point (or $T_g$) at or below 220° C., suitably at or below 150° C., suitably at or below 100° C., suitably at or below 80° C., suitably at or below 60° C. Suitably the meltable component has a melting point (or $T_g$—i.e. at least one $T_g$) greater than or equal to 20° C., suitably greater than or equal to 30° C., suitably between 30 and 65° C., suitably between 30 and 35° C. Suitably, the non-meltable component has a melting point (or $T_g$) at or above 150° C., suitably at or above 200° C., suitably at or above 500° C., suitably at or above 1000° C.

As explained above, references to "meltable" and "non-meltable" components encompasses "softenable" and "non-softenable" components respectively, where instead of "melting" at a particular temperature the component "softens". As such, references in this context to a melting point may additionally or alternatively relate to a glass transition temperature. Such glass transitions are particularly applicable to thermoplastic component(s). As such, a "meltable" component may be a thermoplastic component, suitably who glass transition temperature (temperature at which the thermoplastic component softens rather than melts) is lower than the temperature to which said component is exposed (e.g. during printing).

Each of the various filament ingredients described herein are suitably either a meltable or a non-meltable component (not both). For instance, a shell polymer is suitably a meltable component and is suitably selected to undergo melting or a glass transition during printing. A filler (e.g. calcium tribasic phosphate, talc, etc.), by contrast, is suitably a non-meltable component and is suitably selected so as to remain solid during printing. Notwithstanding the contrasting melting/glass-transition properties of the various ingredients, suitably the filament itself has a characteristic glass transition temperature. Suitably this characteristic glass transition temperature is measurable using the well-known techniques described herein and elsewhere, and is a consequence of the combination of ingredients. Various concentration (wt %) ratios of meltable:non-meltable components may afford viable filaments for 3D printing. Suitably the ratio of meltable:non-meltable components is between 1:10 and 10:1, more suitably between 3:7 and 7:3, suitably between 4:6 and 6:4, where suitably the meltable component(s) collectively include all relevant meltable components (e.g. shell polymers, plasticizers, etc.) and the non-meltable component(s) include all relevant non-meltable components (e.g. filler(s), lubricants, etc.).

The shell filament is suitably sufficiently stiff to enable it to be viably fed (at a consistent rate) to and through a corresponding extrusion nozzle within the printing apparatus or 3D printer. The active shell filament is suitably sufficiently stiff to avoid the filament becoming stretched during printing. However, the filament is suitably not so stiff that the nozzle operating temperature required to extrude the filament will degrade the contents of the ingredient (e.g. causing a change in composition of greater than or equal to 1 wt %).

The shell filament is suitably sufficiently flexible and/or soft to enable it to be extruded (at a consistent rate) from a corresponding extrusion nozzle within the printing apparatus or 3D printer. The shell filament is suitably sufficiently flexible and/or soft to allow the filament to be viably spooled/coiled around a filament spool.

The shell filament is suitably neither too brittle (and breakable during printing/spooling) nor too flexible (precluding its viable conveyance through the printing apparatus or 3D printer). The shell filament composition and dimensions (e.g. thickness) of the filament can be judiciously altered, using the principles taught in the present disclosure, to obtain an optimal filament structure.

The shell filament suitably has a thickness (i.e. diameter or maximum thickness) of between 0.1 mm and 5 mm, suitably between 0.5 mm and 4 mm, more suitably between 1 mm and 3 mm, most suitably between 1.5 mm and 2 mm. In a particular embodiment, the shell filament has a thickness of about 1.75 mm. However, the filament thickness may be adjusted to suit the extrusion nozzles (in particular the size/diameter of the respective openings thereof) through which they are to be extruded.

Suitably, the shell filament is capable of being coiled (or spooled) around a spool, suitably a spool having a hub diameter of about 20 cm, suitably a hub diameter of about 10 cm, suitably about 5 cm, suitably about 2.5 cm, suitably about 1 cm, suitably without breaking and/or stretching.

The shell filament suitably has a glass transition temperature ($T_g$) between 20 and 200° C., suitably between 45° C. and 165° C., or suitably between −10° C. and 165° C.

Suitably, the shell filament is judiciously tailored with appropriate proportions and types of ingredients to produce filaments with a desired $T_g$ and/or melting point to minimise the corresponding nozzle operating temperature required for extrusion.

The shell filament (and hence the shell composition) suitably comprises a shell polymer. The shell polymer is suitably a meltable component or otherwise has the properties defined herein in relation to a meltable component. The shell filament optionally comprises a plasticizer. The shell filament optionally comprises a filler, where suitably said filler is a non-meltable component or otherwise has the properties defined herein in relation to a non-meltable component. In a particular embodiment, the shell filament comprises a shell polymer and a plasticizer. In a particular embodiment, the shell filament comprises a shell polymer and a filler (suitably that is non-meltable as defined herein). In a particular embodiment, the shell filament comprises a shell polymer, a plasticizer, and a filler.

Suitably, the shell filament of the invention comprises greater than or equal to 10 wt % shell polymer(s) (suitably excluding any plasticizer(s)), suitably greater than or equal to 20 wt %, suitably greater than or equal to 30 wt %, suitably greater than 50 wt %, suitably greater than or equal to 70 wt %, suitably greater than or equal to 79 wt %. Suitably, the shell filament of the invention comprises less than or equal to 99 wt % shell polymer(s) (suitably excluding any plasticizer(s)), suitably less than or equal to 95 wt %, suitably less than or equal to 90% wt, suitably less than or equal to 80 wt %, suitably less than or equal to 60 wt %.

Suitably, the shell filament of the invention comprises greater than or equal to 0.1 wt % plasticizer(s), suitably greater than or equal to 1 wt %, suitably greater than or equal to 3 wt %, suitably greater than or equal to 4 wt %, suitably greater than 9 wt %, suitably greater than or equal to 15 wt %. Suitably, the shell filament of the invention comprises less than or equal to 50 wt % plasticizer(s), suitably less than or equal to 40 wt %, suitably less than or equal to 30 wt %, suitably less than or equal to 20 wt %, suitably less than or equal to 11 wt %.

Suitably, the shell filament of the invention comprises greater than or equal to 1 wt % filler(s), suitably greater than or equal to 5 wt %, suitably greater than or equal to 10 wt %, suitably greater than 20 wt %, suitably greater than or equal to 30 wt %. Suitably, the shell filament of the invention comprises less than or equal to 70 wt % filler(s), suitably less than or equal to 60 wt %, suitably less than or equal to 50 wt %, suitably less than or equal to 40 wt %, suitably less than or equal to 35 wt %.

In a particular embodiment, the shell filament (and thus the shell composition and/or shell filament composition) comprises or consists of:

10 to 90 wt % shell polymer(s);
and optionally:
1 to 30 wt % plasticizer(s); and/or
1 to 60 wt % filler(s).

In a particular embodiment, the shell filament (and thus the shell composition and/or shell filament composition) comprises or consists of:

30 to 80 wt % shell polymer(s);
and optionally:
5 to 20 wt % plasticizer(s); and/or
10 to 50 wt % filler(s).

In a particular embodiment, the shell filament (and thus the shell composition and/or shell filament composition) comprises or consists of:

40 to 60 wt % shell polymer(s);
and optionally:
10 to 20 wt % plasticizer(s); and/or
30 to 40 wt % filler(s).

In a particular embodiment, the shell filament (and thus the shell composition and/or shell filament composition) comprises or consists of:

40 to 60 wt % shell polymer(s);
10 to 20 wt % plasticizer(s); and
30 to 40 wt % filler(s).

Shell Polymer(s)

Any suitable polymer(s) may be used.

The melting point (or glass transition temperature) of the shell polymer is suitably less than the active ingredient, suitably by at least 20° C., more suitably by at least 40° C., more suitably by at least 50° C. The shell polymer suitably has a melting point between 140 and 250° C., more suitably between 150 and 200° C., most suitably between 155 and 175° C.

Suitably the shell polymer has a specific heat of between 0.1 and 1 cal/g° C., most suitably between 0.3 and 0.5.

The shell polymer suitably has a density between 1.1 and 1.6 g/mL, most suitably between 1.2 and 1.4.

The shell polymer suitably has a glass transition temperature lower than the melting point of the active ingredient, suitably at least 20° C. lower, more suitably at least 40° C. lower, more suitably at least 50° C. lower.

The shell polymer(s), especially where an immediate release solid dosage form is desired, is suitably selected from a polymer (suitably a cationic polymer or neutral polymer or copolymer) having a viscosity of no more than 50 mPa·s, suitably no more than 30 mPa·s, suitably no more than 10 mPa·s, though suitably having a viscosity of at least 1 mPa·s—most suitably a viscosity between 2 and 8 mPa·s. The shell polymer(s), especially where an immediate release solid dosage form is desired, is suitably selected from a polymer having a molecular weight of at least 20,000 g/mol, more suitably at least 35,000, more suitably at least 45,000, though suitably less than 1,000,000 g/mol, more suitably less than 100,000 g/mol—most suitably a molecular weight between 35,000 and 65,000 g/mol. The shell polymer(s), especially where an immediate release solid dosage form is desired, is suitably selected from a polymer having a glass transition temperature (Tg) of at most 100° C., suitably at most 80° C., suitably at most 50° C., though suitably at least −10° C., more suitably at least 35° C.—most suitably a Tg between 30 and 60° C. In some embodiments, the shell polymer(s) may not have a glass transition temperature as such, though observed softening may still occur. The shell polymer(s), especially where an immediate release solid dosage form is desired, is suitably an (optionally alkyl-, suitably methyl- or ethyl-) acrylate, methacrylate and/or ethacrylate copolymer (suitably comprising amine-containing monomeric units) suitably having a viscosity between 2 and 8 mPa, suitably having a molecular weight between 35,000 and 65,000 g/mol, and/or suitably having a Tg between 30 and 60° C. In a particular embodiment, the relevant copolymer is poly(butyl methacrylate-co-(2-demethylaminoeethyl) methacrylate-co-methyl methacrylate), suitably in a respective monomeric molar ratio of 1:2:1 (+/−5% for each molar value of the ratio). The shell polymer is suitably Eudragit E.

The shell polymer(s), especially where an extended release solid dosage form is desired, is suitably selected from a polymer having a viscosity of no more than 30 mPa·s, suitably no more than 20 mPa·s, suitably no more than 16 mPa·s, though suitably having a viscosity of at least 1 mPa·s—most suitably a viscosity between 1 and 15 mPa·s. The shell polymer(s), especially where an extended release solid dosage form is desired, is suitably selected from a polymer having a molecular weight of at least 10,000 g/mol, more suitably at least 250000, more suitably at least 30,000, though suitably less than 100,000 g/mol, more suitably less than 40,000 g/mol—most suitably a molecular weight between 29,000 and 35,000 g/mol. The shell polymer(s), especially where an extended release solid dosage form is desired, is suitably selected from a polymer having a glass transition temperature (Tg) of at most 100° C., suitably at most 80° C., suitably at most 70° C., though suitably at least 40° C., more suitably at least 50° C.—most suitably a Tg between 55 and 70° C. In some embodiments, the shell polymer(s) may not have a glass transition temperature as such, though observed softening may still occur. The shell polymer(s), especially where an extended release solid dosage form is desired, is suitably an (optionally alkyl-, suitably methyl- or ethyl-) acrylate, methacrylate and/or ethacrylate copolymer (suitably comprising amine-containing monomeric units) suitably having a viscosity between 1 and 15 mPa, suitably having a molecular weight between between 29,000 and 35,000 g/mol, and/or suitably having a Tg between 55 and 70° C. In a particular embodiment, the relevant copolymer is poly(ethyl acrylate-co-methyl methacrylate-co-trimethylammonioethyl methacrylate chloride), suitably in a respective monomeric molar ratio of 1:2:0.2 (+/−5% for each molar value of the ratio). The shell polymer is suitably Eudragit RL.

The shell polymer(s), especially where a delayed release solid dosage form is desired, is suitably selected from a polymer having a viscosity of at least 20 mPa·s, suitably at least 40 mPa·s, suitably at least 50 mPa·s, though suitably having a viscosity of no more tan 300 mPa·s, suitably no more than 210 mPa·s—most suitably a viscosity between 40 and 210 mPa·s. The shell polymer(s), especially where a delayed release solid dosage form is desired, is suitably selected from a polymer having a molecular weight of at least 10,000 g/mol, more suitably at least 15,000, though suitably less than 400,000 g/mol—in a particular embodiment the molecular weight is between 10,000 and 25,000 g/mol, whereas in other embodiments the molecular weight is between 100,000 and 350,000 g/mol. The shell polymer(s), especially where a delayed release solid dosage form is desired, is suitably selected from a polymer having a glass transition temperature (Tg) of at least 80° C., suitably at least 90° C., suitably at least 100° C., though suitably at most 200° C., more suitably at most 160° C.—most suitably a Tg between 90 and 160° C. In some embodiments, the shell polymer(s) may not have a glass transition temperature as such, though observed softening may still occur. The shell polymer(s), especially where a delayed release solid dosage form is desired, is suitably selected from:

an (optionally alkyl-, suitably methyl- or ethyl-) acrylate, methacrylate and/or ethacrylate polymer or copolymer (suitably free of any amine-containing monomeric units), suitably with a viscosity between 90 and 210 mPa·s, suitably with a molecular weight between 100,000 and 350,000 g/mol, and/or suitably with a glass transition temperature between 90 and 140° C.; wherein the relevant polymer or copolymer is suitably selected from: poly(methacylic acid-co-ethyl acrylate), suitably in a respective monomeric molar ratio of 1:1 (+/−5% for each molar value of the ratio); poly(methacylic acid-co-methyl methacrylate), suitably in a respective monomeric molar ratio of 1:1 (+/−5% for each molar value of the ratio); poly(methacylic acid-co-methyl methacrylate), suitably in a respective monomeric molar ratio of 1:2 (+/−5% for each molar value of the ratio); or a cellulose or cellulose derivative, suitably a hydroxypropyl methylcellulose (HPMC) derivative, most suitably a hydroxypropyl methylcellulose (HPMC) acetate succinate (HPMCAS), suitably with a molecular weight between 10,000 and 25,000 g/mol and/or suitably with a glass transition temperature between 100 and 145° C. (or suitably between 100 and 165° C.); wherein the relevant HPMCAS is suitably selected from Aqoat LG, Aqoat MG, and/or Aqoat HG. Suitably HPMC derivatives may, however, also include hydroxypropylmethylcellulose phthalate (HPMCP), such as HP-50, HP-55 and HP-55S grades thereof.

In principle any suitably polymer(s) may be used, including any one or more of those selected from an (optionally alkyl-, suitably methyl- or ethyl-) acrylate, methacrylate and/or ethacrylate copolymer (suitably comprising amine-containing monomeric units); an (optionally alkyl-, suitably methyl- or ethyl-) acrylate, methacrylate and/or ethacrylate polymer or copolymer (suitably free of any amine-containing monomeric units); a cellulose or cellulose derivative; polyvinyl alcohol (PVA); poly(lactic-co-glycolic acid) (PLGA); and/or any suitable pharmaceutical acceptable carrier.

The shell polymer(s) is suitably selected from Eudragit E, Eudragit NE, HPC SSL, Eudragit RS, Eudragit RL, HPC SL, HPC M, HPC H, Eudragit L100-55, Eudragit L100, Eudragit S100, Aqoat LG, Aqoat MG, Aqoat HG, and/or polyvinyl alcohol (PVA), or any combination of any of the aforementioned.

In some embodiments, especially where an active ingredient has limited solubility in a target solubilisation medium (e.g. in the body), shell polymer(s) such as polyvinylpyrrolidone polymers or polyvinylpyrrolidone-derived polymers may be employed. Such polymers can facilitate dissolution of an active ingredient that may otherwise exhibit limited solubility. In a particular embodiment, PVP K29-32 (a povidone) may be used. When present, suitably a PVP or PVP-based polymer is present (e.g. in a filament, solid dosage form, or core) at a concentration of between 20 and 80 wt %, suitably at a concentration between 40 and 60 wt %, suitably 45-55 wt %. PVP and PVP-based shell polymers may be used alongside one or more filler(s), and optionally with other ingredients such as plasticizer(s). Mixtures of different PVP or PVP-based polymers may also or alternatively be used (e.g. PVPs of different molecular weights).

In some embodiments, polyalkyleneglycol and polyalkyleneglycol-derived polymers may be employed as a shell polymer. In a particular embodiment the polyalkyleneglycol or polyalkyleneglycol-derived shell polymer is a polyethyleneglycol (PEG) or polyethyleneglycol-derived shell polymer. Suitably, wherever a PEG or PEG-based shell polymer is deployed, at least a portion of the PEG or PEG-based shell polymer has a molecular weight of at least 100,000, though suitably at most 1,000,000. However, a mixture of different polyalkyleneglycol and polyalkyleneglycol-derived polymers (e.g. PEG or PEG-based shell polymers) may be incorporated within filaments and/or corresponding dosage forms. For instance, a high molecular weight PEG may be used alongside a relatively low molecular weight PEG to achieve an optimal balance of properties. Higher molecular weight PEG and PEG-based polymers (e.g. $M_w \geq 80{,}000$) can serve as polymer molecules, whereas lower molecular weight PEG and PEG-based polymers (e.g. $M_w$ 200-20000) may serve as plasticizers and/or solubility enhancers. Increasing the proportions of lower molecular weight PEGs is likely to lower the $T_g$ of the resulting filament, Moreover, increasing the proportions of lower $M_w$ PEGs also favours accelerated drug release. Suitably any PEG or PEG-based shell polymers are used alongside one or more filler(s), though such polymers may be used with or without non-melting components.

Plasticizer(s)

The shell filament (and hence shell composition) may suitably comprise a plasticizer. Such a plasticizer may improve the quality of filament (e.g. in terms of smoothness, flexibility, fluidity on extrusion). The plasticizer may serve to lower the glass transition (or softening) temperature of the filament (or of the polymers), and consequent may allow lower extrusion nozzle operating temperatures to be used during printing and/or formation of the filament.

In general, if a filament has a glass transition temp (Tg) that is too high, it may be too brittle (for instance, to coil onto a filament spool) for an FFF 3D printer to handle (i.e. without breaking the filament), and/or may require extrusion nozzle operating temperatures that are so high that degradation of the ingredients within the filament may occur. Where a filament has a glass transition temperature that is too low, the filament may be too soft and/or flexible for an FFF 3D printer to handle, too distortable for consistent printing, and yields poor shape control and incoherent solid dosage form products. A plasticizer can be used as an additive to optimise the performance of a filament by obtaining the optimal glass transition or softening temperature and striking the right balance of properties.

The filament may comprise any suitable plasticizer. Many pharmaceutically acceptable plasticizers are known in the art for use in the formation of pharmaceutical solid dosage forms.

In a particular embodiment, the plasticizer may be selected from one or more of triethylcitrate (TEC), glycerol, castor oil, oleic acid, glycerol, tryacetin and polyalkylene glycols (e.g. a polyethylene glycol or polypropylene glycol, such as PEG400).

Certain plasticizers may be more appropriate than others, depending on the particular active ingredient and shell polymer(s). Particular combinations that offer excellent performance include:

TEC and/or triacetin (0.5-10 wt % thereof within the filament as a whole) plasticizer in conjunction with cellulose-based polymers, such as HPC, HPMC, and HPMCAS;

glycerol plasticizer in conjunction with PVA-based polymer;

TEC plasticizer (suitably 0.5-30 wt % thereof within the filament as a whole) in conjunction with (optionally alkyl-, suitably methyl- or ethyl-) acrylate, methacrylate and/or ethacrylate polymer or copolymers.

More than one plasticizer (optionally as defined herein) may be used.

In an alternative embodiment, instead of incorporating the plasticizer within the filament, the plasticizer may be coated upon the surface of the relevant filament, suitably so as to provide the required malleability and viable nozzle operating temperature. In a particular embodiment, during the printing process a filament (with or without a plasticizer therein) may be conveyed towards a corresponding extrusion nozzle via a plasticizer dispenser which coats the surface (or a part thereof) of said filament with the plasticizer. As such, in a particular embodiment, the shell filament may suitably comprise or be contacted with a plasticizer before it is extruded from a corresponding extrusion nozzle.

Filler(s)

As aforementioned mentioned, suitably shell filaments of the invention comprise one or more filler(s), suitably in the amounts stated. Suitably filler(s) are included alongside shell polymer(s) such as those described herein, and optionally also along with other excipients such as plasticizer(s), binders, and the like. Achieving an ideal balance between the respective ingredients is possible by following the teachings of the present specification. Typically, the inclusion of one or more filler(s) within a filament or filament composition will strengthen the resulting filaments and thereby facilitate their generation and processing during 3D printing. However, too much filler(s) may lead to a degree of brittleness, which can be mitigated through the judicious use of other ingredients (e.g. plasticizers and the like that may serve to soften the filaments), by lowering the proportions of filler, and/or changing the nature of the filler (e.g. its melting point).

Numerous fillers are known in the art of pharmaceuticals and nutraceuticals, and any of these may be deployed where appropriate or desired for a particular drug or nutraceutical formulation. Suitably, at least one (preferably all) of the filler(s) have a melting point exceeding the relevant operating temperature(s) of components with which the filaments make contact (e.g. printing nozzles, extrusion nozzles, and/or heated conveyors or feeders). Suitably, the filler(s) are substantially inert, and/or suitably have minimal or no interaction with other component(s) of the filament or dosage form, for instance a drug or polymer. Talc is an ideal filler for use in the filaments and dosage forms of the present invention, especially in conjunction with PVP or PEG polymers.

Other Ingredients

The shell filament may contain one or more other ingredients. Other ingredients may suitably include one or more excipients, excipient carriers, and/or diluents, all of which may be included in shell filament.

In particular, the one or more other ingredients within the printing filament may be selected from one or more fillers/diluents, antiadherants, binders, disintegrants, lubricants, glidants, flavourants, preservatives, sweeteners, and coatings.

Suitable antiadherants may include magnesium stearate. Suitable diluents/fillers may include plant cellulose, dibasic calcium phosphate, vegetable fats and oils, lactose, sucrose, glucose, mannitol, sorbitol, calcium carbonate, magnesium stearate, and/or microcrystalline cellulose. Suitable binders may include saccharides; polysaccharides/derivatives thereof, for example, starches, cellulose or modified cellulose such as microcrystalline cellulose and cellulose ethers such as hydroxypropyl cellulose, hydroxypropyl methyl cellulose, and derivatives thereof; sugar alcohols, for example, xylitol, sorbitol or maltitol; synthetic polymers, for example, polyvinylpyrrolidone (PVP), polyethylene glycol (PEG) . . . ). Suitable disintegrants may include crosslinked polyvinylpyrrolidone (crospovidone), crosslinked sodium carboxymethyl cellulose, croscarmellose sodium, modified starch sodium and/or starch glycolate. Suitable lubricants may include silica; fats, e.g. vegetable stearin; magnesium stearate or stearic acid; and/or talc. Suitable glidants may include fumed silica, talc, magnesium carbonate, and/or colloidal silica. Suitable coatings may include tablet coatings to protect tablet ingredients from deterioration by moisture in the air and make large or unpleasant-tasting tablets easier to swallow (e.g. a cellulose ether hydroxypropyl methylcellulose (HPMC) film coating; synthetic polymers, shellac, corn protein zein or other polysaccharides, gelatin; enteric coatings, for example, including fatty acid (s), wax(es), shellac, plastics, plant fibres). The generic classes of excipients are well understood by those skilled in the art.

In particular embodiments, the shell filament comprises talc (which is suitably a filler as mentioned above). Talc may serve as non-melting particles which improve the performance of the extrusion nozzle. A filament or a final solid dosage form (or a core thereof) may comprise between 10 and 50 wt % talc, 40 wt %, since too much lubricant may lead to poor adhesion of the solid dosage form to the build platform during printing.

Such excipients may be chosen to suit the properties of the final solid dosage form, the properties of a filament, or both, or a judicious compromise between both. For instance, in terms of the solid dosage form, excipient(s) may be chosen for ease of administration to the target patient population(s) by the intended route; improved dosing compliance; consistency and control of drug bioavailability; to enable bioavailability; improved active ingredient stability including protection from degradation; to ensure a robust and reproducible physical product. In terms of a filament (e.g. for use in FFF 3D printing), excipient(s) may be chosen to optimise the physical form and/or stability of the filament; to ensure a robust and reproducible physical products; flexibility and rigidity of the filament (an optimal balance between flexibility and rigidity of a filament is desirable to ensure that the filament can be conveyed successfully to an extrusion nozzle but then easily extruded from the nozzle); to enable production of optimal solid dosage forms (e.g. as per the aforementioned points).

Filament Coating

Filaments may suitably comprise a protective filament coating, suitably coated upon the outermost surface of said filament. Such filament coatings may be deployed regardless of whether single-head or multi-head (e.g. dual-head) printing is used, though such coatings are perhaps most applicable in multi-head printing scenarios where filaments are at increased risk of prolonged exposure to heat (and consequential filament degradation) whilst temporarily at rest (when not being printed) within their corresponding nozzles.

The protective filament coating(s) are suitably derived from corresponding protective filament coating compositions. Suitably the protective filament coating comprises pharmaceutically and/or nutraceutically acceptable ingredients. Suitably the protective filament coating us a liquid or oil, suitably having a high boiling point (e.g. at least 150° C., suitably at least 170° C., suitably at least 220° C.). The coating suitably reduces degradation of the filament upon exposure to heat. The protective filament coating (or composition) suitably comprises a liquid and/or oil. Suitably the protective coating does not prevent the relevant filament from melting or undergoing a glass transition at the operating temperature of the extrusion nozzle.

The inventors found that the use of olive oil BP, oleic acid, arachidonic acid and glycerol helps co-ordination between the two-nozzle and to evade drug-polymer filament degradation. Using such components to coat a filament is thought to provide a protective layer on the surface of the filament. Such components also have relatively high melting points and do not degrade at the processing temperature of the 3D nozzle.

Core

The core is suitably a non-printed composition. The core is suitably bulk dispensed (e.g. a pre-determined volume or mass thereof dispensed to a specific target location) and is suitably not characterised by a layered structure.

The core comprises or consists of a core composition. The core composition is unprintable via the structured printing nozzle through which the shell may be printed. The core composition suitably comprises one or more active ingredients. The core composition may be any suitable pharmaceutical, nutraceutical, or food supplement, composition, though most preferably the core composition is a pharmaceutical composition. Suitably the core composition is a pharmaceutical composition comprising at least one active and one or more pharmaceutically acceptable excipients or carriers. The core composition may be any known pharmaceutical composition, be it in a liquid or solid particulate form. However, the pharmaceutical composition may consist or essentially consist of the active ingredient(s).

Suitably the active ingredient is thermosensitive. Suitably the active ingredient is susceptible to decomposition at or above 200° C., suitably at or above 150° C., suitably at or above 100° C., suitably at or above 60° C. Such decomposition is suitably discernible by techniques known in the art, for example, DSC.

The core composition suitably is or comprises a liquid, a solid, or a gelled composition.

A liquid core composition may be a suspension (including a nanosuspension), emulsion, dispersion (including colloidal dispersion), etc. and may thus comprise particulate solids. Alternatively a liquid core composition may be a solution comprising the active ingredient.

A solid core composition is suitably a particulate solid composition. Particulate solids may include powders, granules, and pellets, though most suitably a solid particulate core composition comprises or consists of a powder or granules. Other forms of particulate solids that may be used are minitablets, crystals, cubes, etc.

The average particle size of the solid particulate core composition may suitably be greater than or equal to 10 nm, suitably greater than or equal to 100 nm, suitably greater than or equal to 1 μm, suitably greater than or equal to 10 μm, suitably greater than or equal to 100 μm, suitably greater than or equal to 200 μm. The average particle size of the solid particulate core composition may suitably be less than or equal to 1000 μm, suitably less than or equal to 500 μm, suitably less than or equal to 400 μm, suitably less than or equal to 100 μm, suitably less than or equal to 1 μm. In a particular embodiment the average particle size of the solid particulate core composition is between 1 and 10 μm. In a particular embodiment, the average particle size of the solid particulate core composition is between 50 μm and 300 μm, suitably between 60 μm and 250 μm, more suitably between 70 μm and 200 μm, most suitably between 80 μm and 190 μm.

A solid core composition may thus be a "bound" or "unbound" particulate solid. Though dispensed as a particulate solid, after dispensing a core composition may become or be otherwise transformed into a solid monolithic core within the shell into which the core is received. Such transformations to a monolithic core may be caused by the addition of a binder (e.g. where a further core composition precursor(s) or reactant(s) is used) or other such agent that may cause particles to bind together to form a "bound" particulate solid. In some embodiments, the solid core composition is an unbound particulate solid within the shell.

An advantage of the core-shell arrangement afforded by methods of the invention is that it permits high loadings of active ingredients in the core. As such, the core or core composition may comprise the one or more active ingredients at a concentration greater than or equal to 1 wt %, suitably greater than or equal to 10 wt %, suitably greater than or equal to 30 wt %, suitably greater than or equal to 50 wt %, suitably greater than or equal to 80 wt %.

Packaging of Solid Dosage Forms

Solid dosage form(s) of the invention may be packaged by any one of a number of methods well known in the art. Where, for example, pharmaceutical solid dosage forms according to the invention are produced via printing apparatus situated in a pharmacy (e.g. to provide a patient with customised medicaments on-demand), the pharmacist may package the solid dosage forms in a number of ways, including in tablet bottles, or even monitored dosing systems which may be subsequently dispatched to hospitals, care homes, and the like for ultimate dispensation to a patient.

In some embodiments, the packaging may be formed by the same or a different printing apparatus. In some examples, the packaging and solid dosage forms may be produced simultaneously, whereby the printing operation utilises one or more filament(s) pertaining to the solid dosage form, and one or more filament(s) pertaining to the packaging, and the packaging may be built around the solid dosage form(s) during printing.

Preparing Shell Filaments

A shell filament is suitably prepared by any one of the methods described in WO2016/038356 (by the present applicant).

EXAMPLES

The present invention will now be further described by way of the following non-limiting examples. In particular the Examples demonstrate that by printing a partial shell, dispensing a solid or a liquid thereinto, and closing the shell, one can viably produce a wide range of solid dosage forms. It will be understood, therefore, that the present invention is in no way limited to the specific exemplified compositions or equipment described, and that the concepts are broadly applicable to a host of embodiments.

Apparatus

Two types of basic apparatus for printing shells and dispensing cores may be as set forth in FIG. 1.

FIG. 1 is a schematic diagram of a dual FDM 3D printer adapted to accommodate a) a liquid dispenser or b) a powder/granule/pellets dispenser in combination with FDM 3D printer head.

FIG. 1(*a*) depicts a fused filament fabrication (FFF) 3D printer that has been adapted. The printer has one FFF printing nozzle (i.e. a structural shell printing nozzle), equipped with a nozzle, movable extruder, gears, and other standard 3D printing-nozzle components; a syringe (i.e. non-structural core dispenser) which replaces a second FFF printing nozzle previously installed within the printer; and a build platform. The apparatus is operable, via a computer, to print an open shell (as depicted on the building place) with a shell printing filament that passes through the FFF printing nozzle, and to thereafter fill the empty open shell with a liquid core composition dispensed from the syringe. The "filled shell" may then be closed with further shell printing filament that can be printed onto the top of the "filled shell".

FIG. 1(*b*) depicts the same apparatus as per FIG. 1(*a*) except that the liquid-dispensing syringe is replaced by a hopper equipped with an electronically-operated lower valve (i.e. tap). Such an apparatus is operable in like manner to that of FIG. 1(*a*), except that instead of dispensing liquid, particulate solids charged into the hopper are dispensed through the electrically operated lower valve into the open shell, before the filled shell is subsequently closed in the same manner as set for in relation to FIG. 1(*a*).

The aforementioned apparatuses were essentially formed from a dual head 3D printer that was modified by replacing a second FDM printing head with either i) an extrusion head (a syringe pressure controller based on open source design) or ii) in house built powder dispenser.

Figure 2:
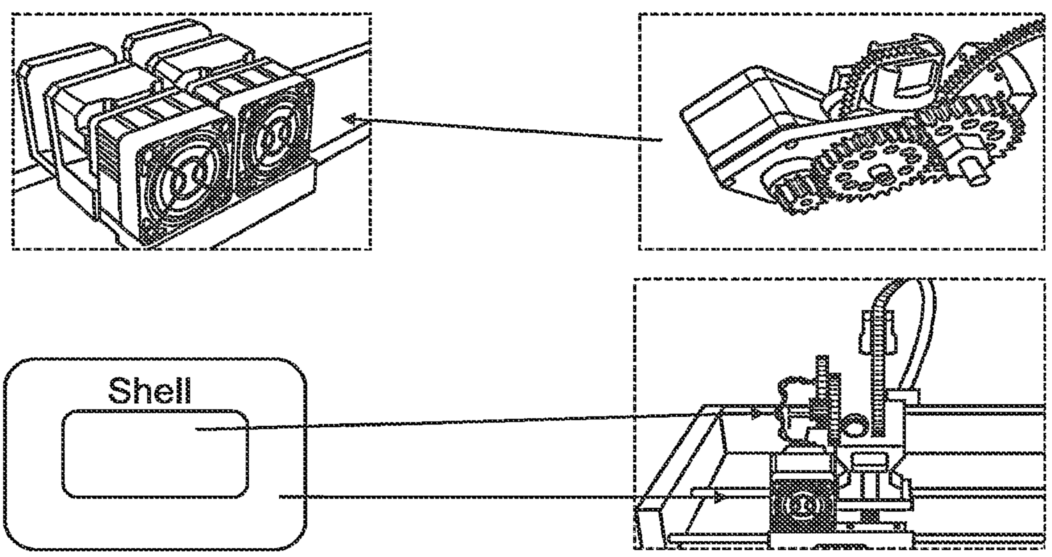
FIG. 2 shows a dual FDM 3D printer adapted to accommodate a liquid dispenser in combination with FDM 3D printer head and further illustrates, by way connecting arrows between an image of a basic core-shell structure and the relevant print, which components are configured to print each part of a core-shell structure.

FIG. 2 shows a dual FDM 3D printer adapted to accommodate a liquid dispenser in combination with FDM 3D printer head and further illustrates, by way connecting arrows between an image of a basic core-shell structure and the relevant print, which components are configured to print each part of a core-shell structure.

Example 1—Preparation of Dipyridamole Solution (Core Composition)

A model drug, dipyridamole, was chosen to test the suitability of this system to provide immediate and extended drug release. Its fluoresce colour and ease of detection allows focusing on the development process. Initially dipyridamole solution with different solvent systems was optimised as shown in Table 1. It was decided that the drug solution PEG 400 (10 mg/ml) is the maximum concentration that can be readily prepared.

TABLE 1 optimization of highly concentrated dipyridamole solution for liquid capsule feed.

| Formulation | Concentration (mg/ml) | Result |
|---|---|---|
| Dipyridamole + water | 20 | Slightly soluble |
| Dipyridamole + ethanol:water (20:80) | 20 | Slightly soluble |
| Dipyridamole + Peg 400 | 20 | Not complete dissolved |
| Dipyridamole + Peg 400: Ethanol | 5 | Soluble |
| Dipyridamole + Peg 400 | 10 | Soluble |

Example 2—Preparation of the Shell Filament (Shell Composition)

In order to engineer the shell, a methacrylic polymer with enteric properties (pH threshold>5.5), was utilized. Eudragit L 100-55, TEC and talc was used in the ratio 50:16.66:33.33 respectively. A physical mixture was extruded using HME at 135° C. feeding temperature and 125° C. extruding temperature. The nozzle size was 1 mm to allow the expansion of the filament to approximately 1.65 mm after extrusion. Similar procedures for preparing suitable printing filaments are outlined in the Examples of WO2016/038356.

Example 3—Dosing Accuracy of the Liquid Extruder

In order to assess the accuracy of the dosing the weight of dispensed solution following the order to fill a constant shape was assess in six replications (Table 2).

TABLE 2 reproducibility test for the liquid dispenser head

| Extrusion speed (mm/s) | Weight of solution (g) | | | | | | | | |
|---|---|---|---|---|---|---|---|---|---|
| 20 | 1 | 2 | 3 | 4 | 5 | 6 | Average | STDEV | % SD |
| | 0.0750 | 0.0729 | 0.0723 | 0.0830 | 0.1217 | 0.0973 | 0.0870 | 0.0194 | 22.3097 |

Example 4—3D Printing of Entric Liquid Capsule 3D printing of a liquid capsule was performed using the liquid-dispensing apparatus described above and illustrated schematically in FIG. 1(*a*)—i.e. using a dual FDM 3D printer with one of the printing heads replaced with a liquid or semi-solid extruder. The dipyridamole solution was loaded into the extruder and the filament into the regular FDM head.

Figure 3:
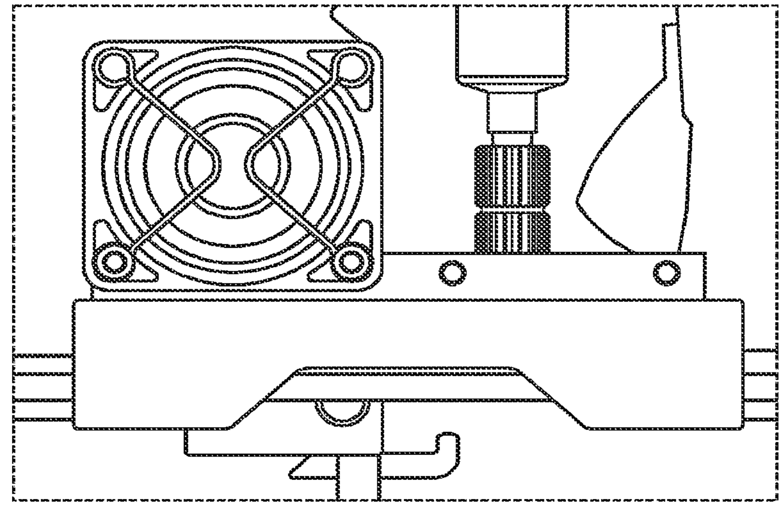
FIG. 3 shows a portion of the dual FDM 3D printer adapted to accommodate a liquid dispenser (right) in combination with FDM 3D printer head (left).

FIG. 3 shows a portion of the dual FDM 3D printer adapted to accommodate a liquid dispenser (right) in combination with FDM 3D printer head (left).

TABLE 3

3D Printing parameters for both shell filaments and dispensing of the core

| 3D printing parameters | core | Shell |
|---|---|---|
| Nozzle temperature (° C.) | 0 | 185 |
| Platform temperature (° C.) | 40 | |
| Extrusion speed (mm/s) | 20 | |
| Nozzle size (mm) | 0.4 | 0.41 |

TABLE 4

Tablet dimensions for the shell and the liquid core

| | X (mm) | Y (mm) | Z (mm) |
|---|---|---|---|
| Core | 8.00 | 3.16 | 1.50 |
| shell | 18.38 | 8.00 | 7.45 |

TABLE 5

The positions of the shell and the core during liquid capsule printing process

| | X (mm) | Y (mm) | Z (mm) |
|---|---|---|---|
| Core | −101.11 | −45.07 | 3.50 |
| shell | −101.11 | −45.07 | 0.00 |

Example 5—In Vitro Dissolution Test

The in vitro dissolution studies was carried out manually in a USP II dissolution tester. Samples were taken at 15 mins interval for 4 hrs. This was filtered through a 0.2 µm filter and analysed using HPLC. The pH of the media was from 1.2 to 6.8 after 2 hrs by adding sodium tribasic phosphate buffer.

HPLC Parameters

Agilent technologies 1200 series HPLC system was also used in the dipyridamole analysis. Randomly selected tablets were placed in a 500 ml volumetric flask containing 250 ml of HPLC water. This was sonicated for 2 hours before adding 250 ml of acetonitrile and further sonicated for 30 mins, cooled and filtered before analysis. The HPLC system consists of XTerra RP 18 4.6×150 mm, 5 µm column (made in Ireland) which was maintained at 40° C. The mobile phase was comprised of phosphate buffer pH 6.8 and acetonitrile (60:40) at a flow rate of 1 ml/min. The injection volume was 10 µl and the maximum run time for the assay was 10 mins. 282 nm was the assay wavelength.

Figure 4:
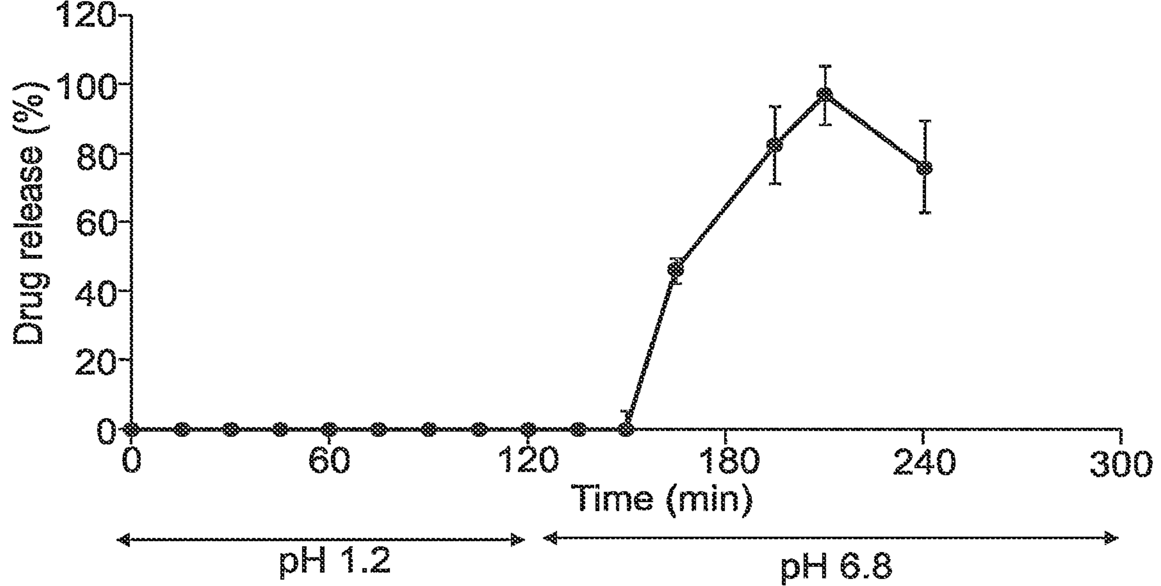
FIG. 4 is a graph showing a time-course in vitro drug release profile for of dipyridamole release from Eudragit L based capsules filled with drug suspension.

FIG. 4 is a graph showing a time-course in vitro drug release profile for of dipyridamole release from Eudragit L based capsules filled with drug suspension. It was possible to control drug release during the acidic phase of the experiment (2 hours). Following pH change, the model drug started to be released after 30 min, indicating the proof of concept of crafting an enteric soft capsule based on this technology.

It was decided that it is possible to include more drug contents by employing a drug suspension rather than drug solution. In the next step, a dipyridamole suspension was used in the liquid dispenser so higher drug concentration can be employed in the system.

Example 6—Preparation of Dipyridamole Suspension As a Feed Solution for Liquid Dispenser Dipyridamole 1500 mg was suspended in distilled water (5%) and sonicated for 10 mins. This was then milled using Ultra Turrax Homogeniser at 25000 rpm for 1 hr. Methocel E4 (0.5%) was added to the sample and then probe sonicated at 15 mins interval in an ice bath for 1 hr. The size of micro-particles were investigated using Mastersizer.

NB: Methocel E4 was added after size reduction using Ultra Turrax to reduce foam production The use of PVP as a suspending agent produced larger particles.

TABLE 6

Size reduction, homogenisation, and general preparation conditions

| Size reduction technique | Time (mins) | Size (μm) | SPAN |
|---|---|---|---|
| Homogenisation | 60 | 9.461 | 3.193 |
| Probe sonication | 60 | 5.877 | 2.013 |

The reduction of particle size to less than 6 micron significantly retards the sedimentation rate of the drug. It is anticipated that employing nano-suspensions may allow for even better accuracy.

Example 7—Dosing Accuracy and Relationship Between the Theoretical Volume and Actual Volume for Single and Dual FDM Printing This was carried out using a theoretical cube shape as the object with the dimensions as stated bellow. This was to be able to relate the theoretical volume to the actual volume obtained from using different nozzle sizes (0.25, 0.41 and 0.84 mm).

TABLE 7 the theoretical volume of cube object that was used to control the liquid dispenser.

| Cube dimension (mm) | Theoretical vol ($mm^3$) | Theoretical vol (ml) |
|---|---|---|
| 6.21 | 240 | 0.24 |
| 5.85 | 200 | 0.2 |
| 5.43 | 160 | 0.16 |
| 4.93 | 120 | 0.12 |
| 4.31 | 80 | 0.08 |
| 3.42 | 40 | 0.04 |
| 2.71 | 20 | 0.02 |
| 2.15 | 10 | 0.01 |

In order to establish the link between theoretical volume and the practical suspension volume that was dispensed a number of calibration curves with different nozzle sizes were plotted.

Figure 5:
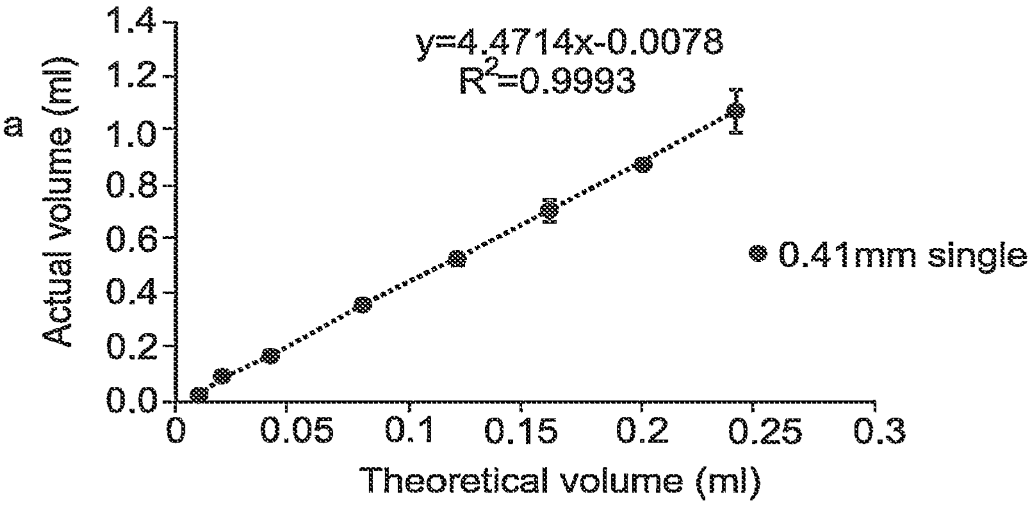
FIG. 5 shows a calibration curve for the actual volume against theoretical volume for single head printing using (a) 0.25, (b) 0.41 or (c) 0.84 mm nozzle sizes.
Figure 5:
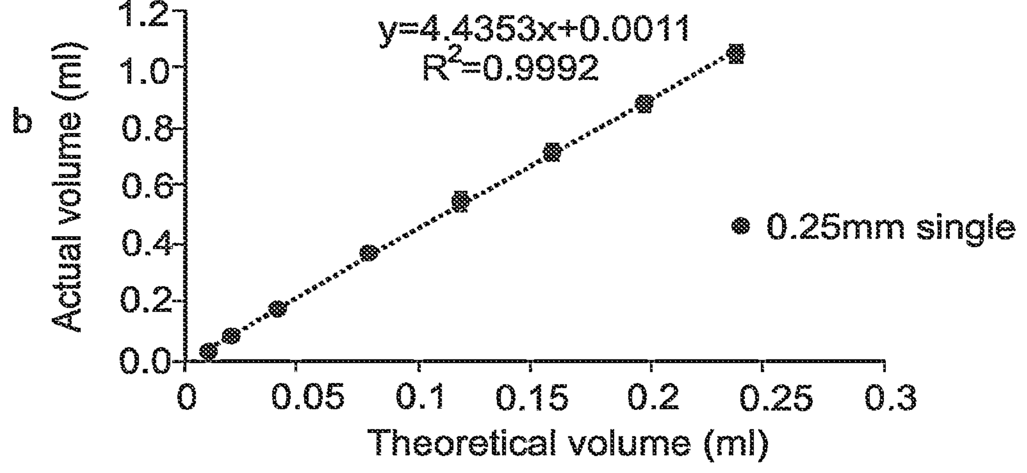
Figure 5:
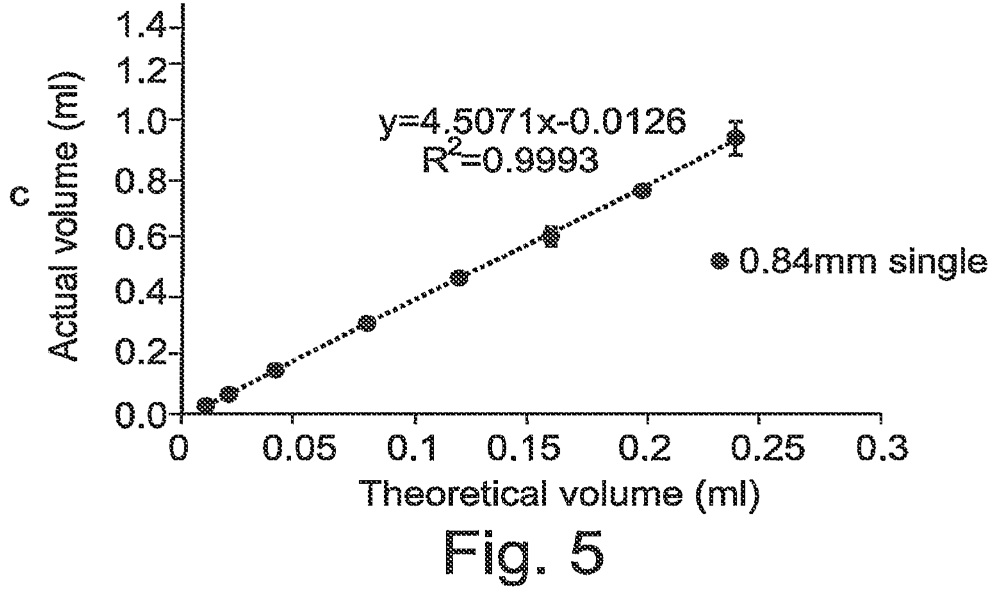
Figure 6:
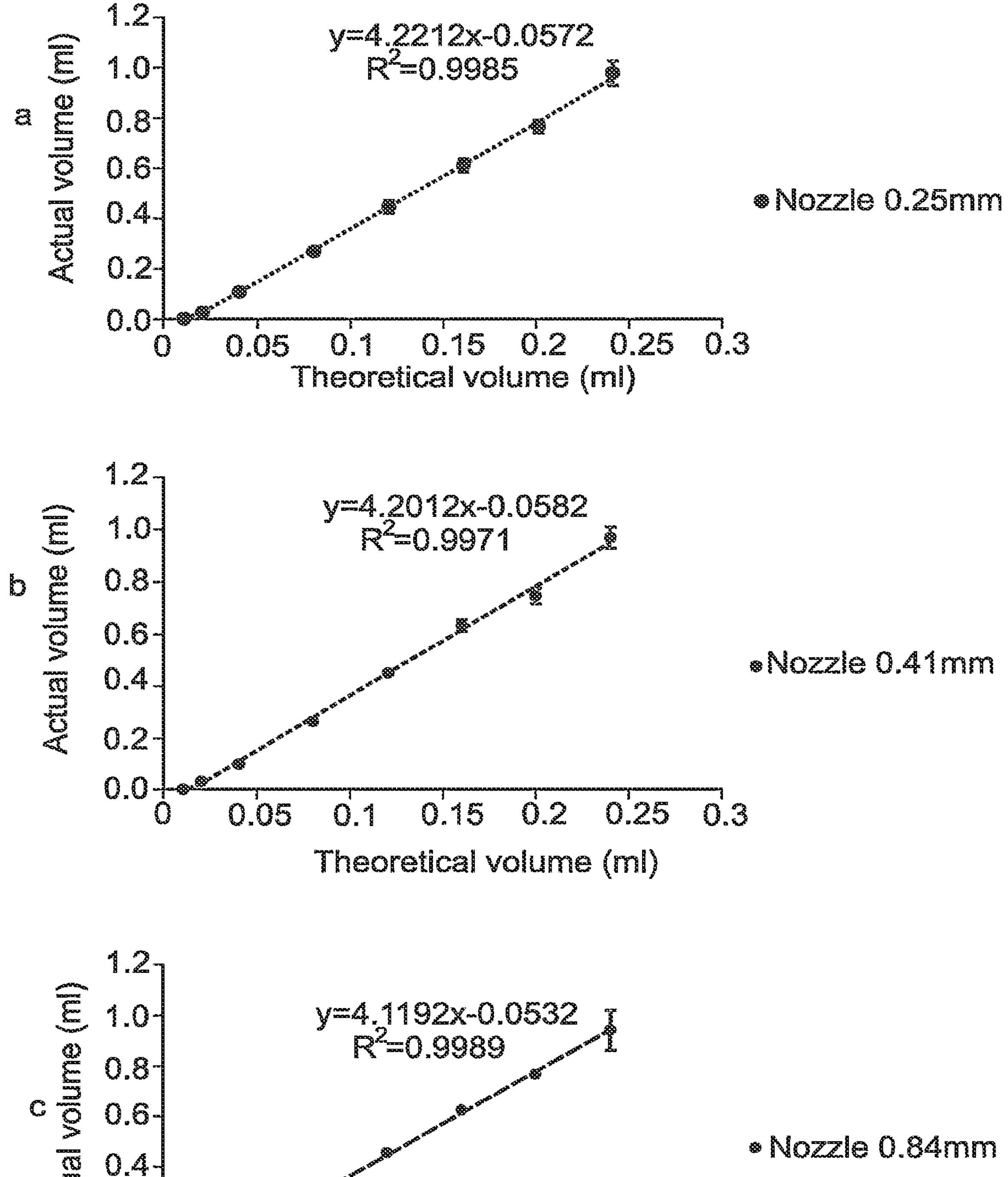
FIG. 6 shows a calibration curve for actual volume against theoretical volume for dual printing head using (a) 0.25, (b) 0.41 or (c) 0.84 mm nozzle size.
Figure 7:
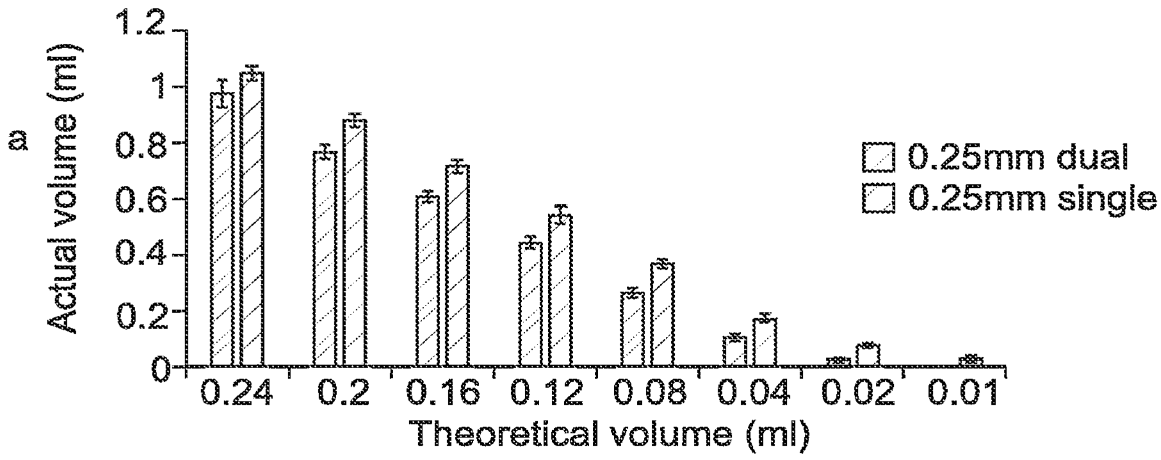
FIG. 7 shows the relationship between actual volumes from single and dual printing from (a) 0.25, (b) 0.41 or (c) 0.84 mm nozzle.
Figure 7:
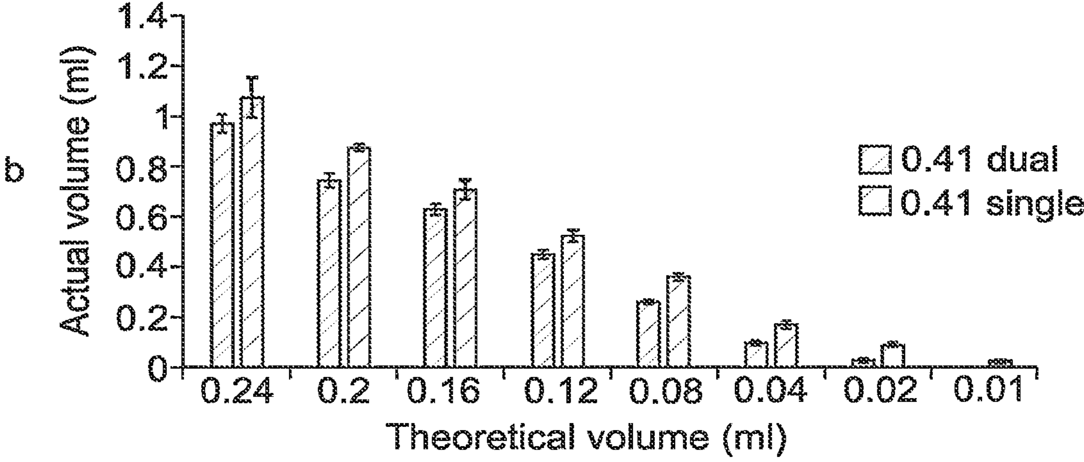
Figure 7:
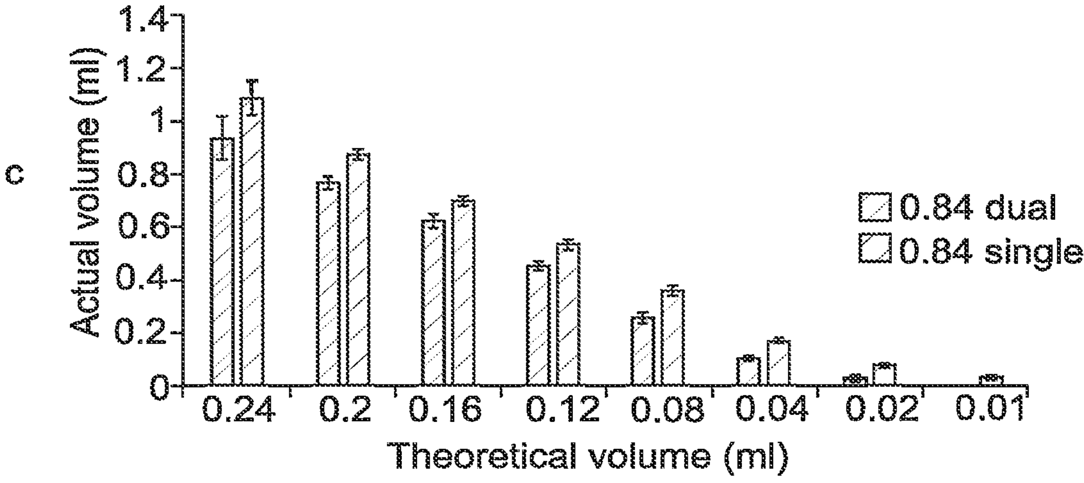

It is clear that it is possible to control the volume dispensed by controlling the theoretical volume of dispensed liquid in the printer software (FIG. 5). This was achieved across the 3 different nozzle dispenser. It is also noted that the linearity is maintained when dual printing is employed (FIG. 6). However the dispensed volume slightly dropped when dual printing was employed (FIG. 7). This might be related to the changes in the pressure applied to the syringe during co-ordination with the FDM printer's head.

FIG. 5 shows a calibration curve for the actual volume against theoretical volume for single head printing using (a) 0.25, (b) 0.41 or (c) 0.84 mm nozzle sizes. This proves the possibility of controlling the dose with different nozzle sizes FIG. 6 shows a calibration curve for actual volume against theoretical volume for dual printing head using (a) 0.25, (b) 0.41 or (c) 0.84 mm nozzle size.

FIG. 7 shows the relationship between actual volumes from single and dual printing from (a) 0.25, (b) 0.41 or (c) 0.84 mm nozzle.

Example 8—Example of Controlling the Dose 3D Printing of the Liquid Capsule

The optimized liquid suspension was used as a feed to fabricate a 3D printed enteric capsule In this example, a capsule for enteric liquid capsule containing a suspension of dipyridamole. Three different doses of the dipyridamole was tried.

The enteric shell was prepared using Eudragit L55-100 and as detailed previously in section. The printing parameter is detailed in Table 5.

TABLE 8

Printing parameters for dual 3D printino of enteric capsule

| 3D printing parameters | core | Shell |
|---|---|---|
| Nozzle temperature (° C.) | 0 | 185 |
| Platform temperature (° C.) | | 40 |
| Extrusion speed (mm/s) | | 20 |
| Nozzle size (mm) | 0.4 | 0.41 |

TABLE 9

The dimensions of the core of the tablet has been modified to encapsulate a different volume (dose) of the drug

| | Volume (μl) | X (mm) | Y (mm) | Z (mm) |
|---|---|---|---|---|
| Core | 30 | 7.5 | 2 | 2 |
| | 45 | 7.5 | 3 | 2 |
| | 60 | 705 | 4 | 2 |
| shell | | 18.38 | 8.00 | 7.45 |

It was also necessary to position the core (liquid) in an elevated position to allow the formation of the shell with a wall of 'significant' heights in order to contain the poured liquid (Table 8).

TABLE 10 the positioning of the shell and the core of the capsule

| | X (mm) | Y (mm) | Z (mm) |
|---|---|---|---|
| Core | −101.11 | −45.07 | 2.50 |
| shell | −101.11 | −45.07 | 0.00 |

Example 9—In Vitro Release Studies

UV Spectrophotometric Analysis

The in vitro dissolution studies was carried out using a USP II dissolution tester. Samples were taken automatically at 5 mins interval and analyse for below detailed HPLC. The pH of the media was from 1.2 to 6.8 after 2 hrs by adding sodium tribasic phosphate buffer.

HPLC Analysis

Agilent technologies 1200 series HPLC system was also used in the dipyridamole analysis. Randomly selected tablets were placed in a 500 ml volumetric flask containing 250 ml of HPLC water. This was sonicated for 2 hours before adding 250 ml of acetonitrile and further sonicated for 30 mins, cooled and filtered before analysis. The HPLC system consists of XTerra RP 18 4.6×150 mm, 5 μm column (made in Ireland) which was maintained at 40° C. The mobile phase was comprised of phosphate buffer pH 6.8 and acetonitrile (60:40) at a flow rate of 1 ml/min. The injection volume was 10 μl and the maximum run time for the assay was 10 mins. 282 nm was the assay wavelength.

Figure 8:
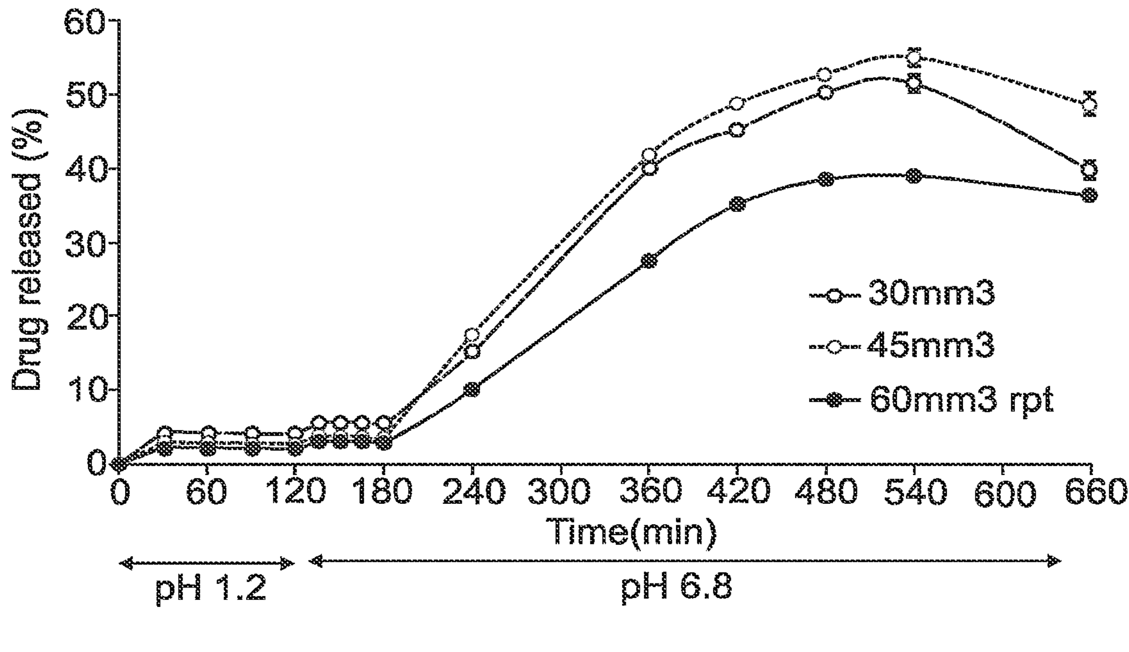
FIG. 8 shows in vitro release of dipyridamole from Eudragit L based capsule filled with drug suspension with different loading.

FIG. 8 shows in vitro release of dipyridamole from Eudragit L based capsule filled with drug suspension with different loading. It was possible to maintain grastric resistant properties with no drug release in the acid and extended release in gastric media pH. This example provides a proof of concept of fabricating an enteric polymer with potential of controlling dose to suit a particular patient.

Example 10—3D Printing of Immediate Release Liquid Capsule

In order to prove the possibility of crafting immediate release liquid capsule using this technology, the capsule was crafted using the same dipyridamole suspension but with filament made of immediate release polymer (Eudragit E), the polymer is highly soluble in the acidic medium.

A mixture (10 g) consisting of 45% Eudragit E po, 5% triethyl citrate and 50% talc was physically mixed before feeding into a hot melt extruder at 100° C. This was allowed to mix for 5 min before extruding at 90° C. 1.5 mm nozzle was used on the extruder and extrusion was done using torque of 0.4 N.

Preparation of Dipyridamole Suspension (As Stated in Previous Example)

TABLE 11

Printing parameters for dual 3D printing of immediate release capsule

| 3D printing parameters | core | Shell |
|---|---|---|
| Nozzle temperature (° C.) | 0 | 135 |
| Platform temperature (° C.) | 40 | |
| Extrusion speed (mm/s) | 90 | |
| Nozzle size (mm) | 0.25 | 0.4 |

TABLE 12

The dimensions of the core of the tablet has been modified to encapsulate a different volume (dose) of the drug

| | Volume (μl) | X (mm) | Y (mm) | Z (mm) |
|---|---|---|---|---|
| Core | 15 | 7.5 | 1 | 2 |
| | 30 | 7.5 | 2 | 2 |
| | 45 | 7.5 | 3 | 2 |
| Shell (1.2 mm thick) | | 19.59 | 9.20 | 8.65 |

TABLE 13 the positioning of the shell and the core of the capsule

| | X (mm) | Y (mm) | Z (mm) |
|---|---|---|---|
| Core | −101.11 | −45.07 | 2.50 |
| shell | −101.11 | −45.07 | 0.00 |

Figure 9:
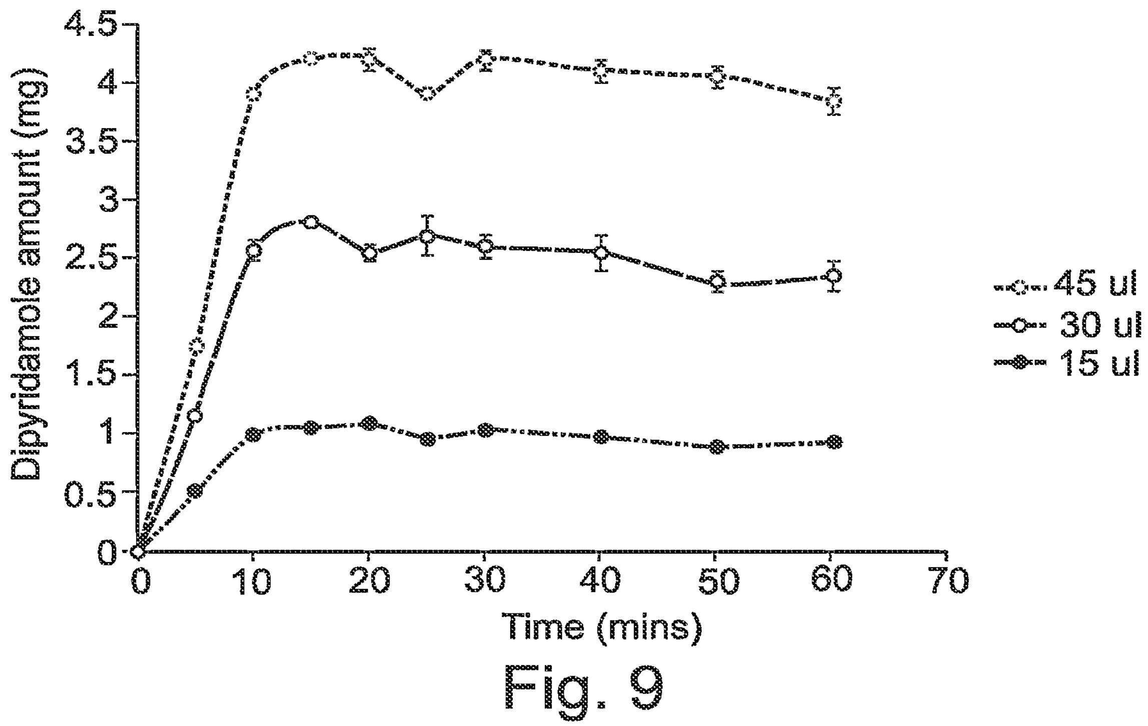
FIG. 9 shows the release profile of dipyridamole from immediate release shell.

FIG. 9 shows the release profile of dipyridamole from immediate release shell. It is clear that 100% drug release is achieved within 15 min of introduction to the acidic media, hence complying with pharmacopeial criteria for immediate release capsules. It was also possible to control the drug dose of the drug by modifying the volume of the dispensed volume through the printer software scale's command.

Further Examples

Example 11—Example of Liquid Capsule Containing a Controlled Dose of a Drug Suspension In this example, immediate release capsules were produced. The capsules were filled with a suspension of a model drug, dipyridamole. Using computer aided software it was possible to control the dose of dipyridamole by controlling the volume dispensed using different designs for the core.

Preparation of Shell Filament

For the preparation of the shell, API-free Eudragit EPO or RL filaments were produced by a HAAKE MiniCTW hot melt compounder (Thermo Scientific, Karlsruhe, Germany). An optimised ratio of a powder mixture containing a the polymer, plasticizer (TEC) and filler (talc) was gradually added to the HME and allowed to mix for 5 min at 80 rpm to allow homogenous distribution of the molten mass. Afterwards, the filament was extruded at 20 rpm. The processing parameters for the hot melt extrusion are shown in Table 14.

Preparation of the Liquid Core

Two liquid model cores (aqueous active solution or suspension) were prepared to be used in the syringe dispenser:

Dipyridamole suspension was initially prepared by sonicating 1.5 g/30 mL of aqueous dipyridamole suspension. Size reduction was achieved by initial application of T8.01 Ultra Turrax Homogeniser (IKA, Germany) at 25,000 rpm. This was carried out for 1 h at 15 min interval with 5 min cooling time between the intervals. Methocel E4 (0.5% w/v) was added to the suspension before probe sonicating using Sonics Vira cell (USA) at 15 min interval in an ice bath for additional 4 h using an amplitude of 70%. The final suspension we diluted with Methocel E4 (0.5% w/v) to achieve a drug concentration of 1.50 w/v. The size distribution of dipyridamole particles in the suspension were confirmed by using a Mastersizer 2000 laser diffractomer (Malvern Instruments, UK).

Modification of Dual FDM 3D Printing

In order to make the manufacturing of the liquid capsule fully automated, a Makerbot replicator Experimental 2× dual FDM 3D printer (MakerBot Industries, New York, USA) was modified to dispense liquids. The right extruder of the 3D printer was replaced with a syringe-based liquid dispenser as shown in FIG. 1. The design for the paste extruder was obtained from an open source website and was 3D printed using an M2 Makergear FDM 3D printer (MakerGear, LLC, Ohio, US).

Liquid Capsule Design and Printing

The shells were designed as a 1.6 mm thick capsule with different dimensions as shown in Table 15. As the liquid core will be dispensed and will take the shape of the cavity of the shell, the core of the tablet was designed as a cube to simplify controlling dispensed volume by changes the cube volume. For the fabrication of liquid capsule, two different printing modes were employed:

a. Single-phase printing: In Makerbot Desktop software (MakerBot Industries, New York, USA), the core was placed in the centre of the cavity of its corresponding shell and was printed by the interchanging printing of the shell filament and core liquid.

b. Multi-phase printing: In Simplify3D software, the shell was designed to comprise a complementary bottom and a cap. This liquid capsule printing was done in three phases: i) printing of the bottom, ii) filling of the liquid and iii) sealing of the bottom in a separate 3D printing stage.

The liquid capsules for both modes were printed with cube dimensions corresponding to 80, 120, 240 or 320 μL (Table 15). The settings of the software were modified and the parameters of 3D printing of the shell were printed as shown in Table 14. The resolution was set at medium (200 μm layer thickness), the infill was 100% and the internal and external infill pattern were set at Grid and Concentric respectively. The outline overlap was set at 90% and the rest of the setting were default. The script of the software was also modified to prevent priming of the liquid dispenser to reduce waste and as priming was not necessary for liquids.

Figure 10:
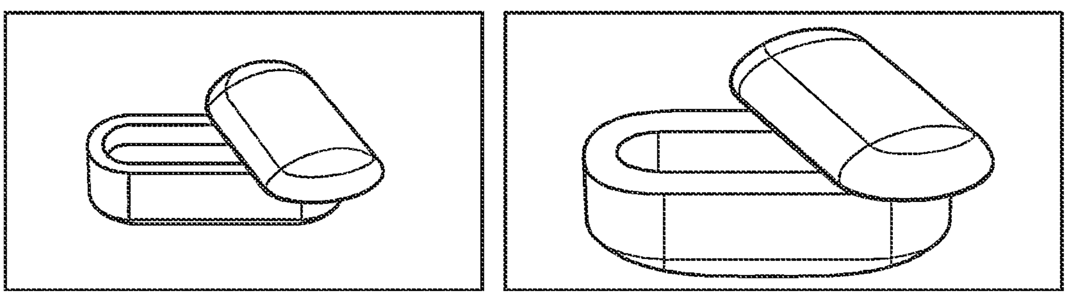
FIG. 10 shows a rendered image and photograph of a liquid capsule made of an immediate release shell (Eudragit E shell) and filled with microsuspension of dipyridamole (1.5% w/v).

FIG. 10 shows a rendered image and photograph of a liquid capsule made of an immediate release shell (Eudragit E shell) and filled with microsuspension of dipyridamole (1.5% w/v).

TABLE 14

Shell filament formulations with their HME and 3D printing processing parameters

| | Polymer (%) | TEC (%) | Talc (%) | Processing temp (° C.) | Extrusion temp (° C.) | Nozzle size (mm) | 3D printing temp (° C.) | Platform temp (° C.) |
|---|---|---|---|---|---|---|---|---|
| Eudragit EPO | 45 | 5 | 50 | 100 | 90 | 1.7 | 135 | 40 |
| Eudragit RL | 45 | 5 | 50 | 130 | 120 | 1.7 | 170 | 20 |
| Eudragit L100-55 | 50 | 16.67 | 33.33 | 135 | 125 | 1 | 185 | 40 |

TABLE 15

Theoretical volume dimensions, of core and shell and wight, of estimated and actual dose

| Sample | Theoritical Volume (μm) | Core's Dimensions (mm) x | y | z | Shell's Dimensions (mm) x | y | z | Weight (mg) | Estimated Volume (μm) | Estimated Dose (mg) | Actual dose (mg) |
|---|---|---|---|---|---|---|---|---|---|---|---|
| Core 1 | 80 | 4.32 | 4.32 | 4.32 | 23 | 10.35 | 6.74 | 82.25 ± 6.95 | 78.33 ± 6.62 | 1.18 ± 0.10 | 1.51 ± 0.17 |
| Core 2 | 160 | 5.43 | 5.43 | 5.43 | 23 | 10.35 | 6.74 | 185.83 ± 23.75 | 176.98 ± 22.62 | 2.65 ± 0.34 | 3.11 ± 0.17 |
| Core 3 | 240 | 6.22 | 6.22 | 6.22 | 23 | 10.35 | 7.74 | 284.55 ± 1.48 | 271 ± 1.41 | 4.07 ± 0.02 | 4.99 ± 0.49 |
| Core 4 | 320 | 6.84 | 6.84 | 6.84 | 23 | 10.35 | 9.74 | 385.73 ± 30.57 | 367.36 ± 29.11 | 5.51 ± 0.44 | 6.60 ± 0.86 |

In Vitro Dissolution Test

In vitro drug release studies for all liquid capsules used in this study were carried out in triplicate in a suitable dissolution media at 37±0.5° C. with a paddle speed of 50 rpm.

Eudragit EPO-dipyridamole liquid capsule release studies was investigated using an Erweka DT 600 dissolution tester (USP II). The media used was 900 mL of 0.1 M HCl. Four mL aliquots were manually collected using 5 mL Leur-Lok syringes at 0, 5, 10, 15, 20, 25, 30, 40 and 60 min time intervals and filtered through a Millex-HA 0.45-μm filter. Each aliquot withdrawn was replaced with 4 mL of 0.1 M HCl. These where analysed using HPLC methods reported in section 2.11.

Figure 11:
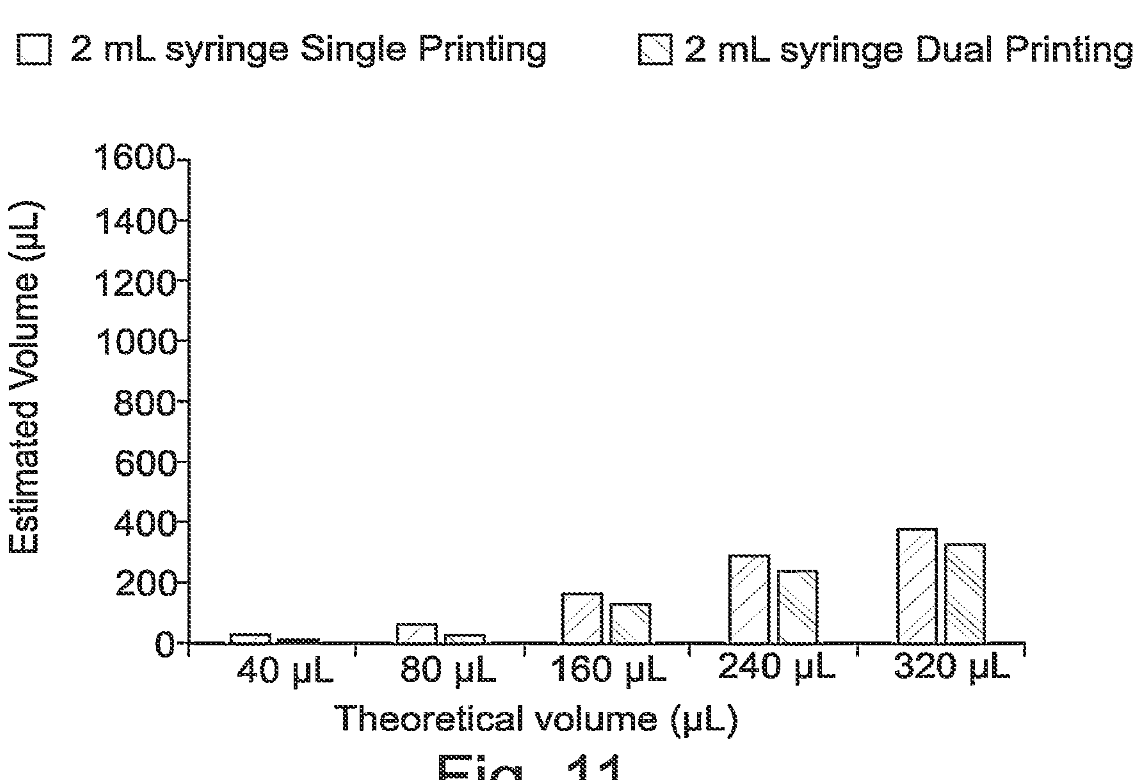
FIG. 11 is a chart showing the impact of single and alternating printing modes from the liquid dispenser using a 2 ml syringe.

FIG. 11 is a chart showing the impact of single and alternating printing modes from the liquid dispenser using a 2 ml syringe.

Figure 12:
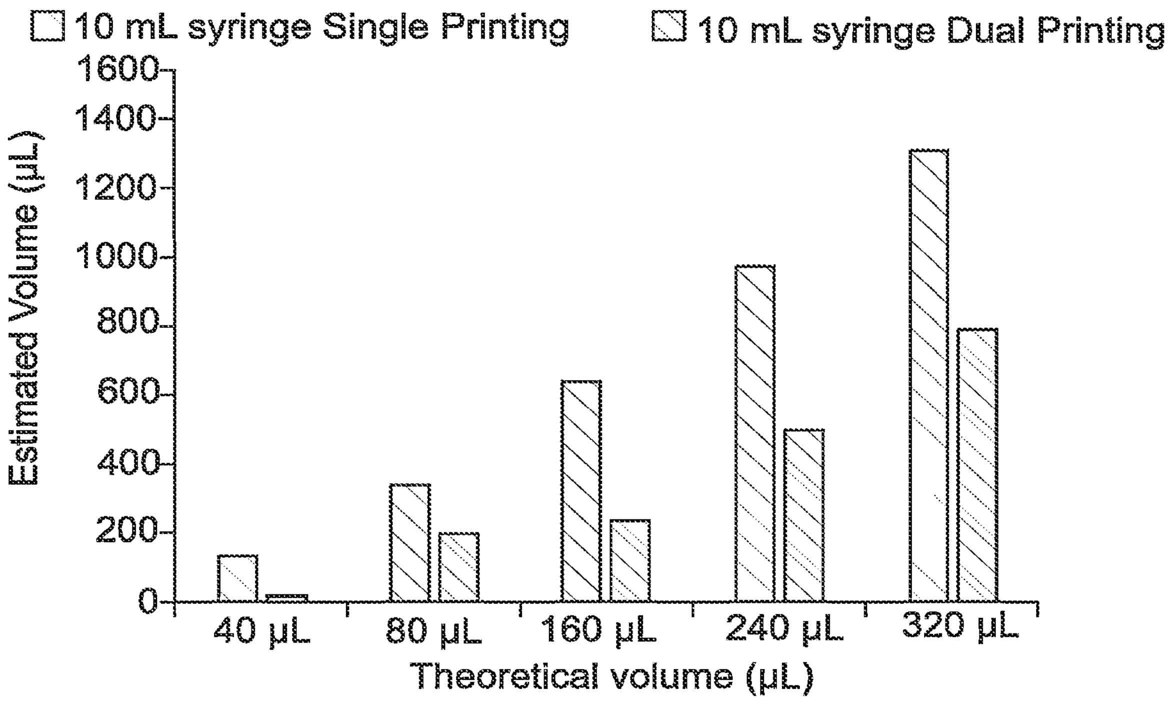
FIG. 12 is a chart showing the impact of single and alternating printing modes from the liquid dispenser using a 10 ml syringe.

FIG. 12 is a chart showing the impact of single and alternating printing modes from the liquid dispenser using a 10 ml syringe.

Figure 13:
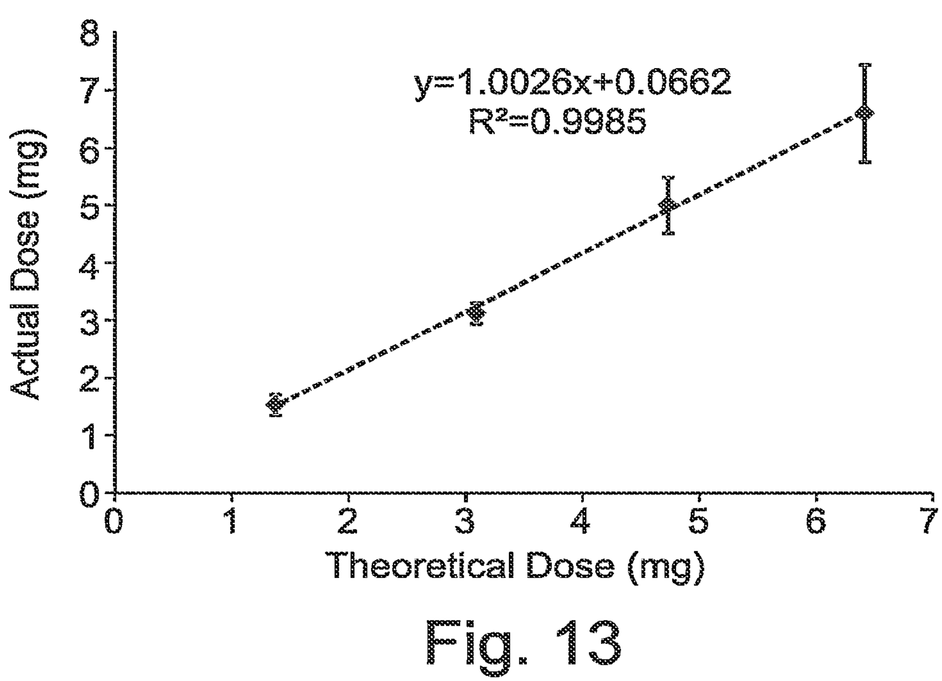
FIG. 13 is a graph showing the linear relationship between theoretical volumes calculated volumes based on volume of design and the actual dose achieved via 3D printing.

FIG. 13 is a graph showing the linear relationship between theoretical volumes calculated volumes based on volume of design and the actual dose achieved via 3D printing.

Figure 14:
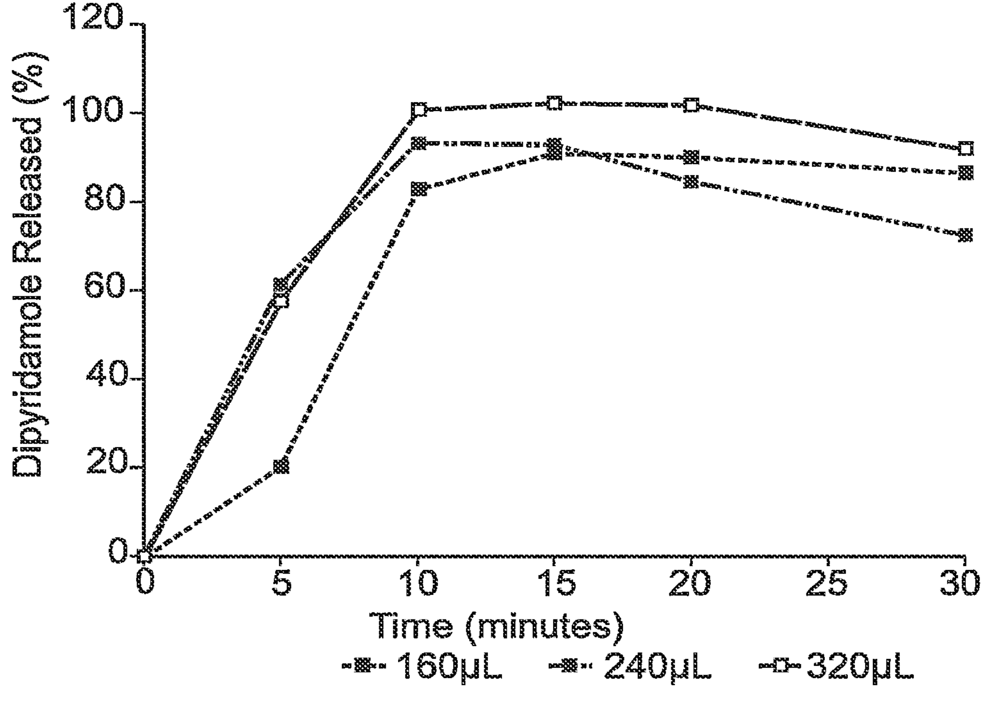
FIG. 14 shows in vitro immediate release profiles for dypiridamole suspension from 3D printed liquid Eudragit EPO capsule using USP II with different core volumes in gastric media (pH 1.2).

FIG. 14 shows in vitro immediate release profiles for dypiridamole suspension from 3D printed liquid Eudragit EPO capsule using USP II with different core volumes in gastric media (pH 1.2).

The above experiments demonstrate the possibility to control liquid doses within capsules based on an immediate release shell and a liquid suspension. Doses can be easily modified through merely changing the dispensed volume. Though both single-phase and multi-phase printing models allowed adequate control of dose, the bi/multi-phasal model afforded less troubleshooting and gave a higher success rate.

Example 12—Experiments With Different Shell Printing Methods

The same capsule design (Eudragit E) as per Example 11 were filled with dipyridamole suspension. During capsule shell printing two printing modes were tested.

Figure 15:
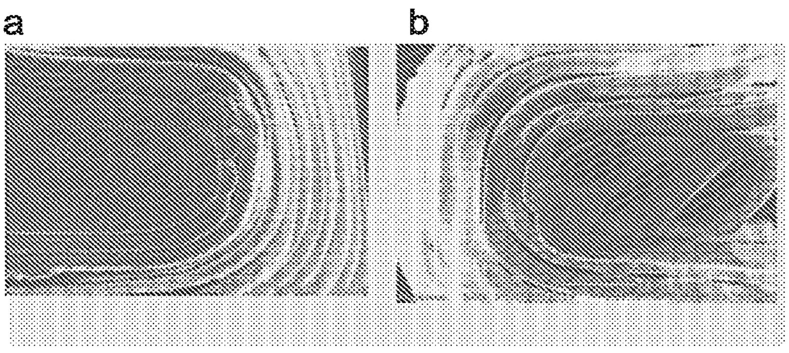
FIG. 15 shows SEM images of the top of shell produced by two different filling modes: a) concentric Filing and b) rectangular filling.

FIG. 15 shows SEM images of the top of shell produced by two different filling modes: a) concentric Filing and b) rectangular filling.

Capsules formed via concentric filling were much more effective than rectangular-filling designs in controlling liquid contents and preventing leakage.

Example 13—Example Liquid Capsules Containing Drug Solutions in Both Immediate Release and Extended Release Shells In this example, the core composition is a drug solution (rather than a drug suspension as per previous examples) and it is shown to be suitable in both immediate release and extended release systems.

The capsules were prepared as per Example 11, with shell materials shown in Table 14. Eudragit RL was used for extended release shells.

Theophylline solution was prepared by adding 15 g of citric acid and 1.5 g of Tween 80 to a 4% w/v theophylline aqueous suspension (50 mL). This was heated to 65° C. and stirred until a complete solution is formed. Methocel E4 was then added to achieve a Methocel solution concentration of 0.25% w/v before cooling in an ice bath.

In Vitro Dissolution Test

Eudragit EPO-theophylline liquid capsule release studies was conducted using an AT 7 Smart dissolution USP II apparatus (Sotax, Switzerland) equipped with in-line UV/VIS spectrophotometer (PG Instruments Limited, UK). The media used was 900 ml of 0.1 M HCl. The amount of released theophylline was determined at 5 min intervals by at a wavelength of 272 nm and path length of 1 mm. Data was analysed using IDISis software (Automated Lab, 2012). For Eudragit RL 100-Theophylline liquid capsules, the test were carried out using 750 ml of a stimulated gastric fluid (0.1 M HCl, pH 1.2) for 2 hrs followed by 12 h exposure to pH 6.8 phosphate buffer. This was carried out using AT 7 Smart dissolution USP II apparatus.

Figure 16:
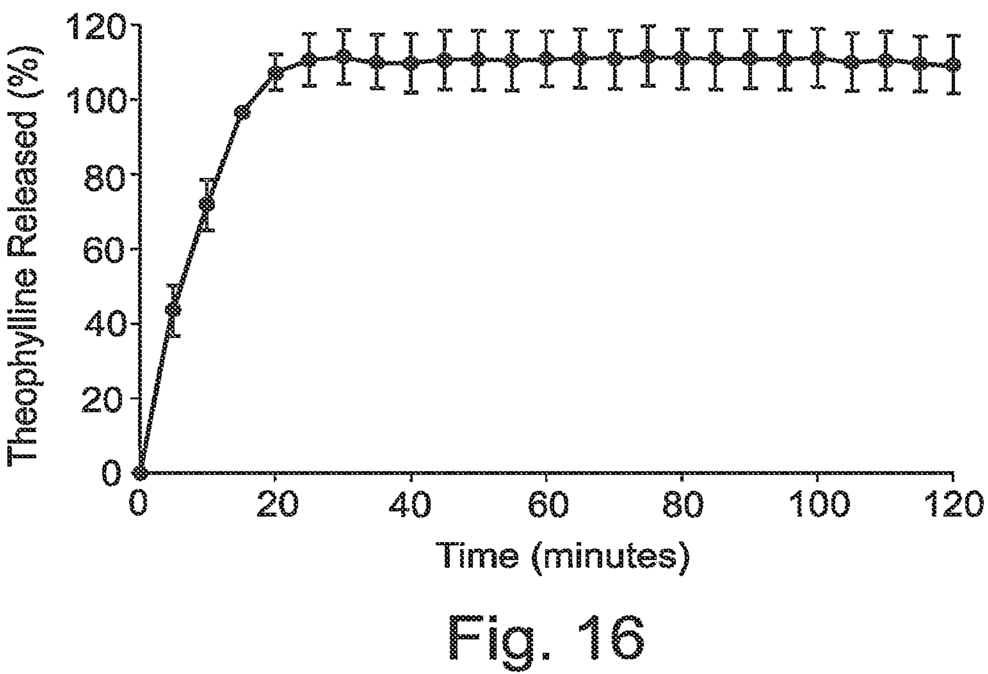
FIG. 16 shows release profiles for theophylline-cored-capsules produced with immediate release shells containing Eudragit EPO.

FIG. 16 shows release profiles for theophylline-cored-capsules produced with immediate release shells containing Eudragit EPO.

Figure 17:
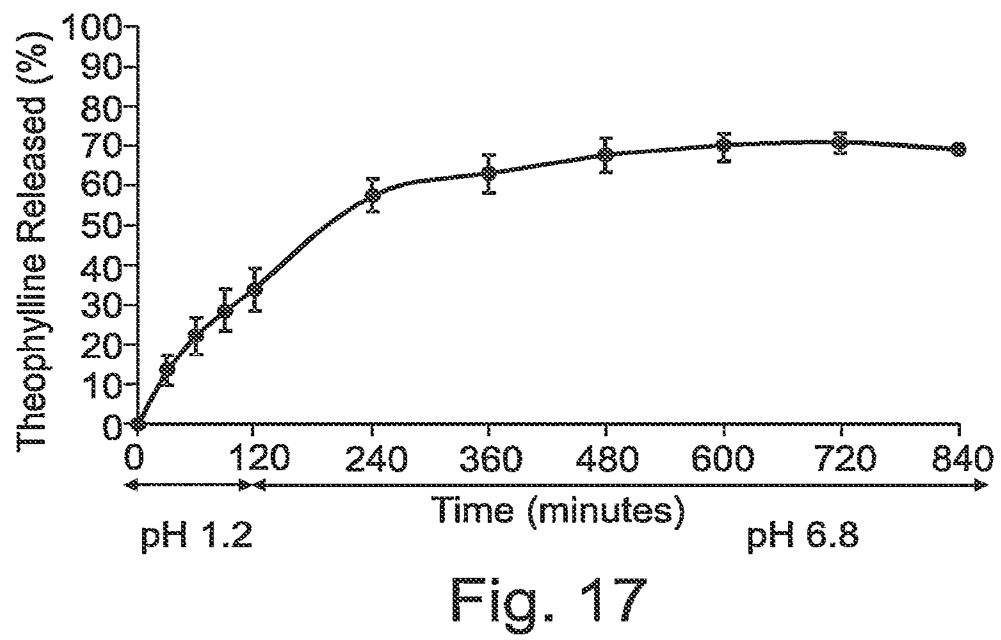
FIG. 17 shows release profiles for theophylline-cored-capsules produced with extended release shells containing Eudragit RL 100.

FIG. 17 shows release profiles for theophylline-cored-capsules produced with extended release shells containing Eudragit RL 100.

This example demonstrates the possibility of producing liquid capsules containing a drug solution, and also demonstrates the flexibility of the invention to afford immediate and extended release patterns.

Example 14—Example Capsules Containing Granules

In this example we demonstrate the ability of modified FDM 3D printer to produce a capsule whilst a secondary nozzle equipped with Clench Valve to control granule flow. The clench valve could be opened and closed in a co-ordinate fashion to allow filling of the capsule. Theophylline granules (25%) were prepared as a model powder. The shell of the capsule were made of Eudragit E and Eudragit L100-55 for immediate and delayed release respectively.

Modification of Hyrel SDS Clench Valve Head

A funnel was attached to a flexible tube and installed on a clench valve to replace the need for a syringe head since powder flow will be due to gravity. A nozzle was attached to the other end of the tube for more precise dispensing. This was then linked to an SDS head from Hyrel 3D M30 modular 3D printer (Hyrel 3D, GA, US) to control dispensing.

Preparation of Theophylline Granules

Theophylline (250 g), lactose monohydrate (240 g), PVP K90 (10 g) and approximately 30 ml of water was mixing using a planetary mixer for about 15 min. Granulation was carried out manually using a 1 mm sieve size and the product was dried in an oven at 70° C. until no weight loss due to moisture was observed. The final product was passed through a 1 mm sieve and large granules were size reduced. Size distribution experiment was carried out on the granules using sieve sizes of 710, 500, 315, 250, 180 and 90 μm.

Optimisation of Granule Sizes for Powder Dispensing

The different granule size ranges were fed into the funnel. Powder flow was due to gravity which was then control by the clench valve.

Three sets of granules of the following size were used: 710-1000 μm, 500-710 μm and 315-500 μm due to the internal diameter of the tube used was blocking flow. 315-180 μm size range had a similar issue but to a lesser degree. The following size range (180-90 μm) produced the best flow and control using the clench valve.

Dispensing Accuracy of the Powder Dispenser

Granule sizes 180-90 μm was fed into the powder dispenser and a solid object with dimensions at shown in Table 16 was chosen as the printed object. The volume of the object was varied and the powder dispensed was collected and weight. The calibration curve was plotted.

TABLE 16 dimensions of square object design, volume and corresponding capsule volume following 3D printing process

| Capsule | Dimensions (mm) | | | Volume | |
|---|---|---|---|---|---|
| core no | X | Y | Z | ($mm^3$) | Core mass (mg ± SD) |
| 1 | 5 | 7.5 | 0.2 | 7.5 | 1718.5 ± 109 |
| 2 | 5 | 5 | 0.2 | 5 | 1122.8 ± 74 |
| 3 | 5 | 2.5 | 0.2 | 2.5 | 563.3 ± 65 |
| 4 | 5 | 1.25 | 0.2 | 1.25 | 322 ± 23 |

Figure 18:
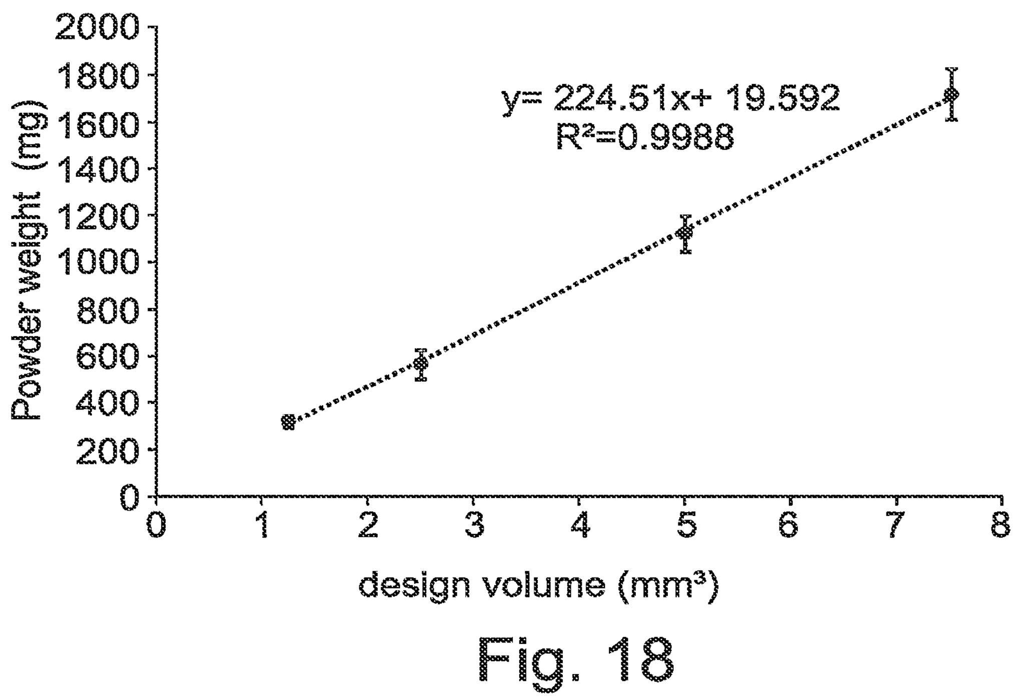
FIG. 18 shows a calibration curve for the powder dispenser (pinch valve).

FIG. 18 shows a calibration curve for the powder dispenser (pinch valve).

Preparation of Filaments for FDM 3D Printing

Eudragit EPO or Eudragit L100-55 was mixed with triethyl citrate and talc (45:5:50) before feeding it into the hot melt extruder at 100° C. and 130° C. respectively. This was mixed for about 5 min before extrusion at 10° C. below the feeding temperatures. A 1.7 mm nozzle was used during extrusion.

3D Printing of Capsules

The 3D printing of the capsule was carried out using a Hyrel system 30M with multiple heads for 3D printing. One of the heats was fitted with a FDM head and the other was the modified head for powder dispenser. A multiple phase printing mode was utilised in the printing were the bottom of the capsule was printed before the powder filling and eventual sealing of the capsule. The shell printing was carried out at 135° C. and 170° C. for Eudragit EPO and L100-55. The powder dispensing was carried out at room temperature.

In Vitro Release Studies

This was carried out using USP II dissolution tester. The paddle rotation was at 50 rpm and the temperature of the 0.1N HCL dissolution media set at 37° C. For the Eudragit RL 100 based capsule, the media pH was changed to 6.8 after 2 hrs and then to 7.4 after 6 hrs.

Figure 19:
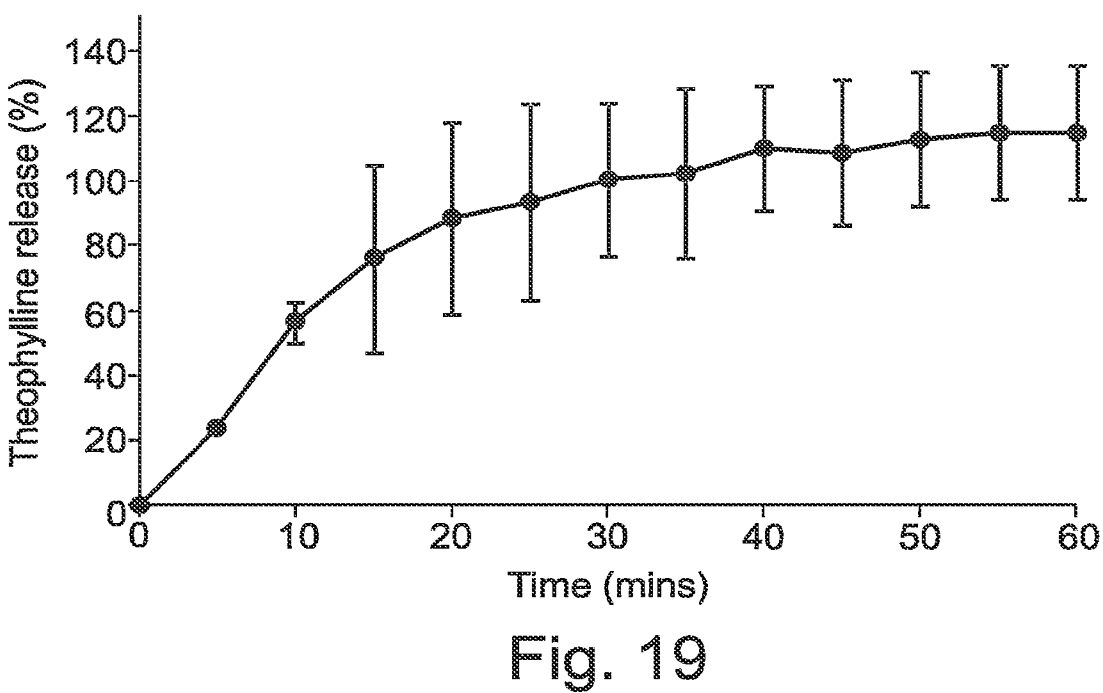
FIG. 19 shows an in vitro dissolution profile, in gastric medium (0.1 M HCl) USP II dissolution test, for an immediate release 3D printed capsule filled with theophylline granules.

FIG. 19 shows an in vitro dissolution profile, in gastric medium (0.1 M HCl) USP II dissolution test, for an immediate release 3D printed capsule filed with theophyline granules.

Figure 20:
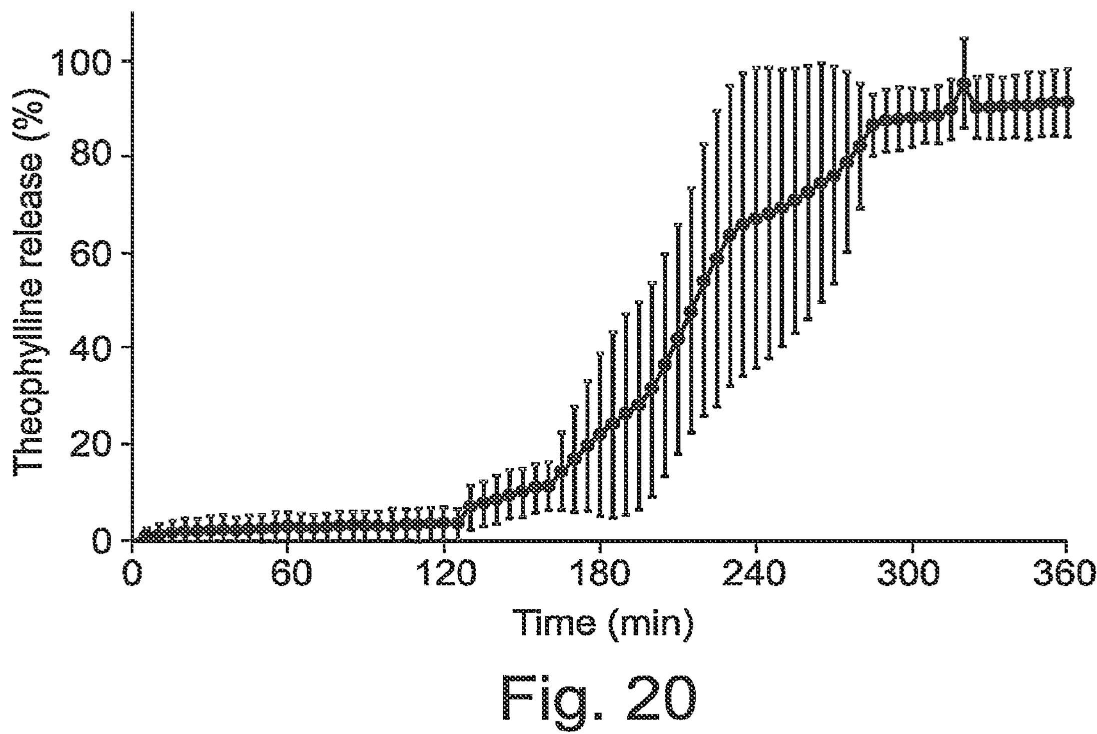
FIG. 20 shows an in vitro dissolution profile, in gastric medium (0.1 M HCl), of 3D printed delayed release entric capsule filled with theophylline granules.

FIG. 20 shows an in vitro dissolution profile, in gastric medium (0.1 M HCl), of 3D printed delayed release entric capsule filed with theophyline granules.

The invention claimed is:

1. A computer-implemented method of preparing a solid dosage form, for oral administration, the solid dosage form comprising a core and a three-dimensional shell surrounding the core, the method comprising:

i) providing an apparatus comprising:
  one or more structural printing nozzles for printing a three-dimensional open shell; and
  one or more non-structural dispensers for dispensing the core;

ii) providing a computer, running pursuant to solid dosage form printing software, configured to operate the apparatus and thereby control printing and dispensing;

iii) printing a shell composition or precursor thereof onto a build platform, via the one or more structural printing nozzles operating at a temperature between 6° and 350° C., to produce the three-dimensional open shell;

iv) dispensing into the three-dimensional open shell in a metered fashion at a temperature at or below 60° C., via the one or more non-structural dispensers, one or more core compositions, or precursor(s) thereof, to produce an open core-containing shell, wherein at least one of the core composition(s) comprises a pharmaceutically, nutraceutically, or food-supplement active ingredient; wherein at least one of the one or more core compositions, or precursor(s) thereof, is a liquid core composition; and wherein the one or more non-structural dispensers are either unheated or are otherwise associated with a temperature control element configured to maintain the temperature thereof at or below 60° C.; and v) closing the open core-containing shell;

wherein the one or more structural printing nozzles are one or more heated extrusion nozzles;

wherein steps iii)-v) are performed sequentially;

wherein the shell has a 3D-printed layer structure, whereas the core is solid, liquid, or gelled at standard ambient temperature and pressure (SATP) and has a non-3D-printed-layered structure.

2. The computer-implemented method as claimed in claim 1, wherein the liquid core composition is a liquid solution, a liquid dispersion, a liquid emulsion, or a liquid suspension.

3. The computer-implemented method as claimed in claim 1, wherein the liquid core composition comprises the pharmaceutically, nutraceutically, or food-supplement active ingredient.

4. The computer-implemented method as claimed in claim 1, wherein at least one of the one or more core compositions, or precursor(s) thereof, is a solid core composition.

5. The computer-implemented method as claimed in claim 4, wherein the solid core composition is a particulate solid.

6. The computer-implemented method as claimed in claim 5, wherein the solid core composition comprises the pharmaceutically, nutraceutically, or food-supplement active ingredient.

7. The computer-implemented method as claimed in claim 1, wherein the core is liquid, at SATP.

8. The computer-implemented method as claimed in claim 7, wherein the core is a liquid solution, a liquid dispersion, a liquid emulsion, or a liquid suspension.

9. The computer-implemented method as claimed in claim 1, wherein closing the open core-containing shell comprises printing a closure upon the open core-containing shell.

10. The computer-implemented method as claimed in claim 9, wherein printing the closure upon the open core-containing shell comprises printing a printing composition via a structural printing nozzle operating at a temperature between 6° and 350° C., wherein the structural printing nozzle is the same or different to a structural printing nozzle employed to print the three-dimensional open shell.

11. The computer-implemented method as claimed in claim 10, wherein the printing composition is the same or different to the shell composition or precursor thereof of the three-dimensional open shell.

12. The computer-implemented method as claimed in claim 1, wherein the method comprises producing a solid dosage form whose core is physically detached from the shell and physically movable therein in the presence of free internal space.

13. The computer-implemented method as claimed in claim 1, wherein the method comprises producing a solid dosage form whose core comprises at least one pharmaceutical active.

14. The computer-implemented method as claimed in claim 13, wherein the at least one pharmaceutical active is or comprises a thermosensitive biopharmaceutical.

15. The computer-implemented method as claimed in claim 13, wherein the core comprises one or more pharmaceutically acceptable excipients or carriers.

16. The computer-implemented method as claimed in claim 13, wherein the method comprises producing a solid dosage form whose core comprises more than one pharmaceutically active.

17. The computer-implemented method as claimed in claim 1, wherein the method comprises producing a solid dosage form comprising multiple shells.

18. The computer-implemented method as claimed in claim 1, wherein the method comprises producing a solid dosage form comprising multiple different core compositions.

19. The computer-implemented method as claimed in claim 1, wherein the three-dimensional open shell is printed with a shell printing filament, comprising the shell composition or a precursor thereof, via a structural printing nozzle that is a fused filament fabrication printing nozzle.

20. The computer-implemented method as claimed in claim 1, wherein at least one of the one or more structural printing nozzles and at least one of the one or more non-structural dispensers are incorporated within a 3D printer.

21. The computer-implemented method as claimed in claim 20, wherein the 3D printer is a fused filament fabrication (FFF) 3D printer.

22. A computer-readable medium comprising solid dosage form printing software code executable to cause a computer to perform the computer-implemented method as claimed in claim 1 when the software code is executed on a computer.

23. An apparatus for preparing a solid dosage form, for oral administration, the solid dosage form comprising a core and a three-dimensional shell surrounding the core, the apparatus comprising:

a 3D printer; and a build platform upon which the solid dosage form is printable; and a computer;

wherein the apparatus further comprises or is otherwise associated with:

one or more structural printing nozzles for printing a three-dimensional open shell; and one or more non-structural dispensers for dispensing the core;

wherein the computer, running pursuant to solid dosage form printing software, is configured to operate the apparatus to:

i) print a shell composition or precursor thereof onto the build platform, via the one or more structural printing nozzles operating at a temperature between 6° and 350° C., to produce the three-dimensional open shell;

ii) dispense into the three-dimensional open shell in a metered fashion at a temperature at or below 60° C., via the one or more non-structural dispensers, one or more core compositions, or precursor(s) thereof, to produce an open core-containing shell, wherein at least one of the core composition(s) comprises a pharmaceutically, nutraceutically, or food-supplement active ingredient, and wherein the one or more non-structural dispensers are either unheated or are otherwise associated with a temperature control element configured to maintain the temperature thereof at or below 60° C.; and iii) closing the open core-containing shell;

wherein the one or more structural printing nozzles are one or more heated extrusion nozzles;

wherein steps i)-iii) are performed sequentially;

wherein the shell has a 3D-printed layer structure, whereas the core is solid, liquid, or gelled at standard ambient temperature and pressure (SATP) and has a non-3D-printed-layered structure.

24. The apparatus as claimed in claim 23, wherein the apparatus comprises the one or more core compositions.

25. The apparatus as claimed in claim 24, wherein at least one of the one or more core compositions, or precursor(s) thereof, is a liquid core composition.

26. The apparatus as claimed in claim 25, wherein the liquid core composition comprises the pharmaceutically, nutraceutically, or food-supplement active ingredient.

27. The computer-implemented method as claimed in claim 19, wherein the shell printing filament is conveyed, via one or more conveyors, from a storage position to the structural printing nozzle through which the shell printing filament is extruded while shell printing filament continues to be conveyed towards the structural printing nozzle from the storage position.

* * * * *